(12) United States Patent
Kunsch et al.

(10) Patent No.: US 7,247,714 B2
(45) Date of Patent: Jul. 24, 2007

(54) PROTECTION AGAINST OXIDATIVE STRESS AND INFLAMMATION BY A CYTOPROTECTIVE RESPONSE ELEMENT

(75) Inventors: Charles Kunsch, Norcross, GA (US); Signe E. Varner, Los Angeles, CA (US); Xilin Chen, Alpharetta, GA (US); Jayraz Luchoomun, Lilburn, GA (US)

(73) Assignee: Atherogenics, Inc., Alpharetta, GA (US)

( * ) Notice: Subject to any disclaimer, the term of this patent is extended or adjusted under 35 U.S.C. 154(b) by 11 days.

(21) Appl. No.: 10/271,429

(22) Filed: Oct. 16, 2002

(65) Prior Publication Data

US 2004/0023233 A1    Feb. 5, 2004

Related U.S. Application Data

(60) Provisional application No. 60/329,870, filed on Oct. 16, 2001.

(51) Int. Cl.
| | |
|---|---|
| *C07H 21/04* | (2006.01) |
| *C07K 1/00* | (2006.01) |
| *C12Q 1/00* | (2006.01) |
| *C12Q 1/68* | (2006.01) |
| *C12N 1/20* | (2006.01) |
| *C12N 15/00* | (2006.01) |

(52) U.S. Cl. .................. 536/23.1; 536/23.4; 435/4; 435/252.3; 435/320.1; 435/6; 530/350

(58) Field of Classification Search ............ 435/252.3, 435/183, 320.1, 4; 536/23.1, 24.1, 23.2, 536/23.4; 530/350

See application file for complete search history.

(56) References Cited

U.S. PATENT DOCUMENTS

| 5,994,061 A | 11/1999 | Tam et al. |
| 6,018,025 A | 1/2000 | Falb et al. .................. 530/350 |
| 6,120,994 A | 9/2000 | Tam .............................. 435/6 |

FOREIGN PATENT DOCUMENTS

| WO | WO 90/01548 | * | 2/1990 |
| WO | WO 00/39275 A2 | | 6/2000 |

OTHER PUBLICATIONS

Sequence Alingment—WO 90/01548.*

(Continued)

*Primary Examiner*—Tekchand Saidha
*Assistant Examiner*—Yong D. Pak
(74) *Attorney, Agent, or Firm*—King & Spalding

(57) ABSTRACT

This invention is in the area of regulatory DNA sequences and their methods of use. Specifically, DNA sequences found in the regulatory region of cytoprotective genes are described that are termed cytoprotective response elements. DNA constructs also are provided that include cytoprotective response elements operably linked to heterologous protein coding sequence, as well as cells and non-human organisms that include the cytoprotective response elements optionally operably linked to a heterologous protein coding sequence, and a method for screening for a compound that increases mRNA or protein regulated by a cytoprotective response element. It has been discovered that the cytoprotective response elements mediate the coordinate activation of certain genes that protect cells from damaging effects of oxidative stress, and that they do so, for example during conditions of hemodynamic shear stress.

20 Claims, 22 Drawing Sheets

Shear stress induction of CPRE-regulated genes

OTHER PUBLICATIONS

Asakura, et al., "Flow Patterns and Spatial Distribution of Atherosclerotic Lesions in Human Coronary Arteries," Circulation Research, Apr. 1990, pp. 1045-1066, vol. 66, No. 4.

Beyer, et al., "The role of DT-diaphorase in the maintenance of the reduced antioxidant form of coenzymeQin membrane systems," Proc. Natl. Acad. Sci. USA, Mar. 1996, pp. 2528-2532, vol. 93.

Camhi, et al., "Induction of Heme Oxygenase-1 Gene Expression by Lipopolusaccaride Is Mediated by AP-1 Activation," Am. J. Respir. Cell Mol. Biol., 1995, pp. 387-398, vol. 13.

Chen, et al., "Laminar Flow Induction of Antioxidant Response Element-mediated Genes in Endothelial Cells," The Journal of Biological Chemistry, 2003, pp. 703-711, vol. 278, No. 2.

Chien, et al., "Effects of Mechanical Forces on Signal Transduction and Gene Expression in Endothelial Cells," Hypertension, 1998, pp. 162-169, vol. 31[part 2].

Choi, et al., Heme Oxygenase-1: Function, Regulation, and Implication of a Novel Stress-Inducible Protein in Oxidant-induced Lung Injury, Am. J. Respir. Cell Mol. Biol., 1996, pp. 9-19, vol. 15.

De Keulernaer, et al., "Oscillatory and Steady Laminar Shear Stress Differentially Affect Human Endothelial Redox State Role of a Superoxide-Producing NADH Oxidase," Circ Res., pp. 1094-1011, vol. 82.

Dinkova-Kostova, et al., "Chemoprotective Properties of Phenylpropenoids, Bis(benzlidene)cycloalkanones, and Related Michael Reaction Acceptors: Correlation of Potencies as Phase 2 Enzyme Inducers and Radical Scavengers," J. Med. Chem., 1998, pp. 5287-5296, vol. 41.

Flaherty, et al., "Endothelial Nuclear Patterns in the canine Artherial Tree with Particular Reference to Hemodynamic Events," Circulation Research, Jan. 1972, pp. 23-33, vol. XXX.

Hayashi, et al., "Induction of Heme Oxygenase-1 Suppresses Venular Leukocyte Adhesion Elicited by Oxidative Stress Role of Bilirubin Generated by the Enzyme," Circ Res., 1999, pp. 663-671, vol. 85.

Itoh, et al., "An Nrf2/Small Maf Heterodimer Mediates the Induction of Phase II Detoxifying Enzyme Genes through Antioxidant Response Elements," Biochemical and Biophysical Research Communications, 1997, pp. 313-322, vol. 236.

Itoh, et al., "Keap 1 represses nuclear activation of antioxidant responsive elements by Nrf2 through binding to the amino-terminal Neh2 domain," Genes & Development, 1999, pp. 76-86.

Jaiswal, et al., "Antioxidant Response Element," Biochemical Pharmacology, 1994, pp. 439-444, vol. 48.

Jaiswal, et al. "Regulation of Genes Encoding NAD(P)H:Quinone Oxidoreductases," Free Radical Biology & Medicine, 2000, pp. 254-262, vol. 29, Nos. 3/4.

Kataoka, et al., "Induction of Cellular Antioxidative Stress Genes through Heterodimeric Transcription Factor Nrf2/Small Maf by Antirheunatic Gold(I) Compounds," The Journal of Biological Chemistry, Sep. 7, 2001, pp. 34074-34081, vol. 276, No. 36.

Kataoka, et al., "Induction of Cellular Antioxidative Stress Genes through Heterodimeric Transcription Factor Nrf2/Small Maf by Antirheunatic Gold(I) Compounds," JBC Papers in Press, Published Jun. 27, 2001 as Manuscript M105383200, pp. 1-36 and 8 pages of drawings.

Ku, et al., "Pulsatile Flow of Atherosclerosis in the Human Carotid Bifurcation," Arterioscleorsis, 1985, pp. 293-302, vol. 5, No. 3.

Kunsch, et al., "Oxidative Stress as a Regulator of Gene Expression in the Vasculature," Circ Res., 1999, pp. 753-766, vol. 85.

Kuo, et al., "Superoxide Enhances Interleukin Iβ-Mediated Transcription of the Hepatocyte-Inducible Nitric Oxide Synthase Gene," Gastroenterology, 2000, pp. 608-618, vol. 118, No. 3.

Lee, et al., "Regulation of Heme Oxygenase-1 Expression In Vivo and In Vitro in Hyperoxic Lung Injury," Am. J. Respir. Cell Mol. Biol., pp. 556-568, vol. 14.

Li, et al., "Regulation of Human NAD(P)H:Quinone Oxidoreductase Gene," The Journal of Biological Chemistry, Jul. 1992, pp. 15097-15014, vol. 267, No. 21.

Medford, et al., "Laminar Shear Stress and Redox Sensitive Redox Sensitive Regulation of Human Vascular Endothelial Cell VACAM-1 Gene Expression," Abstract form the 67th Scientific Session I-83.

Nagel, et al., "Shear Stress Selective Upregulates Intercellular Adhesion Molecule-1 Expression in Cultured Human Vascular Endothelial Cells," Clin. Invest., Aug. 1994, pp. 885-891, vol. 94.

Nerem, et al., "Hemodynamic Influences on Vascular Endothelial Biology," Toxicologic Pathology, 1990, pp. 572-582, vol. 18, No. 4 (Part I).

Nguyen, et al., "Transcriptional Regulation of the Antioxidant Response Element," May 19, 2000, pp. 15466-15473, vol. 275, No. 20.

Poss, et al., "Reduced stress defense in heme oxygenase 1-deficient cells," Proc. Natl. Acad. Sci. USA, Sep. 1997, pp. 10925-10930, vol. 94.

Prestera, et al., Parallel Induction of Heme Oxygenase-1 and Chemoprotective Phase 2 Enzymes by Electrphiles and Antioxidants: Regulation by Upstream Antioxidant-Responsive Elements (ARE), Molecular Medicine, Nov. 1995, pp. 827-837, vol. 1, No. 7.

Resnick, et al., "Hemodynamic forces are complex regulators of endothelial gene expression," FASEB J., Jul. 1995, pp. 874-882, vol. 9.

Rushmore, et al., "Transcriptional Regulation of the Rat Glutathione S-Transferase Ya Subunit Gene," The Journal of Biological Chemistry, 1990, pp. 14648-14653, vol. 265, No. 24.

Rushmore, et al., The Antioxidant Responsive Element, The Journal of Biological Chemistry, Jun. 25, 1991, pp. 11632-11639, vol. 266, No. 18.

Siegel, et al., "The Reduction of α-Tocopherolquinone by Human NAD(P)H: Quinone Oxidoreductase: The Role of β-Tocopherolhydroquinone a a Cellular Antioxidant," Molecular Pharmacology, 1997, pp. 300-305, vol. 52.

Stocker, et al., "Antioxidant Activity of Albumin-bound Bilirubrin," Proc. Natl. Acad. Sci., Aug. 1987, pp. 5918-5922, vol. 84.

Talalay, et al., "Identification of a common chemical signal regulating the induction of enzymes that protect against chemical carcinogenesis," Proc. Natl. Acad. Sci., Nov. 1988, pp. 8261-8265, vol. 85.

Topper, et al., "Identification of vascular endothelial genes differentially responsive to fluid mechanical stimuli: Cyclooxygenase-2, manganese superoxide dismutase, and endothelial cell nitric oxide sythase are selectively up-regulated by steady laminar shear stress," Proc. Natl. Acad. Sci., Sep. 1996, pp. 10417-10422, vol. 93.

Tsuboi, et al., "Flow Stimulates ICAM-1 Expression Time and Shear Stress Dependently in Cyultured Human Endothelial Cells," Biochemical and Biophysical Research Communications, Jan. 26, 1995, pp. 988-996, vol. 206, No. 3.

Venugopal, et al., "Nrf1 and Nrf2 positively and cFos and Fra1 negatively regulate the human antioxidant response element-mediated expression of DAD(P)h:Quinone Oxidoreductase$_1$ gene," Proc. Natl. Acad. Sci., Dec. 1996, pp. 14960-14965, vol. 93.

Wasserman, et al., "Functional antioxidant responsive elements," Proc. Natl. Acad. Sci., May 1997, pp. 5361-5366, vol. 94.

Willis, et al., "Heme oxygenase: A novel target for the modulation of inflammatory response," Nature Medicine, Jan. 1996, pp. 87-90, vol. 2, No. 1.

Xie, et al., "ARE- and TRE-mediated Regulation of Gene Expression," The Journal of Biological Chemistry, Mar. 24, 1995, pp. 6984-6900, vol. 270, No. 12.

Yachie, et al., "Oxidative stress causes enhanced endothelial cell injury in human heme oxygenae-1 deficiency," J. Clin. Invest., 1999, pp. 129-135, vol. 103, No. 1.

Yet, et al., "Induction of Heme Oxygenase-1 Expression in Vascular Smooth Muscle Cells," The Journal of Biological Chemistry, Feb. 14, 1997, pp. 4295-4301, vol. 272, No. 7.

Alam, J., et al., "Nrf2, a Cap'n'Collar transcription factor, regulates induction of the heme oxygenase-1 gene," *J. Biol. Chem.*, 274(37):26071-26078 (Sep. 10, 1999).

Chan, K., et al., "Nrf2 is essential for protection against acute pulmonary injury in mice," *Proc. Natl. Acad. Sci. U S A*, 96(22):12731-12736 (Oct. 26, 1999).

Chen, Y.-H., et al., "A CCAAT/enhancer-binding protein site within antioxidant/electrophile response element along with CREB-binding protein participate in the negative regulation of rat GST-Ya gene in vascular smooth muscle cells," *J. Biol. Chem.*, 275(35):27366-27376 (Sep. 1, 2000).

Dhakshinamoorthy, S., et al., "Functional characterization and role of INrf2 in antioxidant response element-mediated expression and antioxidant induction of NAD(P)H:quinone oxidoreductase 1 gene," *Oncogene*, 20(29):3906-3917 (Jun. 28, 2001).

Dhakshinamoorthy, S., et al., "Small maf (MafG and MafK) proteins negatively regulate antioxidant response element-mediated expression and antioxidant induction of the NAD(P)H:Quinone oxidoreductase 1 gene," *J. Biol. Chem.*, 275(51):40134-40141 (Dec. 22, 2000).

Favreau, L.V., et al., "The rat quinone reductase antioxidant response element. Identification of the nucleotide sequence required for basal and inducible activity and detection of antioxidant response element-binding proteins in hepatoma and non-hepatoma cell lines," *J. Biol. Chem.*, 270(41):24468-24474 (Oct. 13, 1995).

Huang, H.-C., et al., "Regulation of the antioxidant response element by protein kinase C-mediated phosphorylation of NF-E2-related factor 2," *Proc. Natl. Acad. Sci. U S A.*, 97(23):12475-12480 (Nov. 7, 2000).

Inoue, N., et al., "Shear stress modulates expression of Cu/Zn superoxide dismutase in human aortic endothelial cells," *Circ. Res.*, 79(1):32-37 (Jul. 1996).

Ishii, T., et al., "Transcription factor Nrf2 coordinately regulates a group of oxidative stress-inducible genes in macrophages," *J. Biol. Chem.*, 275(21):16023-16029 (May 26, 2000).

Jaiswal, A.K., "Human NAD(P)H:quinone oxidoreductase$_2$: Gene structure, activity, and tissue-specific expression," *J. Biol. Chem.*, 269(20):14502-14508 (May 20, 1994).

Jeyapaul, J., et al., "Nrf2 and c-Jun regulation of antioxidant reponse element (ARE)-mediated expression and induction of gamma-glutamylcysteine synthetase heavy subunit gene," *Biochem. Pharmacol.*, 59(11):1433-1439 (Jun. 1, 2000).

Li, J., et al., "Microarray analysis reveals an antioxidant responsive element-driven gene set involved in conferring protection from an oxidative stress-inducted apoptosis in IMR-32 cells," *J. Biol. Chem.*, 277(1):388-394 (Jan. 4, 2002; electronically published Oct. 30, 2001).

Li, N., et al., "Induction of heme oxygenase-1 expression in macrophage by diesel exhaust particle chemicals and quinones via the antioxidant-responsive element," *J. Immunol.*, 165(6):3393-3401 (Sep. 15, 2000).

Moinova, H.R., et al., "An electrophile responsive element (EpRE) regulates beta-naphthoflavone induction of the human gamma-glutamylcysteine synthetase regulatory subunit gene. Constitutive expression is mediated by an adjacent AP-1 site," *J. Biol. Chem.*, 273(24):14683-14689 (Jun. 12, 1998).

Mulcahy, R.T., et al., "Constitutive and β-naphthoflavone-induced expression of the human γ-glutamylcysteine synthetase heavy subunit gene is related by a distal antioxidant repsonse element/TRE sequence," *J. Biol. Chem.*, 272(11):7445-7454 (Mar. 14, 1997).

Radjendirane, V., et al., "Antioxidant response element-mediated 2,3,7,8-tetrachlorodibenzo-p-dioxin (TCDD) induction of human NAD(P)H:quinone oxidoreductase 1 gene expression," *Biochem. Pharmacol.*, 58(10):1649-1655 (Nov. 15, 1999).

Tsuji, Y., et al., "Coordinate transcriptional and translational regulation of ferritin in response to oxidative stress," *Mol. Cell Biol.*, 20(16):5818-5827 (Aug. 2000).

Wild, A.C., et al., "Regulation of gamma-glutamylcysteine synthetase subunit gene expression by the transcription factor Nrf2," *J. Biol. Chem.*, 274(47):33627-33636 (Nov. 19, 1999).

* cited by examiner

Shear stress induction of CPRE-regulated genes

Timecourse of NQO1 Gene Expression

Effects of Laminar or Ocillatory Shear Stress on NQO1 mRNA Levels in Endothelial cells

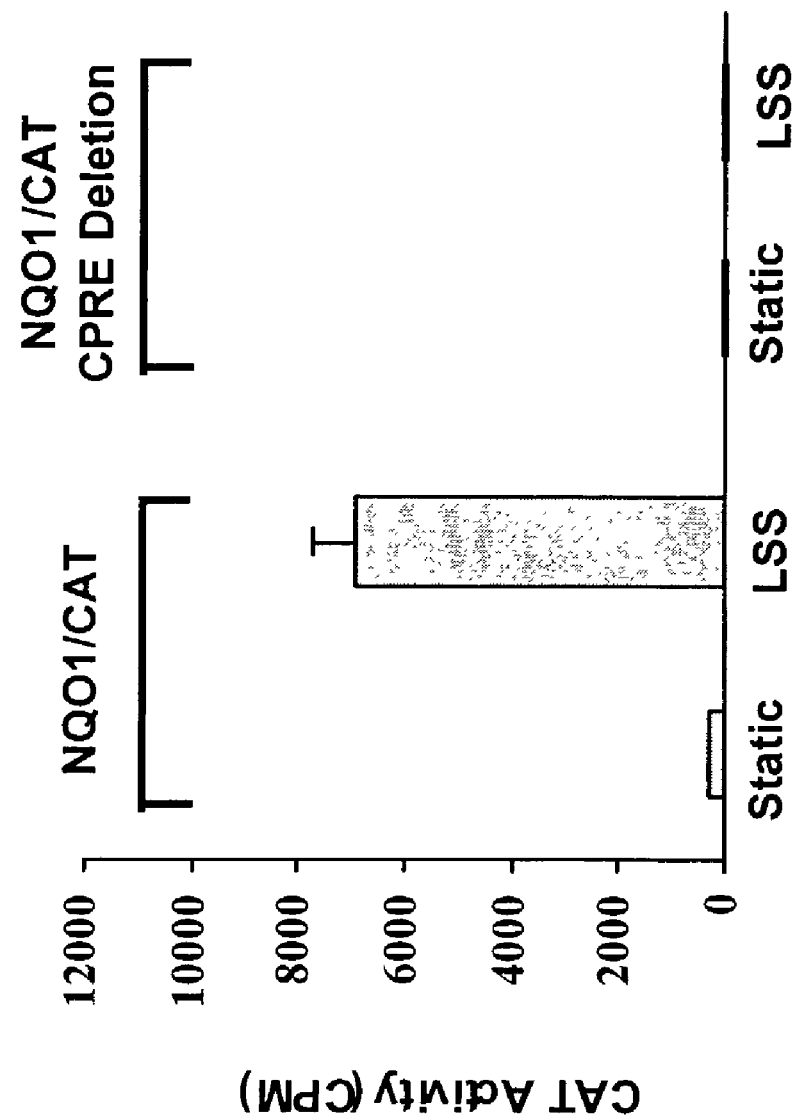

Figure 6

DNA sequence alignment of CPREs from shear stress regulated genes

RTGACWNAGCANW — CONSENSUS CPRE (SEQ. ID NO. 1)

GTGACTCAGCAGA — NQO1 (SEQ. ID NO. 3)
ATGAGGTGGCAGA — NQO2 (SEQ. ID NO. 4)
ATGACAAAGCACT — FERRITIN -H (SEQ. ID NO. 5)
GTGACTCAGCATT — FERRITIN - H (SEQ. ID NO. 6)
GTGACTCAGCAGA — FERRITIN -L (SEQ. ID NO. 7)
GTGACTCAGCAAA — HO-1 (SEQ. ID NO. 8)
ATGACACAGCATA — HO-1 (SEQ. ID NO. 9)
GTGACAAAGCAAA — GST (SEQ. ID NO. 10)
TTGACAGAGCAAT — γ-GCS (SEQ. ID NO. 11)
GTGACAGAGCAAT (SEQ. ID NO. 12)
ATGACTCAGCAGA (SEQ. ID NO. 13)
ATGACTCAGCAGA (SEQ. ID NO. 14)
ATGACTCAGCAGT (SEQ. ID NO. 15)
ATGACTCTGCAGA (SEQ. ID NO. 16)
ATGACACAGCAGT (SEQ. ID NO. 17)
GTGACACAGCAGT (SEQ. ID NO. 18)
ATGACACAGCAGT (SEQ. ID NO. 19)
ATGACACAGCATT (SEQ. ID NO. 19)
ATGACACAGCAAT (SEQ. ID NO. 20)

Code: A = Adenine      R = A/G
G = Guanine            Y = C/T
T = Thymine            M = C/A
C = Cytosine           W = A/T
S = G/C Diagram of p3xCPRE/Luc Effects of Laminar Shear Stress on CPRE-Driven Promoter Activity in Human Microvascular Endothelial Cells

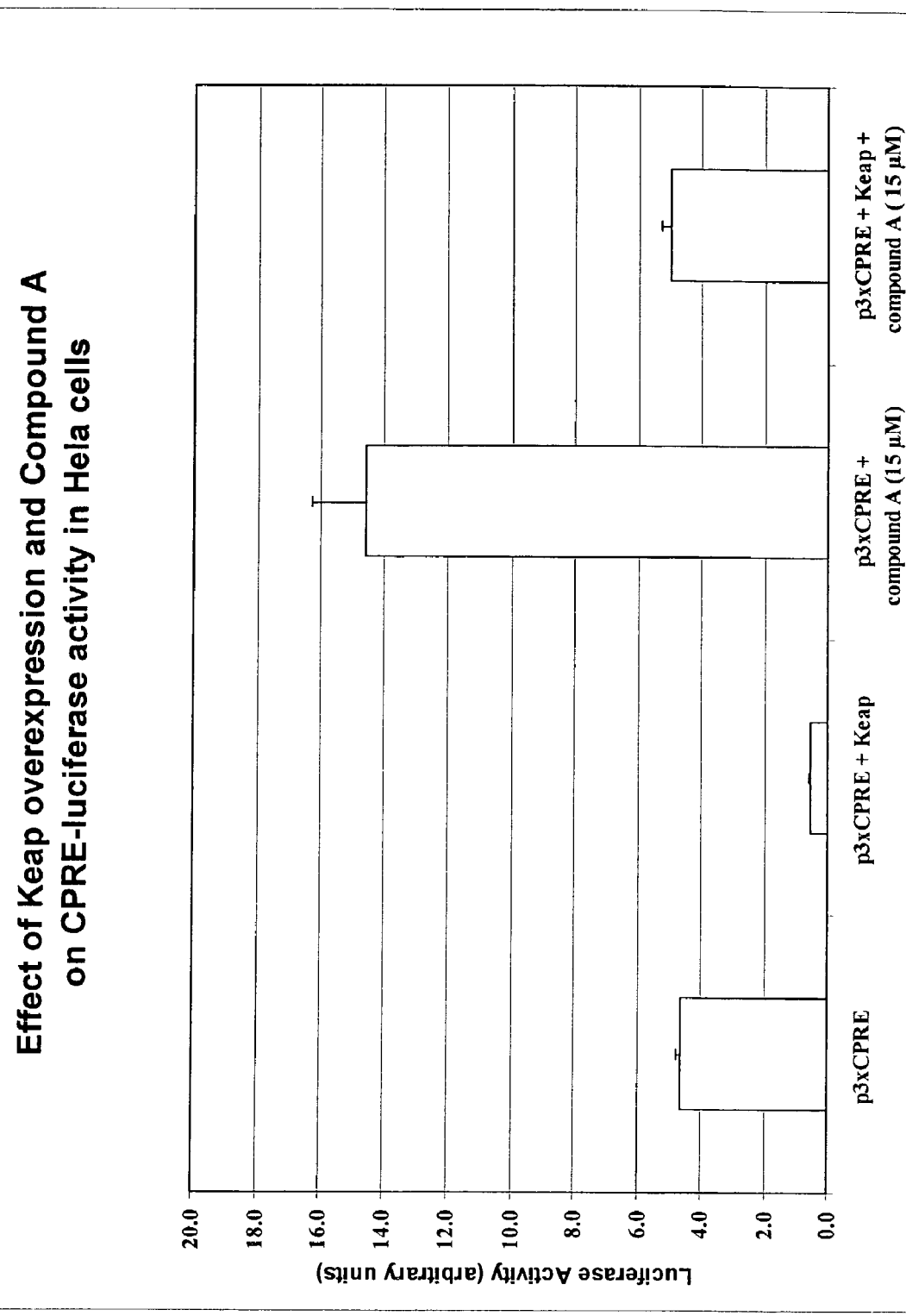

NQO1 Inhibits TNF-α-Activated VCAM-1 Gene Expression in Endothelial Cells

Expression of Nrf2 in Endothelial Cells Inhibits TNF-α-Activated VCAM-1z Gene Expression t-BHQ and Compound A induce CPRE-luciferase activity in HMEC cells t-BHQ and Compound A induce CPRE-luciferase activity in Hela cells Dose effect of Compound A on CPRE-luciferase activity in Hela cells Dose effect of Compound A on CPRE-luciferase activity in Hela cells stably transfected with p3xCPRE/Luc Effect of Compound A on Airway Hyperreactivity in a Mouse Model of Asthma Oral Administration Dosing qd D0-14

Effect of Compound G in a mouse model of allergic inflammation
Mouse Peritonitis model
Intravenous administration 1h prior to challenge

SEQUENCE LISTING

```
<160> NUMBER OF SEQ ID NOS: 42

<210> SEQ ID NO 1
<211> LENGTH: 13
<212> TYPE: DNA
<213> ORGANISM: artificial sequence
<220> FEATURE:
<223> OTHER INFORMATION: consensus sequence
<220> FEATURE:
<221> NAME/KEY: misc_feature
<222> LOCATION: (1)..(1)
<223> OTHER INFORMATION: r=a or g
<220> FEATURE:
<221> NAME/KEY: misc_feature
<222> LOCATION: (7)..(7)
<223> OTHER INFORMATION: n= a, g, c or t
<220> FEATURE:
<221> NAME/KEY: misc_feature
<222> LOCATION: (12)..(12)
<223> OTHER INFORMATION: n= a, g, c or t
<220> FEATURE:
<221> NAME/KEY: misc_feature
<222> LOCATION: (13)..(13)
<223> OTHER INFORMATION: w= a or t
<220> FEATURE:
<221> NAME/KEY: misc_feature
<222> LOCATION: (6)..(6)
<223> OTHER INFORMATION: w=a or t

<400> SEQUENCE: 1
rtgacwnagc anw                                                        13

<210> SEQ ID NO 2
<211> LENGTH: 90
<212> TYPE: DNA
<213> ORGANISM: artificial sequence
<220> FEATURE:
<223> OTHER INFORMATION: 3XCPRE-1

<400> SEQUENCE: 2
```
gagctccagt cacagtgact cagcagaatc gagctccagt cacagtgact cagcagaatc        60
gagctccagt cacagtgact cagcagaatc                                          90

<210> SEQ ID NO 3
<211> LENGTH: 13
<212> TYPE: DNA
<213> ORGANISM: human

<400> SEQUENCE: 3
gtgactcagc aga                                                            13

<210> SEQ ID NO 4
<211> LENGTH: 13
<212> TYPE: DNA
<213> ORGANISM: human

<400> SEQUENCE: 4
atgaggtggc aga                                                            13

<210> SEQ ID NO 5
<211> LENGTH: 13
<212> TYPE: DNA
<213> ORGANISM: human

<400> SEQUENCE: 5
atgacaaagc act                                                            13

<210> SEQ ID NO 6
<211> LENGTH: 13
<212> TYPE: DNA
<213> ORGANISM: human

<400> SEQUENCE: 6
gtgactcagc att                                                            13

<210> SEQ ID NO 7
<211> LENGTH: 13
<212> TYPE: DNA
<213> ORGANISM: human

<400> SEQUENCE: 7
gtgactcagc aga                                                            13

<210> SEQ ID NO 8
<211> LENGTH: 13
<212> TYPE: DNA
<213> ORGANISM: human

<400> SEQUENCE: 8
gtgactcagc aaa                                                            13

<210> SEQ ID NO 9
<211> LENGTH: 13
<212> TYPE: DNA
<213> ORGANISM: human

<400> SEQUENCE: 9
atgacacagc ata                                                            13

<210> SEQ ID NO 10
<211> LENGTH: 13
<212> TYPE: DNA

-continued

<213> ORGANISM: human

<400> SEQUENCE: 10
gtgacaaagc aaa                                                          13

<210> SEQ ID NO 11
<211> LENGTH: 13
<212> TYPE: DNA
<213> ORGANISM: human

<400> SEQUENCE: 11
ttgacagagc aat                                                          13

<210> SEQ ID NO 12
<211> LENGTH: 13
<212> TYPE: DNA
<213> ORGANISM: human

<400> SEQUENCE: 12
gtgacagagc aat                                                          13

<210> SEQ ID NO 13
<211> LENGTH: 13
<212> TYPE: DNA
<213> ORGANISM: human

<400> SEQUENCE: 13
atgactcagc aga                                                          13

<210> SEQ ID NO 14
<211> LENGTH: 13
<212> TYPE: DNA
<213> ORGANISM: human

<400> SEQUENCE: 14
atgactcagc aga                                                          13

<210> SEQ ID NO 15
<211> LENGTH: 13
<212> TYPE: DNA
<213> ORGANISM: human

<400> SEQUENCE: 15
atgactcagc agt                                                          13

<210> SEQ ID NO 16
<211> LENGTH: 13
<212> TYPE: DNA
<213> ORGANISM: human

<400> SEQUENCE: 16
atgactctgc aga                                                          13

<210> SEQ ID NO 17
<211> LENGTH: 13
<212> TYPE: DNA
<213> ORGANISM: human

<400> SEQUENCE: 17
gtgacacagc agt                                                          13

<210> SEQ ID NO 18
<211> LENGTH: 13

```
<212> TYPE: DNA
<213> ORGANISM: human

<400> SEQUENCE: 18
atgacacagc agt                                                            13

<210> SEQ ID NO 19
<211> LENGTH: 13
<212> TYPE: DNA
<213> ORGANISM: human

<400> SEQUENCE: 19
atgacacagc att                                                            13

<210> SEQ ID NO 20
<211> LENGTH: 13
<212> TYPE: DNA
<213> ORGANISM: human

<400> SEQUENCE: 20
atgacacagc aat                                                            13

<210> SEQ ID NO 21
<211> LENGTH: 39
<212> TYPE: DNA
<213> ORGANISM: artificial sequence
<220> FEATURE:
<223> OTHER INFORMATION: 3XCPRE-2
<220> FEATURE:
<221> NAME/KEY: misc_feature
<222> LOCATION: (1)..(1)
<223> OTHER INFORMATION: r= a or g
<220> FEATURE:
<221> NAME/KEY: misc_feature
<222> LOCATION: (14)..(14)
<223> OTHER INFORMATION: r= a or g
<220> FEATURE:
<221> NAME/KEY: misc_feature
<222> LOCATION: (27)..(27)
<223> OTHER INFORMATION: r= a or g
<220> FEATURE:
<221> NAME/KEY: misc_feature
<222> LOCATION: (6)..(6)
<223> OTHER INFORMATION: w= a or t
<220> FEATURE:
<221> NAME/KEY: misc_feature
<222> LOCATION: (14)..(14)
<223> OTHER INFORMATION: w= a or t
<220> FEATURE:
<221> NAME/KEY: misc_feature
<222> LOCATION: (19)..(19)
<223> OTHER INFORMATION: w= a or t
<220> FEATURE:
<221> NAME/KEY: misc_feature
<222> LOCATION: (26)..(26)
<223> OTHER INFORMATION: w= a or t
<220> FEATURE:
<221> NAME/KEY: misc_feature
<222> LOCATION: (39)..(39)
<223> OTHER INFORMATION: w= a or t
<220> FEATURE:
<221> NAME/KEY: misc_feature
<222> LOCATION: (7)..(7)
<223> OTHER INFORMATION: n= a or t or c or g
<220> FEATURE:
<221> NAME/KEY: misc_feature
<222> LOCATION: (12)..(12)
<223> OTHER INFORMATION: n= a or t or c or g
<220> FEATURE:
<221> NAME/KEY: misc_feature
<222> LOCATION: (20)..(20)
<223> OTHER INFORMATION: n= a or t or c or g
<220> FEATURE:
```

```
<221> NAME/KEY: misc_feature
<222> LOCATION: (25)..(25)
<223> OTHER INFORMATION: n= a or t or c or g
<220> FEATURE:
<221> NAME/KEY: misc_feature
<222> LOCATION: (33)..(33)
<223> OTHER INFORMATION: n= a or t or c or g
<220> FEATURE:
<221> NAME/KEY: misc_feature
<222> LOCATION: (38)..(38)
<223> OTHER INFORMATION: n= a or t or c or g

<400> SEQUENCE: 21
rtgacwnagc anwrtgacwn agcanwrtga cwnagcanw                                39

<210> SEQ ID NO 22
<211> LENGTH: 39
<212> TYPE: DNA
<213> ORGANISM: artificial sequence
<220> FEATURE:
<223> OTHER INFORMATION: 3XCPRE--3

<400> SEQUENCE: 22
gtgactcagc agagtgactc agcagagtga ctcagcaga                                39

<210> SEQ ID NO 23
<211> LENGTH: 9
<212> TYPE: DNA
<213> ORGANISM: Artificial Sequence
<220> FEATURE:
<223> OTHER INFORMATION: ARE consensus
<220> FEATURE:
<221> NAME/KEY: misc_feature
<222> LOCATION: (5)..(7)
<223> OTHER INFORMATION: n= a, g, c or t

<400> SEQUENCE: 23 tgacnnngc                                                                  9

<210> SEQ ID NO 24
<211> LENGTH: 11
<212> TYPE: DNA
<213> ORGANISM: artificial sequence
<220> FEATURE:
<223> OTHER INFORMATION: ARE
<220> FEATURE:
<221> NAME/KEY: misc_feature
<222> LOCATION: (1)..(1)
<223> OTHER INFORMATION: r = a or g
<220> FEATURE:
<221> NAME/KEY: misc_feature
<222> LOCATION: (3)..(3)
<223> OTHER INFORMATION: r = a or g
<220> FEATURE:
<221> NAME/KEY: misc_feature
<222> LOCATION: (6)..(8)
<223> OTHER INFORMATION: n = a, g, c or t

<400> SEQUENCE: 24
rgracnnngc t                                                              11

<210> SEQ ID NO 25
<211> LENGTH: 13
<212> TYPE: DNA
<213> ORGANISM: artificial sequence
<220> FEATURE:
<223> OTHER INFORMATION: MARE

<400> SEQUENCE: 25
tgctgactca gca                                                            13
```

```
<210> SEQ ID NO 26
<211> LENGTH: 20
<212> TYPE: DNA
<213> ORGANISM: artificial sequence
<220> FEATURE:
<223> OTHER INFORMATION: 5' primer gamma-GCS

<400> SEQUENCE: 26
tgaggccaac atgcgaaaac                                                    20

<210> SEQ ID NO 27
<211> LENGTH: 22
<212> TYPE: DNA
<213> ORGANISM: artificial sequence
<220> FEATURE:
<223> OTHER INFORMATION: 3' primer gamma-GCS

<400> SEQUENCE: 27
aaatcactcc ccagcgacaa tc                                                 22

<210> SEQ ID NO 28
<211> LENGTH: 17
<212> TYPE: DNA
<213> ORGANISM: artificial sequence
<220> FEATURE:
<223> OTHER INFORMATION: 5' primer NQO2

<400> SEQUENCE: 28
actgagcagg cagggct                                                       17

<210> SEQ ID NO 29
<211> LENGTH: 19
<212> TYPE: DNA
<213> ORGANISM: artificial sequence
<220> FEATURE:
<223> OTHER INFORMATION: 3' primer NQO2

<400> SEQUENCE: 29
atctgagggg caaggactt                                                     19

<210> SEQ ID NO 30
<211> LENGTH: 21
<212> TYPE: DNA
<213> ORGANISM: artificial sequence
<220> FEATURE:
<223> OTHER INFORMATION: 5' primer GST

<400> SEQUENCE: 30
gtttttgcca atccagaaga c                                                  21

<210> SEQ ID NO 31
<211> LENGTH: 21
<212> TYPE: DNA
<213> ORGANISM: artificial sequence
<220> FEATURE:
<223> OTHER INFORMATION: 3' primer GST

<400> SEQUENCE: 31
gctcccctcc tacctaaaat c                                                  21

<210> SEQ ID NO 32
<211> LENGTH: 22
<212> TYPE: DNA
<213> ORGANISM: artificial sequence
<220> FEATURE:
```

```
<223> OTHER INFORMATION: 5' primer NQO1

<400> SEQUENCE: 32
cctggccctt gcaatcttct ac                                              22

<210> SEQ ID NO 33
<211> LENGTH: 21
<212> TYPE: DNA
<213> ORGANISM: artificial sequence
<220> FEATURE:
<223> OTHER INFORMATION: 3' primer NQO1

<400> SEQUENCE: 33
cagctcggtc caatcccttc a                                               21

<210> SEQ ID NO 34
<211> LENGTH: 22
<212> TYPE: DNA
<213> ORGANISM: artificial sequence
<220> FEATURE:
<223> OTHER INFORMATION: 5' primer Ferritin-H

<400> SEQUENCE: 34
ctggccactg acaaaaatga cc                                              22

<210> SEQ ID NO 35
<211> LENGTH: 22
<212> TYPE: DNA
<213> ORGANISM: artificial sequence
<220> FEATURE:
<223> OTHER INFORMATION: 3'primer Ferritin-H

<400> SEQUENCE: 35
aacggcactt aaggaatctg ga                                              22

<210> SEQ ID NO 36
<211> LENGTH: 19
<212> TYPE: DNA
<213> ORGANISM: artificial sequence
<220> FEATURE:
<223> OTHER INFORMATION: 5' primer HO-1

<400> SEQUENCE: 36
ttgctgtagg gctttatgc                                                  19

<210> SEQ ID NO 37
<211> LENGTH: 19
<212> TYPE: DNA
<213> ORGANISM: artificial sequence
<220> FEATURE:
<223> OTHER INFORMATION: 3' primer HO-1

<400> SEQUENCE: 37
ctgcatttga ggctgagcc                                                  19

<210> SEQ ID NO 38
<211> LENGTH: 16
<212> TYPE: DNA
<213> ORGANISM: artificial sequence
<220> FEATURE:
<223> OTHER INFORMATION: 5' primer Ferritin-L

<400> SEQUENCE: 38
gcgcgagggc tacgag                                                     16
```

```
<210> SEQ ID NO 39
<211> LENGTH: 20
<212> TYPE: DNA
<213> ORGANISM: artificial sequence
<220> FEATURE:
<223> OTHER INFORMATION: 3' primer Ferritin-L

<400> SEQUENCE: 39
ctattggctg gagggagagg                                                    20

<210> SEQ ID NO 40
<211> LENGTH: 16
<212> TYPE: DNA
<213> ORGANISM: artificial sequence
<220> FEATURE:
<223> OTHER INFORMATION: 5' primer beta actin

<400> SEQUENCE: 40
atcggcggct ccatcc                                                        16

<210> SEQ ID NO 41
<211> LENGTH: 18
<212> TYPE: DNA
<213> ORGANISM: artificial sequence
<220> FEATURE:
<223> OTHER INFORMATION: 3' primer beta actin

<400> SEQUENCE: 41
ggggcacgaa ggctcatc                                                      18

<210> SEQ ID NO 42
<211> LENGTH: 85
<212> TYPE: DNA
<213> ORGANISM: artificial sequence
<220> FEATURE:
<223> OTHER INFORMATION: Sense strand- CPRE

<400> SEQUENCE: 42
gagctccagt cacagtgact cagcagaatc cagtcacagt gactcagcag aattccagtc        60
acagtgactc agcagaatca gatct                                              85
```

PROTECTION AGAINST OXIDATIVE STRESS AND INFLAMMATION BY A CYTOPROTECTIVE RESPONSE ELEMENT

This application claims priority to U.S. Ser. No. 60/329,870, filed Oct. 16, 2001.

FIELD OF THE INVENTION

This invention is in the area of regulatory DNA sequences and their methods of use. Specifically, DNA sequences found in the regulatory region of cytoprotective genes are described that are termed cytoprotective response elements. DNA constructs are also provided that include cytoprotective response elements operably linked to heterologous protein coding sequence, as well as cells and non-human organisms that include the cytoprotective response elements optionally operably linked to a heterologous protein coding sequence, and a method for screening for a compound that increases mRNA or protein regulated by a cytoprotective response element. It has been discovered that the cytoprotective response elements mediate the coordinate activation of certain genes that protect cells from damaging effects of oxidative stress, and that they do so, for example during conditions of hemodynamic shear stress.

BACKGROUND OF THE INVENTION

Inflammation is a normal response of the body to protect tissues from infection, injury or disease. The inflammatory response begins with the production and release of chemical agents by cells in the infected, injured or diseased tissue. These agents cause inflammation of the tissue, which generate additional signals that recruit leukocytes. Leukocytes destroy infective or injurious agents, and remove cellular debris from damaged tissue. Although inflammation is a normal response of the body to heal itself, if not controlled, it can result in undesirable chronic inflammation.

The vasculature regulates processes that control inflammation. At sites of injury or infection, cells of the vasculature (including smooth muscle cells and endothelial cells (ECs)) release chemical and protein mediators that attract leukocytes to the injured or damaged area. The leukocytes play a key role by migrating from the circulatory system into the infected area to help resolve the acute inflammation. Cell adhesion molecules expressed on the surface of endothelial cells are one of the primary regulators of this process and assist in recruiting the leukocytes to the affected area. Damaged or injured endothelium stimulates the expression of adhesion molecules, which are responsible for the interaction of leukocytes with the endothelial cell.

Hemodynamics and Vascular Inflammation

Originally viewed simply as a passive barrier or insulation, the endothelial lining is now considered to be a multi-functional organ whose health is essential to normal vascular physiology, and whose dysfunction can be a critical factor in the pathogenesis of vascular disease including inflammatory diseases. It serves as both an endocrine and paracrine organ with numerous regulatory functions. Because endothelial cells lie at the interface between the circulating blood and the vessel wall, they reside in a dynamic physical force environment, experiencing both a normal pressure force and a tangential shearing (frictional) force resulting from the flow of blood over the luminal surface. In recent years there has been considerable focus on the influence of this fluid shear stress on vascular endothelial cell biology (Nerem & Girard (1990) Toxicologic Pathology, 18(4)572-582). One of the first demonstrations that the endothelial cell responds to its hemodynamic environment was the observed alignment of endothelial cells in vivo with the direction of blood flow. (Flaherty, et al. (1972) Circ. Res. 30:23). The dramatic impact of shear stress on vascular inflammation is exemplified in the early events in the pathogenesis of atherosclerosis. The nonrandom distribution of early atherosclerotic lesions observed both in the natural disease process in humans and in experimental animal models suggests that hemodynamic influences can contribute to the early pathogenesis (Asakura & Karino (1990) Circ Res, 66:1045-1066; and Ku, et al. (1985) Arteriosclerosis, 5: 293-302). These early lesions are localized to branched and curved segments of large arteries that are characterized by non-directional and relatively low fluid shear stress. (Montenegro & Eggen (1968) Lab Invest. 18(5):586-593). Conversely, the lesion-protected areas of the vasculature are characterized by unidirectional and relatively high fluid shear stress. These observations led to the development of in vitro model systems that mimic the hemodynamic forces experienced by the endothelium in vivo, so that the effects of this important physical force can be studied in depth.

Substantial evidence now exists to support the role of endothelial cells as powerful transducers of its hemodynamic environment, and that such mechanical forces can directly affect endothelial cell biology (Nerem & Girard (1990) Toxicologic Pathology 18(4):572-582; and Nitzan & Gimrone (1995) FASEB J. 9:874-882). One of the most well-studied effects of fluid shear stress on endothelial cell biology is alteration of EC/leukocyte interactions. The altered adhesivity of leukocytes for the EC is due, at least in part, to the regulation of the adhesion proteins intercellular adhesion molecule-1 (ICAM-1) and vascular cell adhesion molecule-1 (VCAM-1). The expression of both ICAM-1 and VCAM-1 are regulated by shear stress (Tsuboi, et al., (1995) Biochem. Biophys. Res. Commun. 206(3):988-996; and Medford, et al., (1994) Circulation. 909(suppl I):I-83. Abstract). In addition, other genes (that function in maintaining vasoactivity, redox state, hemostasis, and growth control) whose expression is regulated by shear stress have been described (Chien, et al. ((1998) Hypertension 31:162-169)).

Oxidative Stress and Hemodynamics

It is now well accepted that oxidative stress and oxidant signaling pathways play important roles in vascular dysfunction associated with atherosclerosis and other inflammatory diseases. Indeed, oxidant stress causes changes in inflammatory gene expression (Kunsch & Medford (1999) Circ. Res. 85:753-766). For example, pro-oxidants stimulate the expression of VCAM-1 and MCP-1 on endothelial cells, whereas, antioxidants inhibit oxidant-stress induced expression of these genes. Cells normally contain endogenous proteins that help to reduce the levels of reactive oxygen species and prevent the damaging effects oxidative stress, thus protecting the cell.

It has been suggested that steady, laminar shear stress induces this protective phenotype of the cell, in part, by activating the expression of genes that function to protect the cell from oxidative stress. Several reports have demonstrated that exposure of endothelial cells to shear stress induces the expression of genes that regulate endothelial cell redox homeostasis including Manganese Superoxide Dismutase (MnSOD), catalase, nitric oxide synthase, Heme oxygenase-1 (HO-1) (Topper, et al., (1996) Proc. Natl. Acad. Sci USA. 93:10417-10422; and Inoue N, Ramasam, et al., (1996) Biochem Biophys Res Commun. 79:32-37). One recent study demonstrated that cells exposed to laminar shear stress (LSS) have lower levels of the free radical, superoxide, than cells exposed to oscillatory shear stress (OSS) (De Keulenaer, et al. (1998) Circ Res. 82:1094). DeKeulenaer et al. suggest that steady LSS can induce compensatory antioxidant defense mechanisms by the observed increased expression of SOD and antioxidant defense enzymes whose level of expression adapts to changes in oxidative stress. Therefore, the local hemodynamic environment of the vasculature can help to regulate intracellular oxidant stress by modulating the expression of genes that function in redox homeostasis. In addition, using a shear stress paradigm to identify genes related to cardiovascular disease, six genes were found to be upregulated (U.S. Pat. No. 6,018,025 to Falb). Although these initial studies have identified a few genes regulated by fluid shear stress, the mechanisms that allow endothelial cells to discriminate between the various types of fluid shear stress and thereby express an anti-inflammatory, antioxidative phenotype remains to be elucidated.

The specific nucleotide sequences that comprise the regulatory regions of genes that respond to hemodynamic influences of the cell, and therefore can mediate antioxidant and anti-inflammatory pathways, provide novel targets for modulating their expression. Particularly, PCT Publication No. WO 00/39275 filed by Florence Medical Ltd., et al., discloses a set of vectors comprising multiple shear stress response elements (SSRE) that include HO-1. The SSRE is defined generally as nucleic acids from the regulatory elements of genes that are regulated in endothelial cells through shear stress forces. The SSRE is further defined as an element necessary and/or sufficient to induce (or suppress) gene expression in endothelial cells exposed to shear stress. The invention provides a method for testing compounds for the ability to regulate endothelial cell gene expression, angiogenesis and/or vasculogenesis to treat disorders related to angiogenesis and or vasculogenesis. However, the specific nucleotide sequences that comprise the regulatory elements of genes that respond to shear stress stimuli have not yet been identified.

The Antioxidant Response Element (ARE)

The antioxidant response element (ARE) with underlined consensus sequence TGACNNNGC (SEQ ID NO 23) is now known to be a transcriptional regulatory element. It is found in the 5' flanking regions of several genes encoding enzymes involved in the phase II metabolism of xenobiotics, including GST, NQO1, and glucuronosyltransferase. (Rushmore, et al., (1991) J. Biol. Chem. 266:11632; and Jaiswal AK (1994) Biochem. Pharmacol. 48:439). The induction of these enzymes by transcriptional activation through the ARE results from cellular exposure to a variety of chemical entities including electrophilic compounds, antioxidants, Michael reaction acceptors, redox-cycling polyaromatic hydrocarbons, quinones and other agents capable of generating free radical species that alter the cellular redox state. The ability of these enzymes to conjugate redox-cycling chemicals is an important protective mechanism against electrophile and oxidative toxicity. Thus, oxidative stress appears to be the principle signal that acts, either directly or indirectly, through a signaling pathway leading to the transcriptional activation of genes encoding these enzymes. Although this antioxidant defense mechanism has been studied extensively as a hepatic detoxification mechanism, it has also been suggested that the ARE pathway can contribute to antioxidant defenses in the lung via activation of heme oxygenase. (Camhi., et al., (1995) Am. J. Respir. Cell Mol. Biol. 13:387).

U.S. Pat. No. 6,120,994 to Tam discloses an ARE, which constitutes the DNA consensus sequence: 5'-RGR AC NNN GCT-3' (SEQ ID NO 24) (wherein R is A or G). This patent discloses a method of screening for a compound that increases transcription of a mRNA regulated by the ARE. The ARE is present in a DNA construct containing the ARE operably linked to a protein coding sequence. This construct is used in an assay for cellular extracts of transcription products (either mRNA or protein) in the presence and absence of the compound.

The ARE disclosed in the '994 patent is identified as part of the proapoAI gene. This gene encodes apolipoprotein AI, the major protein component of high-density lipoprotein, which is believed to reduce atherosclerotic risk. Thus, increasing the levels of apolipoprotein via induction of ARE-mediated transcription is reported to have beneficial effects in preventing or treating animal or human atherosclerosis and cardiovascular disease. The '994 patent also teaches a system for screening and identifying compounds that increase transcription of an MRNA regulated by an ARE, for example apolipoprotein AI. In addition, the '994 patent provides a method of treating a human being or an animal with such a compound.

The Maf-recognition Element (MARE)

Recently, Kataoka et al. ((2001), J. Biol. Chem. 276 (36):34074) identified a maf recognition element, referred to as "MARE" having the DNA consensus sequence 5'-TGCT-GACTCAGCA-3' (SEQ ID NO 25). Specifically, Kataoka et al. describes the coordinate induction of the genes for gamma glutamyl cysteine synthase (γ-GCS), NQO1 and HO-1 via the activation of MARE by gold(I) compounds (gold(I) drugs). They also identify that the MARE transcription factors, Nrf-2/Small Maf, are activated by Gold(I) drugs.

Gold(I) drugs are in clinical use for treatment of rheumatoid arthritis. Kataoka et al. describes for the first time the molecular mechanism of action of these drugs. The gene products, γ-GCS, NQO1 and HO-1, which were found to be upregulated by gold(I) drugs are known to be involved in the anti-oxidative stress response as well as anti-inflammatory pathways. Thus, they speculate that the gold(I) drugs can protect against inflammation.

Heme Oxygenase (HO-1)

Heme oxygenase is the enzyme that oxidatively degrades protoheme IX to biliverdin and carbon monoxide. In mammals, biliverdin is further converted to bilirubin, an endogenous radical scavenger, through action of biliverdin reductase. (Stocker, et al., (1987) Proc. Natl. Acad. Sci. U.S.A. 84:5918-5922). Three isoforms of heme oxygenase have been identified; however, only HO-1 is inducible. Initial interest in HO-1 focused on its role in heme catabolism, however, recent studies show that HO-1 is highly responsive to oxidative stress and has potent antioxidant properties (Choi & Alam (1996) Am J. Respir. Cell Mol Biol. 15:9-19). When tissues are pre-exposed to HO-1 inducers their damage and/or acute inflammatory responses are markedly attenuated in a variety of models such as carrageenan-induced pleuritits. (Willis, et al. (1996) Nat Med. 2:87-89), oxidant-induced lung injury (Choi & Alam (1996) Am J. Respir. Cell Mol Biol. 15:9-19; and Lee, et al. (1996) Am. J. Respir. Cell Mol. Biol. 4:556), and endotoxin shock (Yet, et al. (1997) J Biol Chem. 272:4296-4301). In addition, HO-1-deficient humans' exhibit enhanced endothelial cell injury in the presence of oxidative stress (Poss & Tonegawa (1997) Proc. Natl. Acad. Sci. USA. 94:10925; and (Yachie, et al. (1999) J. Clin. Invest. 103:129). Recently, Hayashi and colleagues demonstrated that HO-1 attenuates leukocyte-endothelial cell adhesion in vivo through the action of bilirubin (Hayashi, et al. (1999) Circ Res 85:663-671). This can be one mechanism by which HO-1 is protective in inflammation. HO-1 is upregulated through its ARE site by acute complement-dependant inflammatory responses (Willis et al. (1996) Nature Medicine 2:87-90), as well as electrophilic compounds such as phorbol esters and heavy metals (Prestera et al. (1995) Molecular Medicine 1: 827-837).

NAD(P)H:Quinone Oxidoreductase (NQO1& NQO2)

NQO1 is a cytosolic flavoprotein found ubiquitously in eukaryotes. In addition to NQO1, at least one other homolog (NQO2) has been cloned from humans (~50% identity at the amino acid level). The expression of NQO1 is induced by exposure to many substances including: aromatic compounds, phenolic antioxidants, peroxides, mercaptans, phorbol esters, ionizing radiation, UV light, and hypoxia. The expression of NQO1 is high in liver and also many extra-hepatic tissues including kidney, skeletal muscle, lung, heart, and placenta. NQO1 is upregulated through its MARE/ARE site by rheumatic gold compounds Kataoka et al. ((2001), J. Biol. Chem. 276 (36):34074), as well as xenobiotics and antioxidants (Jaiswal (2000) Free Radical Biology and Medicine 29: 254-262).

It is believed that the primary function of NQO1 is to catalyze the obligatory two electron reductive metabolism and detoxification of quinones and their derivatives. Quinones are highly abundant in nature and human exposure to them is extensive. Quinones are found in all burnt organic materials, including automobile exhaust, cigarette smoke, and urban air pollutants. The obligatory two-electron reduction of quinones catalyzed by NQO1 competes with the one-electron reduction of quinones by other enzymes. These single electron reductions of quinones generate unstable semiquinones that undergo redox cycling in the presence of molecular oxygen leading to the formation of reactive oxygen species causing lipid peroxidation, membrane and DNA damage, oxidative stress, cytotoxicity and mutagenicity. NQO1 must compete with the single-electron reducing enzymes and allow for detoxification. NQO1 generally serves to protect the cell from the redox damaging effects of potentially toxic quinones and semiquinones.

Another major function of NQO1 is to maintain coenzyme Q (Ubiquinone) in the reduced form (Ubiquinol) in membranes. Coenzyme Q10 is a lipid-soluble constituent of (cardiac) mitochondrial membranes. CoQ10 functions as an electron carrier in the respiratory chain through its redox-active quinoid moiety. Other properties of Coenzyme Q10 include "membrane-stabilizing" activity and inhibition of membrane lipid peroxidation. Ubiquinols can react with oxygen radicals and thus prevent direct damage to biomolecules and initiation of lipid peroxidation. CoQ10 protects cardiac mitochondria against oxidative stress and reduces the damaging effects of an oxidative insult in isolated hearts. Several lab studies have reproducibly shown that CoQ10 administration facilitates post-ischemic functional recovery and improves myocardial integrity and metabolic status.

Glutathione S-Transferase (GST) and Gamma Glutamyl Cysteine Synthetase (γ-GCS)

Glutathiones play critical roles in intra- and extra-cellular defenses against oxidative damage, electrophiles and inflammatory responses. Glutathione S-transferase, GST, is a Phase II enzyme that catalyzes the S-conjugation of glutathione with reactive species such as electrophilic compounds. γ-GCSs are also involved in glutathione reactions in that γ-GCS is the rate limiting enzyme for glutathione synthesis. Therefore, regulation of γ-GCS is critical to maintain optimal cellular levels of glutathione.

GSTs are upregulated through an ARE site by chemoprotective compounds (Wasserman & Fahl (1997) Proc. Natl. Acad. Sci. U.S.A. 94:5361-5366) as well as antioxidants (Rushmore & Pickett (1990) 265: 14648-53).

Ferritin (Light and Heavy Chain)

The Ferritins are a distinct class of proteins that generally serve to protect the cell against reactive oxidative species. While iron (Fe) is vital to normal cellular function and survival, it must be well contained because it is able participate in the formation of potentially cytotoxic oxidative reactions. Ferritins are Fe chelators thereby providing a safe form of storage for the Fe in the cell.

It is an object of the present invention to provide a composition and method to protect cells from the potentially damaging effects of oxidative stress.

Another object of the present invention is to provide a composition and method to treat acute and/or chronic inflammation.

Yet another object of the present invention is to provide a method to identify compounds and biologic materials that can induce the expression of cytoprotective enzymes and other protective cell products.

It is a further object of the present invention to provide a method to identify compounds that inhibit VCAM-1 expression.

SUMMARY OF THE INVENTION

Unique sequences, designated CPREs (Cytoprotective Response Elements, see FIG. 6), have been identified that induce the coordinate activation of certain genes that protect cells from the potentially damaging effects of oxidative stress, and that do so, for example during conditions of hemodynamic shear stress. CPREs have the DNA consensus sequence 5'-RTGACWNAGCANW-3', wherein R=A or G, W=A or T, and N =A, G, C or T. The cellular functions of CPRE regulated genes are diverse, however in general, these genes act in various capacities to regulate and maintain redox homeostasis in the cell.

As a specific illustration of the invention, an in vitro model was established to study the effects of fluid shear stress on human aortic endothelial cell gene expression. Using this model many genes were identified whose expression is altered by different types of shear stress. Specifically genes whose expression is elevated by prolonged exposure to LSS (laminar shear stress) as compared to cells exposed to static culture or OSS (oscillatory shear stress) were examined that apparently allow the cell to discriminate between these different types of fluid shear stress. By using gene expression microarrays and DNA sequencing from subtractive libraries, the expression of numerous genes is significantly increased by exposure to LSS for 48 hrs (as compared to OSS or static culture). A subset of these genes is either known or is hypothesized to play a role in controlling the intracellular oxidative state of the cell and protecting cells from oxidative stress. When the DNA regulatory elements from the 5' regulatory regions of a subset of these genes (including heme oxygenase 1 (HO-1), glutathione-S-transferase (GST), quinone oxidoreductase 1 & 2 (NQO1, NQO2), Ferritin (heavy chain), Ferritin (light chain), gamma glutamyl cysteine synthase (γ-GCS)) were compared, a consensus sequence composed of 13 nucleotides (the CPRE, FIG. 6) became evident. The CPRE is unique, and different from the antioxidant response element (ARE) and the maf-recognition element (MARE).

It has been discovered that Nrf-2 acts as a transcriptional factor that activates CPRE. It was previously known that Keap-1 binds to Nrf-2 in the cytoplasm thereby preventing its translocation into the nucleus. It has been established that electrophilic agents release Nrf-2 from Keap-1 allowing for the translocation of Nrf-2 into the nucleus. The present invention shows for the first time that Nrf-2 can regulate gene expression in endothelial cells through the activation of CPRE. Furthermore, overexpression of Keap-1 inhibits the induction of the CPRE in endothelial cells. The present invention demonstrates that the transcription factor Nrf-2 induces, and the repressor protein Keap-1 inhibits, transcription from the CPRE thereby regulating CPRE-controlled genes in endothelial cells.

It has further been discovered that the expression of certain redox sensitive genes, such as those that are involved in the immune response (i.e., VCAM-1) are inhibited by CPRE-regulated genes. Thus therapeutic agents that increase the expression of CPRE-regulated genes inhibit inflammatory gene expression.

VCAM-1 is a particularly important modulator of inflammation. VCAM-1 is an inducible protein that is not expressed, or expressed at very low levels, in normal tissues. VCAM-1 is upregulated in a number of inflammatory diseases, including atherosclerosis, arthritis, asthma, dermatitis, psoriasis, cystic fibrosis, post transplantation late and chronic solid organ rejection, multiple sclerosis, systemic lupus erythematosis, inflammatory bowel diseases, autoimmune diabetes, diabetic retinopathy, diabetic nephropathy, rhinitis, ischemia-reperfusion injury, post-angioplasty restenosis, chronic obstructive pulmonary disease (COPD), glomerulonephritis, Graves disease, gastrointestinal allergies conjunctivitis, Kaposi's sarcoma, multiple sclerosis, as well as proliferative disorders of smooth muscle cells.

In a nonlimiting illustrative example, the CPRE was operably linked to the luciferase reporter gene and stably transfected into a HeLa cell line, which was thereafter treated with Compound A (known to have anti-inflammatory properties). Compound A activated the CPRE, as indicated by the expression of the luciferase reporter. In cell culture models, Compound A is known to inhibit the cell surface expression of VCAM-1 and have anti-inflammatory pathways in vivo.

In one embodiment, at least one copy of the CPRE is present in a nucleic acid construct. In another embodiment, at least one copy of CPRE is operably linked to a promoter. In a further embodiment, at least one copy of the CPRE is operably linked to a promoter, which is operably linked to a reporter gene. In an alternate embodiment, three copies of the CPRE are present in a nucleic acid construct, optionally with promoter genes and/or reporter genes. In a specific embodiment, the three copies of CPRE (3XCPRE) are selected from the following sequences: RTGACWNAG-CANWRTGACWNAGCANWRTGACWNAGCANW (SEQ. ID. NO 21); GTGACTCAGCAGAGTGACTCAG-CAGAGTGACTCAGCAGA (SEQ. ID. NO 22); GAGCTC-CAGTCACAGTGACTCAGCAGAATC-GAGCTCCAGTCACAGTGACT
CAGCAGAATCGAGCTCCAGTCACAGT-GACTCAGCAGAATC (SEQ. ID. NO.: 2). In a further embodiment, the 3XCPRE sequence is operably linked to a promoter, which is operably linked to a reporter gene. In other embodiments, 1, 2, 3, 4, 5, 6, 7, 8, 9 or 10 copies of CPRE can be present in a nucleic acid contruct, optionally operatively linked to one or more promoter genes and/or one or more reporter genes.

Based on these discoveries, the present invention includes at least the following aspects:

(1) A unique consensus sequence, the CPRE, that induces the coordinate induction of a set of shear stress regulated genes which provide protection against oxidative stress;

(2) A DNA construct that includes any of the cytoprotective response elements depicted in FIG. 6, including the consensus sequence operably linked to a heterologous protein coding sequence, (3) A DNA construct that includes a vector and the CPRE DNA sequence, (4) Cells and non-human organisms that include the cytoprotective response element, (5) A method for inducing the expression of a CPRE-containing gene that includes activating the CPRE or CPRE sequences via a transcriptional factor, upstream signal, chemical mediator, or physiological condition;

(6) A method of screening for a compound that increases transcription of an mRNA regulated by the CPRE or CPRE sequences, comprising the steps of:

(a) assaying a first cellular extract for the amount of transcription of the mRNA wherein the mRNA is expressed from a DNA construct, the transcription being in the absence of a candidate compound and the DNA construct comprising: a CPRE having a DNA sequence depicted in FIG. 6, for example, the consensus sequence in SEQ ID NO:1, operably linked to a protein coding sequence;

(b) assaying a second cellular extract for the amount of transcription of the mRNA wherein the mRNA is expressed from the DNA construct, the transcription being in the presence of the candidate compound; and (c) comparing the amounts of transcription of the first extract and the second extract, wherein a greater amount of transcription in the second extract as compared to the first extract indicates that the candidate compound increases transcription of the mRNA regulated by the CPRE.

(7) A method of screening for a compound that increases transcription of an mRNA regulated by a CPRE, comprising the steps of:

(a) assaying a first cellular extract for the amount of protein produced from an mRNA wherein the mRNA is expressed from a DNA construct, the expression being in the absence of a candidate compound and the DNA construct comprising: a CPRE having a DNA sequence depicted in FIG. 6, for example, the consensus sequence in SEQ ID NO:1, operably linked to a protein coding sequence;

(b) assaying a second cellular extract for the amount of protein produced from an mRNA wherein the mRNA is expressed from the DNA construct, the transcription being in the presence of the candidate compound; and (c) comparing the amounts of protein of the first extract and the second extract, wherein a greater amount of protein in the second extract as compared to the first extract indicates that the candidate compound increases transcription of the mRNA regulated by the CPRE.

(8) A method of identifying a transcription factor that binds to a CPRE having a DNA sequence depicted in FIG. 6, for example, the consensus sequence in SEQ ID NO:1, comprising: screening a mixture of cellular components for binding of a transcription factor to the CPRE and identifying a transcription factor which binds the CPRE.

(9) A purified transcription factor identified using the method of (8), and the use thereof to activate CPRE;

(10) A method for identifying compounds or biologic products that induce the expression of gene products regulated by the CPRE using methods described in detail herein;

(11) A method of identifying a transcriptional factor or transcriptional cofactor that binds to, or interferes with Nrf-2 activation of CPRE using methods described in detail herein;

(12) A method of identifying a compound or biologic product that inhibits the interaction of the transcription factor identified in (11) with Nrf-2 or inhibit the expression of such a transcription factor, using methods described in detail herein;

(13) The use of a compound to increase transcription of a mRNA regulated by a cytoprotective responsive element having the DNA sequence (CPREs). In a preferred embodiment, the compound is a small molecular weight compound that induces transcription from a CPRE or that binds to a CPRE transcription factor identified as described above.

(14) A method of treating a human being or an animal with an inflammatory disorder comprising administering an effective amount of a compound identified in (10).

(15) A method of identifying an upstream signaling factor that regulates the activity of a transcriptional factor that activates the CPRE that includes screening a mixture of cellular components for binding to a transcriptional factor as identified, for example in (8) and identifying a signaling factor that regulates the activity of a transcription factor which regulates the activity of the CPRE.

(16) CPRE-regulated gene products that are induced by shear stress or oxidative stress;

(17) A method to identify compounds that regulates the activity of Nrf-2 and induce transcription of CPRE;

(18) A method to identify compounds that regulates the activity of Keap-1 to allow for the translocation of Nrf-2 into the nucleus and induce transcription of CPRE; and

(19) A method to inhibit the expression of VCAM-1 or another redox-sensitive gene product comprising administering a compound that activates the CPRE.

(20) The use of 1,3-bis-(substituted-phenyl)-2-propen-1-ones (chalcones) and similar compounds to activate CPRE, and thus induce the expression of a cytoprotective enzyme or the coordinate induction of such enzymes. In a specific embodiment, the compound is 3-(5-benzo-[b]-thiophene-2-yl-2,4-dimethoxy-phenyl)-1-(3,4,5-tri-methoxyphenyl)-propenone (Compound A).

BRIEF DESCRIPTION OF FIGURES

FIG. 5 is a bar graph showing the effect of laminar shear stress (LSS) (20 dynes/cm2) on the levels (measured as cpm of CAT activity) of the NQO1 promoter, NQO1/CAT and on a NQO1 promoter construct containing a deletion of the CPRE. Deletion of CPRE prevented the ability of LSS to significantly increase NQO1/CAT promoter levels.

FIG. 6 shows the DNA sequence alignment of CPREs from the shear stress-regulated genes, NQO1, NQO2, mFerritin (H), hFerritin(H), mFerritin(L), HO-1, mGST and γ-GCE, along with additional CPRE sequences. The consensus sequence: 5'RTGACWNAGCANW3' (SEQ ID NO:1), as well as SEQ ID NOS. 3-20, are also shown.

(SEQ ID NO:2)
GAGCTCCAGTCACAGTGACTCAGCAGAATCGAGCTCCAGTCACAGTGACT

CAGCAGAATCGAGCTCCAGTCACAGTGACTCAGCAGAATC.

Figure 8:
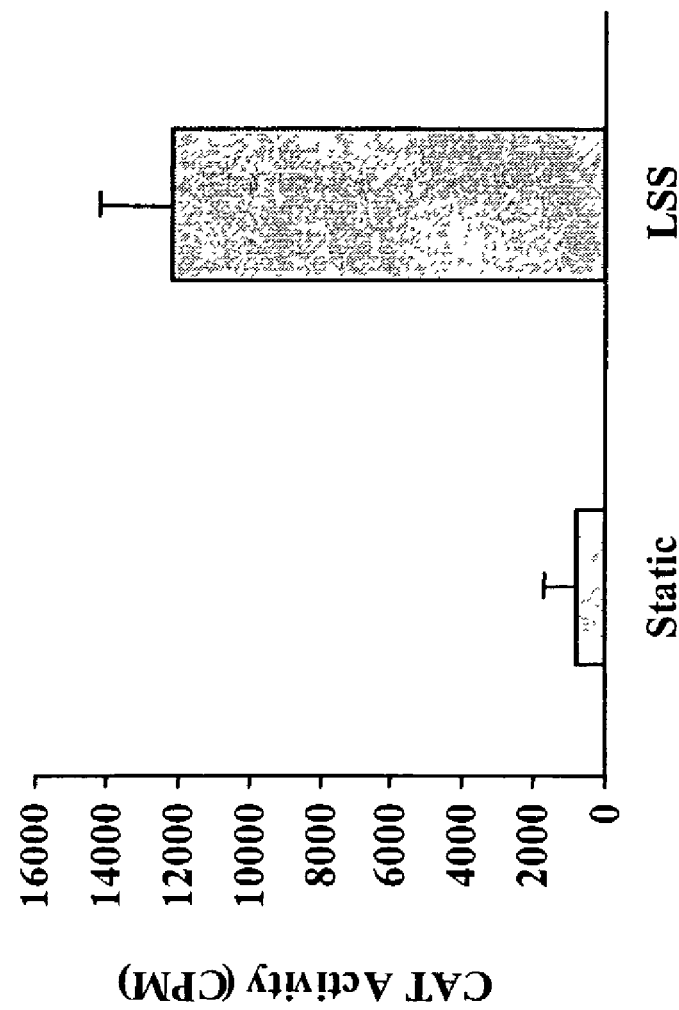

FIG. 8 is a bar graph showing the effect of laminar shear stress (LSS) (20 dynes/cm2) on p3xCPRE activity (measured as cpm of CAT activity) in human microvascular endothelial cells. LSS significantly increased the activity of the CPRE promoter.

Figure 9A:
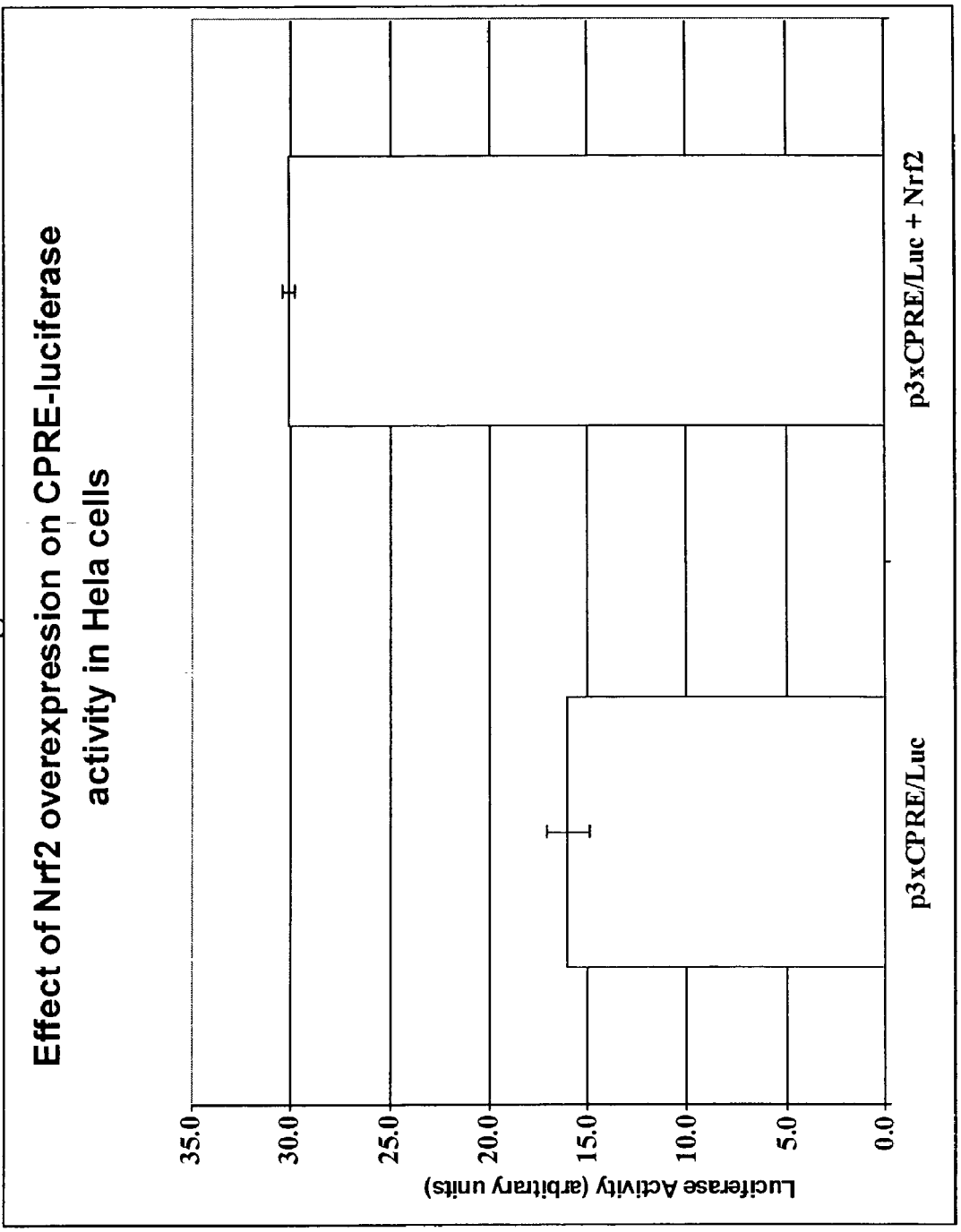
Figure 9B:
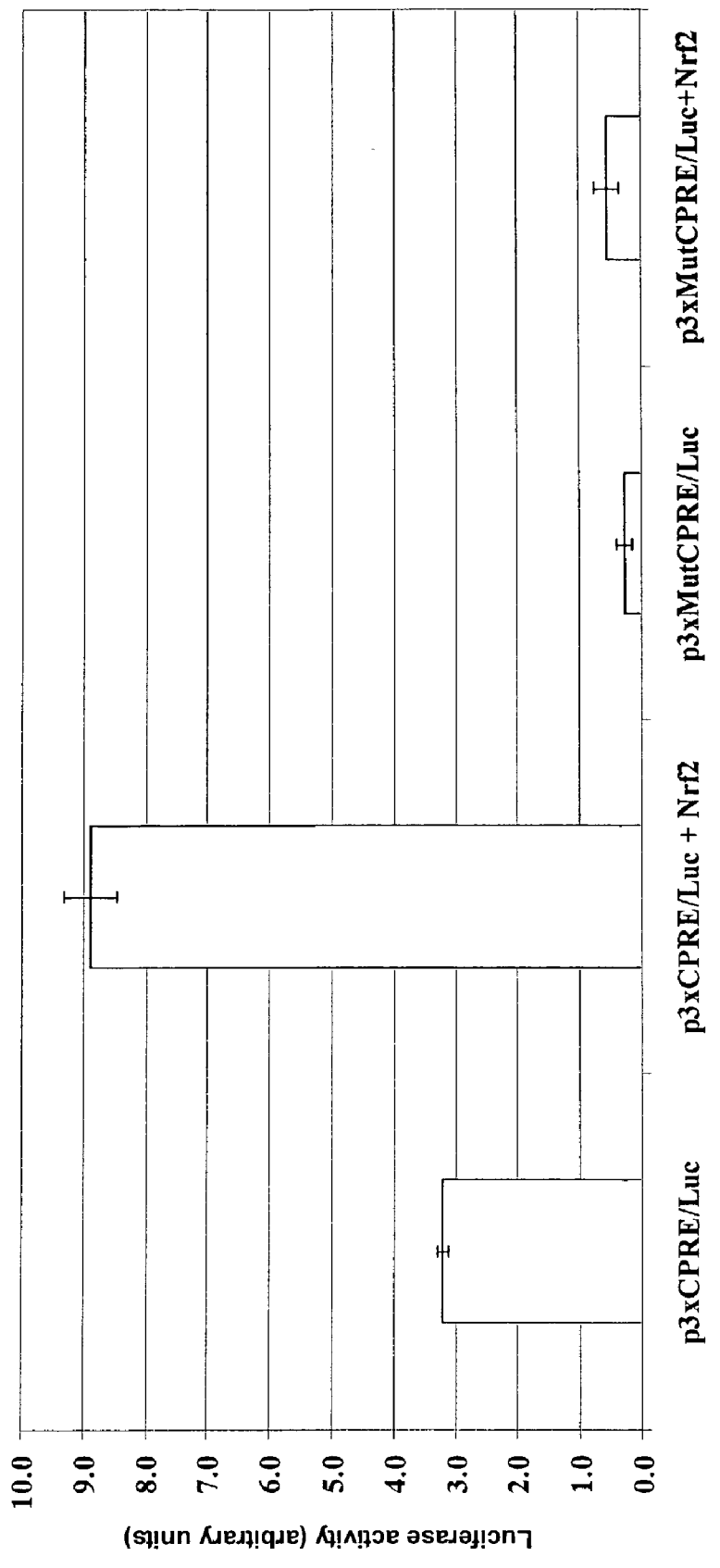

FIG. 9a is a bar graph showing the effect of Nrf-2 overexpression on CPRE-luciferase activity (p3xCPRE/Luc) in cultured Hela cells transfected with p3xCPRE/Luc. Nrf-2 caused a significant elevation of the activity of the p3xCPRE/Luc in the Hela cells. FIG. 9b is a bar graph showing the effect of Nrf-2 overexpression on CPRE activity in cultured HMEC cells transfected with either p3xCPRE/Luc or a construct containing a mutation in the CPRE (p3xMutCPRE/Luc, p3xMutCPRE/Luc+Nrf-2). The left-most bars show that Nrf-2 overexpression caused a significant elevation of the activity of the p3xCPRE/Luc in the HMEC cells. The right-most bars show that the CPRE mutation prevented the Nrf-2-induced elevation of the activity of the p3xMutCPRE/Luc. FIG. 9c is a bar graph showing the effect of Keap overexpression and compound A on the activity of CPRE-luciferase (p3xCPRE/Luc) in cultured Hela cells transfected with p3xCPRE/Luc. The left-most bars show that Keap overexpression caused a significant reduction of the activity of the p3xCPRE/Luc in the Hela cells. The second bar from the right shows that compound A (15 µM) significantly increased the activity of the p3xCPRE/Luc in the Hela cells. The right-most bar shows that Keap overexpression was able to significantly inhibit the Compound A-induced elevation of the activity of the p3xCPRE/Luc.

Figure 10:
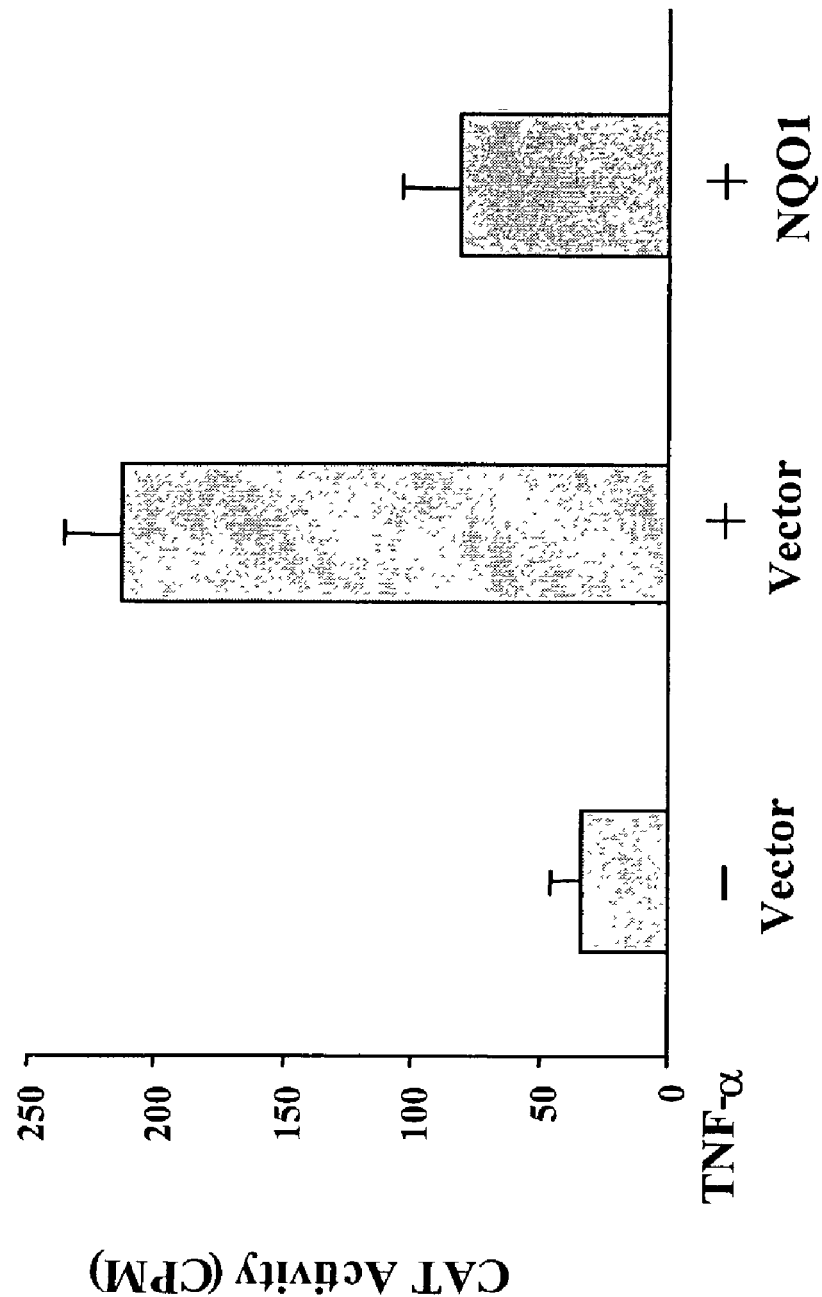

FIG. 10 is a bar graph showing the effect of overexpression of NQO1 on TNF-α-activated VCAM-1 gene expression (measured as cpm of CAT activity) in cultured endothelial cells. The presence of TNF-α significantly elevated VCAM-1 gene expression (middle bar). The addition of NQO1 prevented this increase in VCAM-1 gene expression (right bar).

Figure 11:
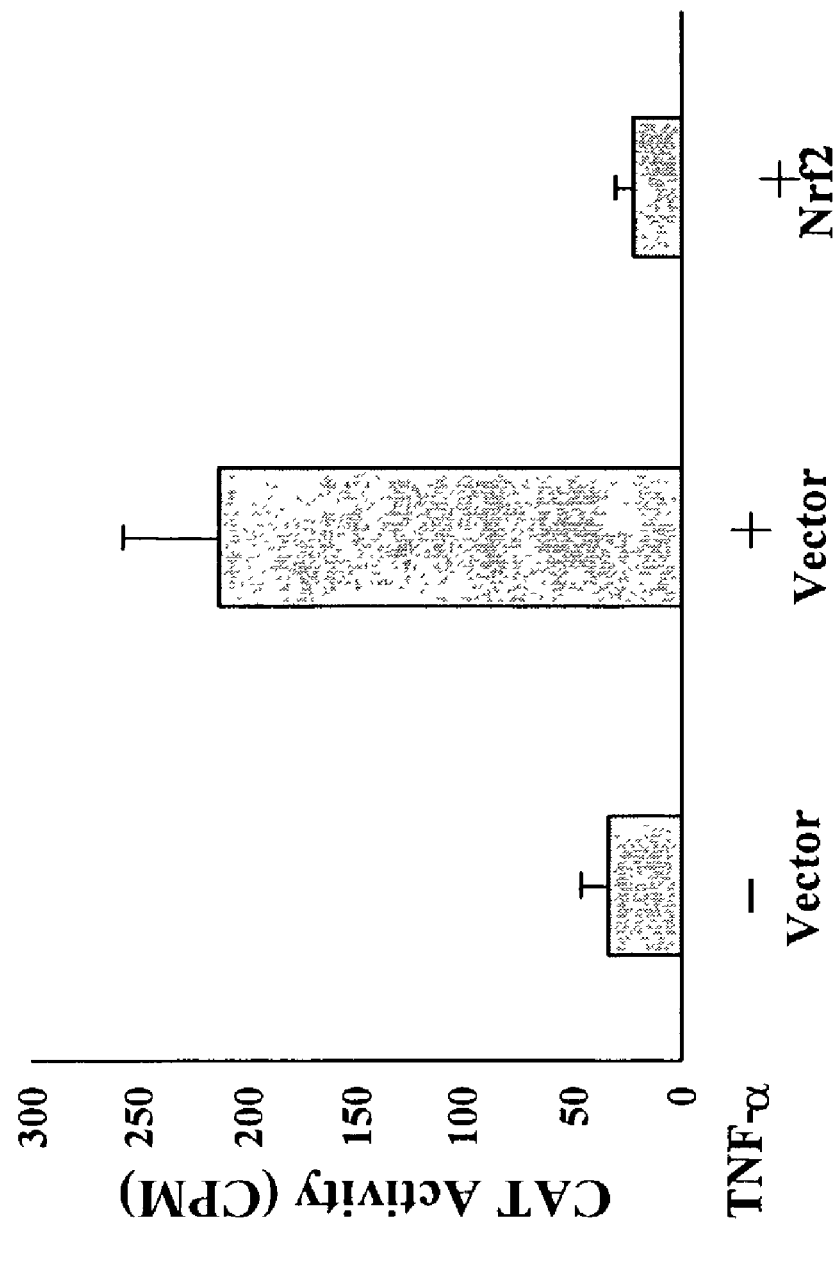

FIG. 11 is a bar graph depicting the effect of the expression of Nrf-2 in cultured endothelial cells on TNF-α-activated VCAM-1 gene expression (measured as cpm of CAT activity). The presence of TNF-α significantly elevated VCAM-1 gene expression (middle bar). Nrf-2 expression prevented this increase in VCAM-1 gene expression (right bar).

Figure 12A:
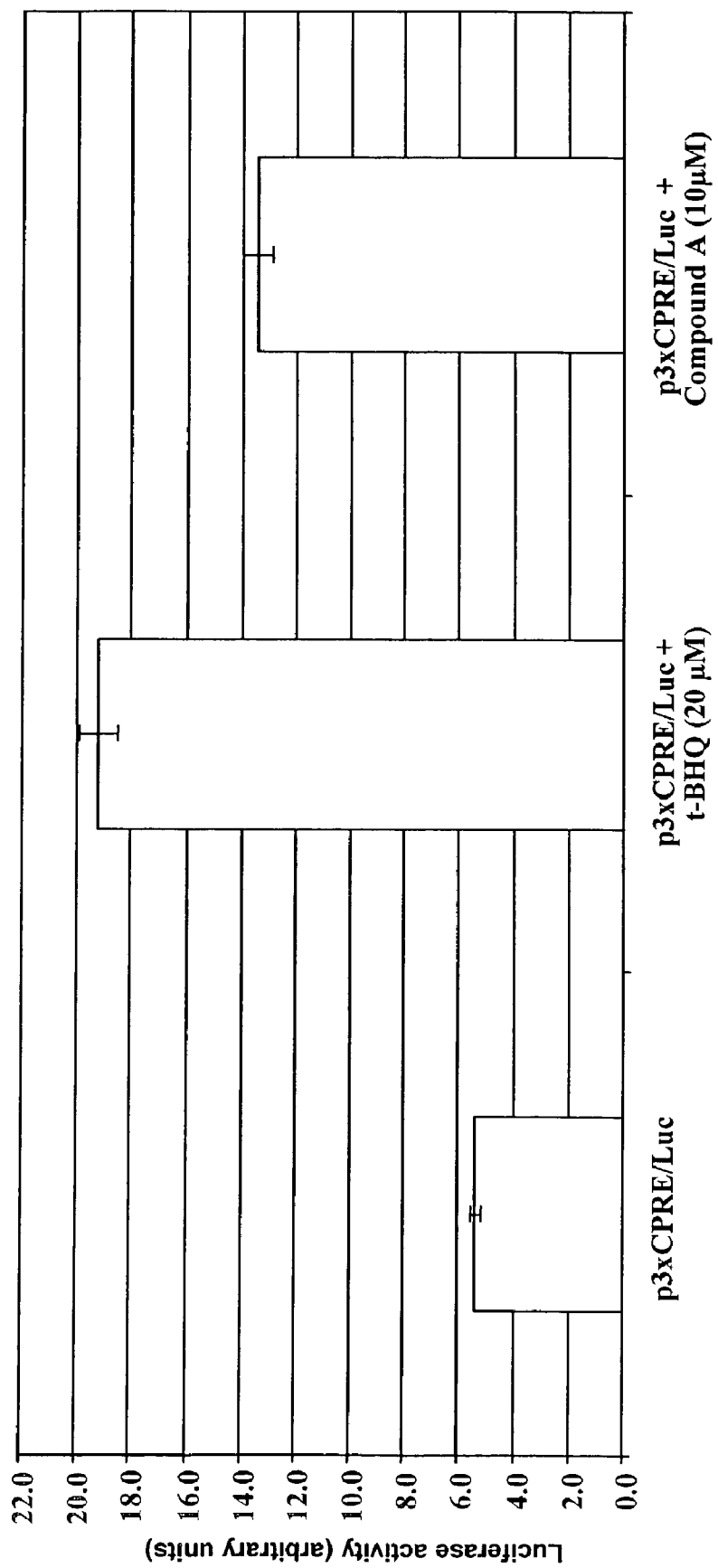
Figure 12B:
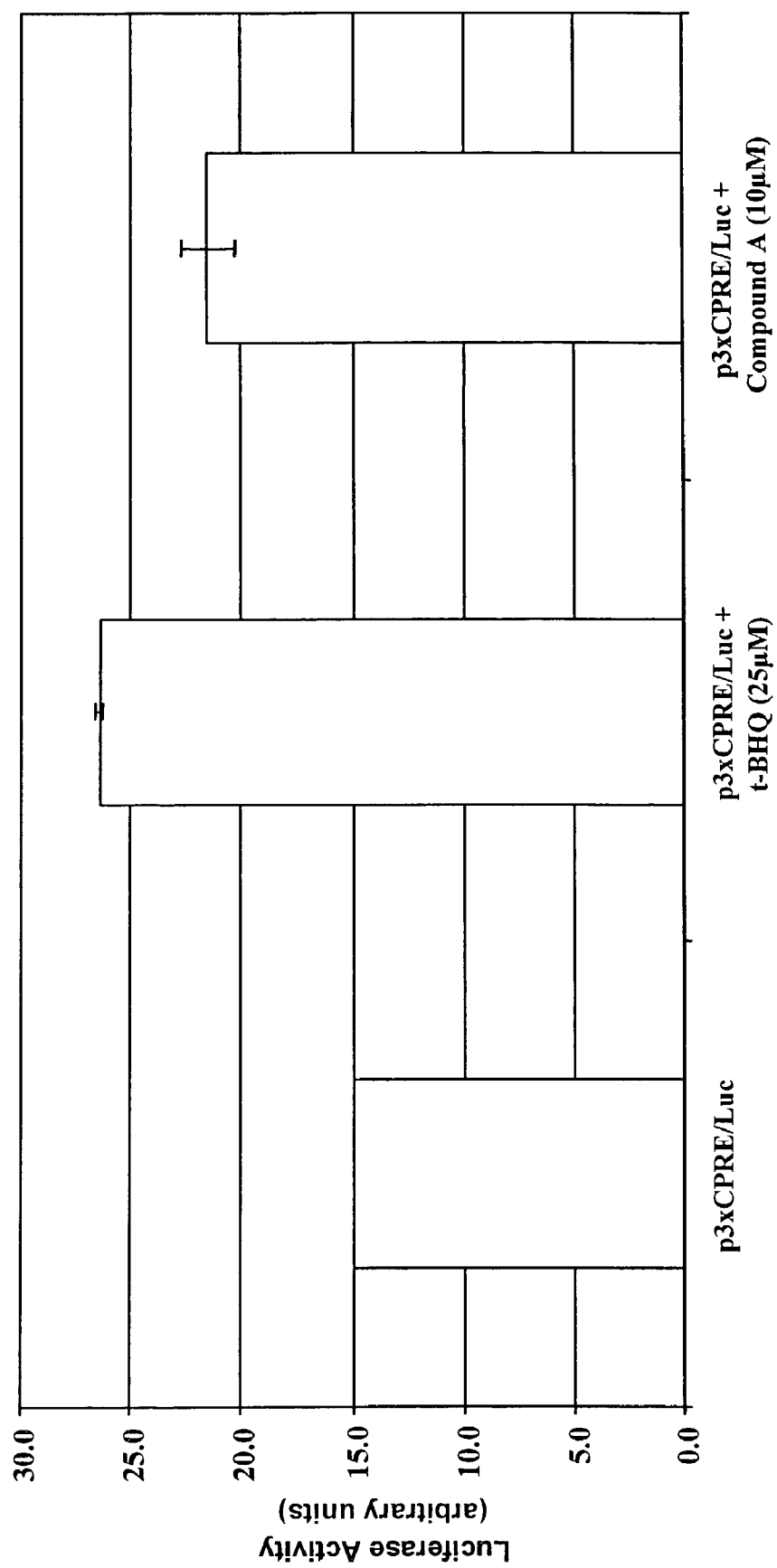

FIG. 12a is a bar graph showing the effect of t-BHQ and Compound A on CPRE-luciferase (p3xCPRE/Luc) activity in cultured HMEC cells transfected with p3xCPRE/Luc. The bars show that t-BHQ (20 µM) significantly increased p3xCPRE/Luc activity. Compound A (10 µM) also significantly increased p3xCPRE/Luc activity. FIG. 12b is a bar graph showing the effect of t-BHQ and compound A on CPRE-luciferase (p3xCPRE/Luc) activity in cultured Hela cells transfected with p3xCPRE/Luc. The bars show that t-BHQ (25 µM) significantly increased p3xCPRE/Luc activity. Compound A (10 µM) also significantly increased p3xCPRE/Luc activity the Hela cells.

Figure 13:
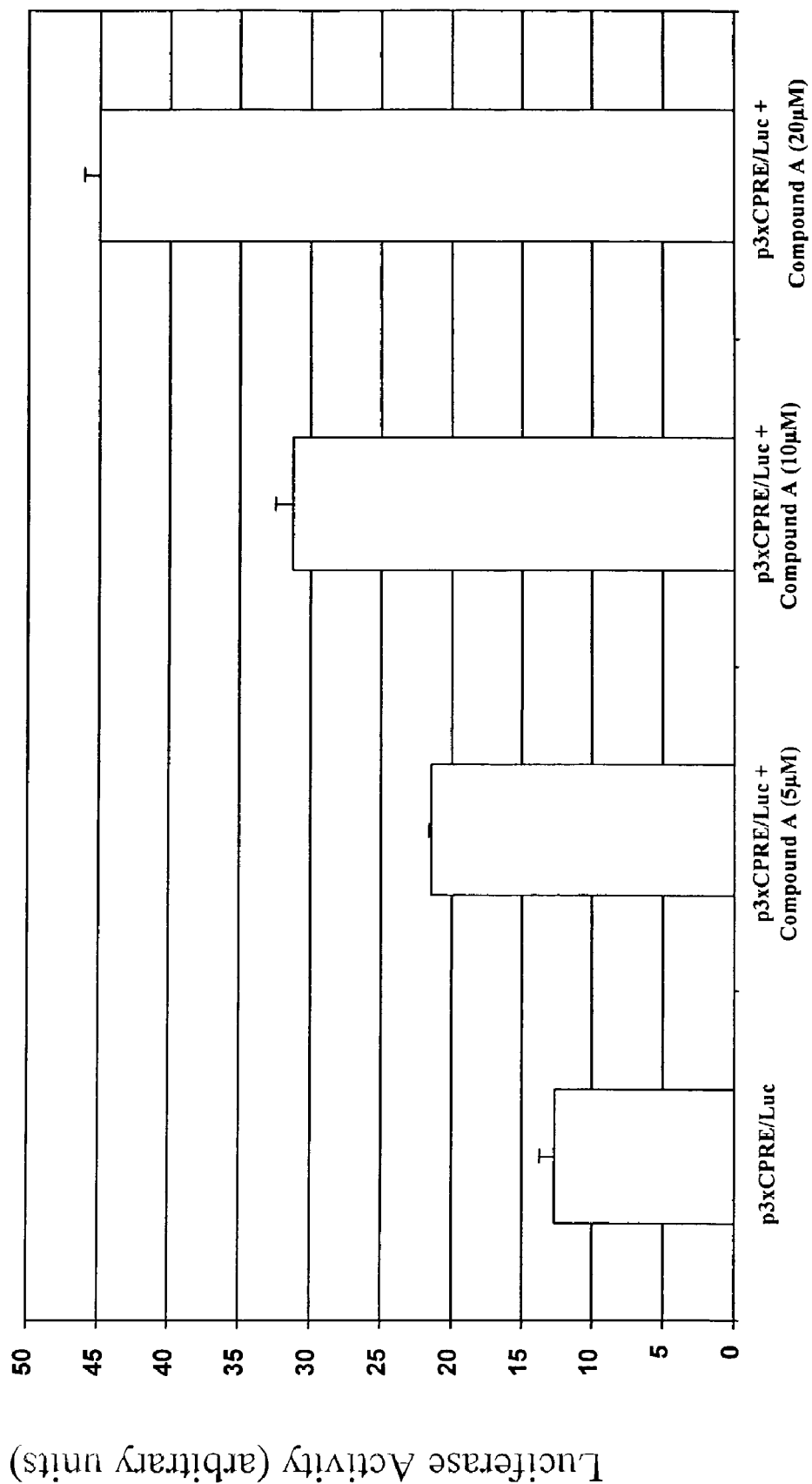

FIG. 13 is a bar graph depicting the concentration-response relationship of Compound A (5, 10 and 20 µM) on CPRE-luciferase (p3xCPRE/Luc) activity in cultured Hela cells. Increasing concentrations of compound A significantly increased the p3xCPRE/Luc activity in these cells in a concentration-dependent manner.

Figure 14:
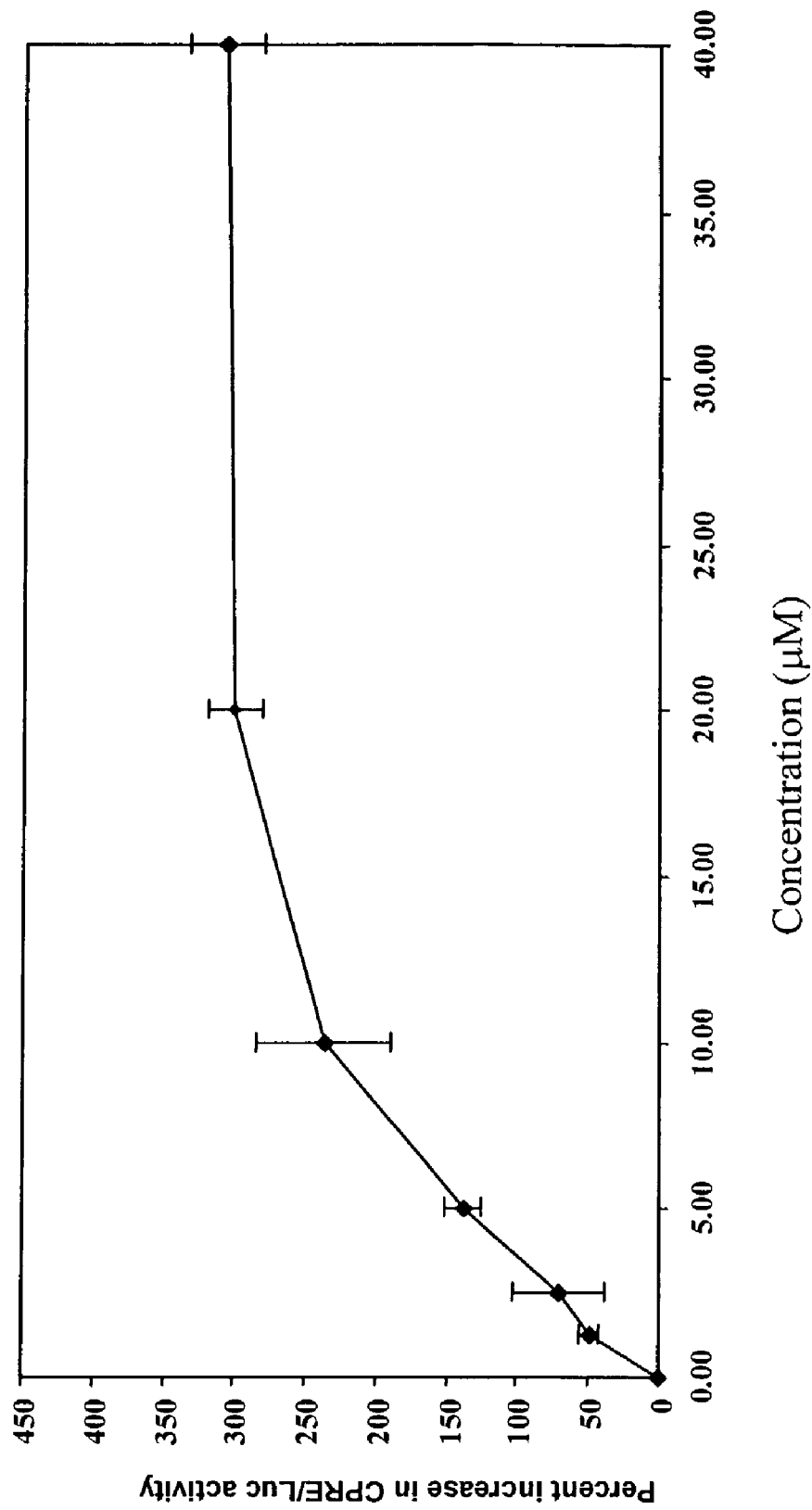

FIG. 14 is a line graph depicting the concentration-response relationship of Compound A (1.25, 2.5, 5, 10, 20 and 40 µM) on CPRE-luciferase (p3xCPRE/Luc) activity in cultured Hela cells transfected with p3xCPRE/Luc. CPRE/Luc activity is measured as the percent increase over control (vehicle) levels. The activity of CPRE/Luc is significantly elevated in a concentration-dependent manner by compound A.

Figure 15:
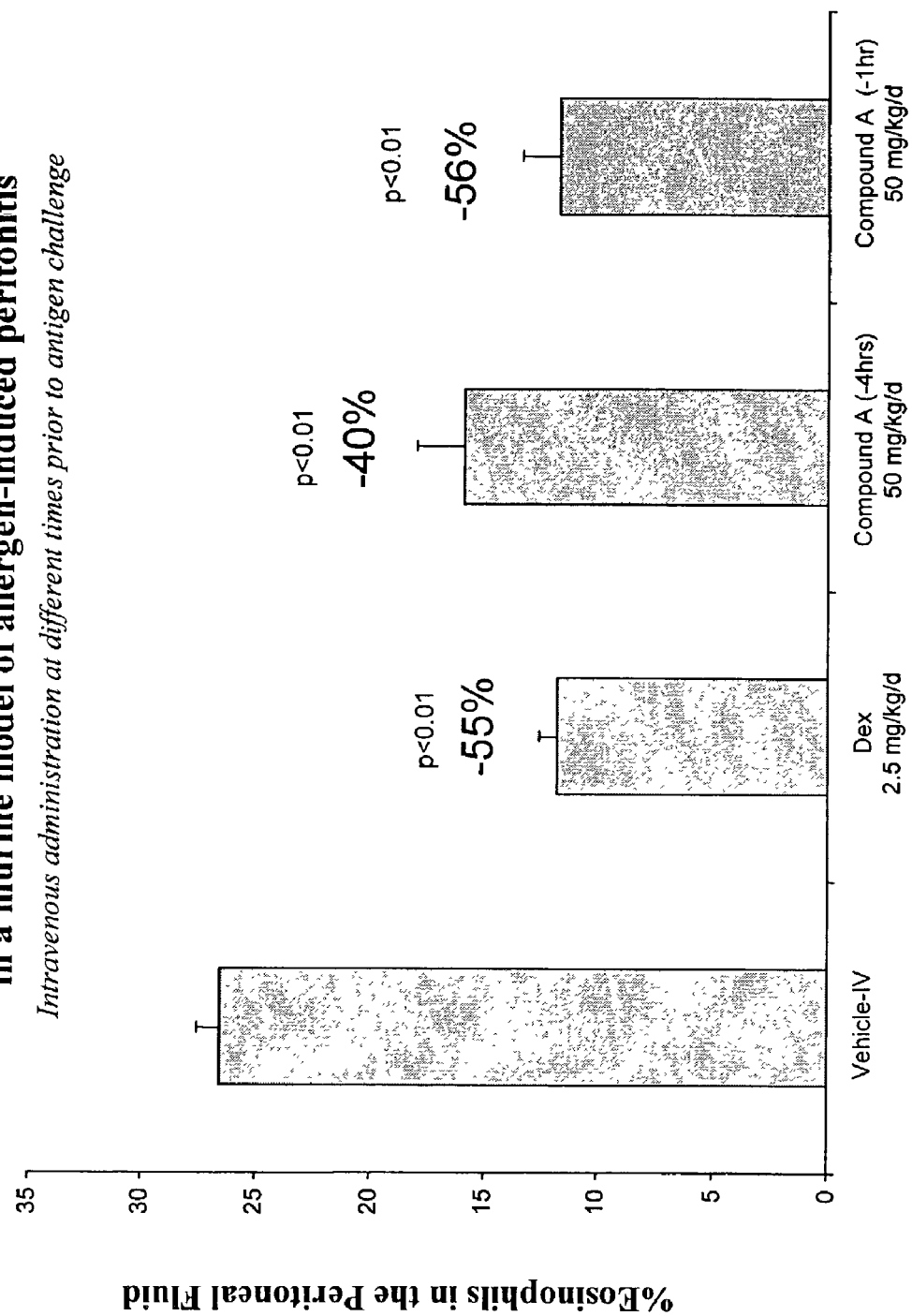

FIG. 15 is a bar graph depicting the effect of intravenously administered Compound A (50 mg/kg/d) on eosinophil recruitment (measured as the percent eosinophils in a sample of peritoneal fluid) in a murine model of allergen-induced peritonitis. Compound A was administered at either 1 or 4 hours prior to antigen challenge with ovalbumin. Control animals received either vehicle alone or Dexamethasone-Ova (2.5 gm/kg/d). The results show that Dexamethasone and Compound A (at both 1 and 4 hrs pre-treatment) significantly decreased eosinophil levels measured in the peritoneal fluid of antigen-challenged mice.

Figure 16:
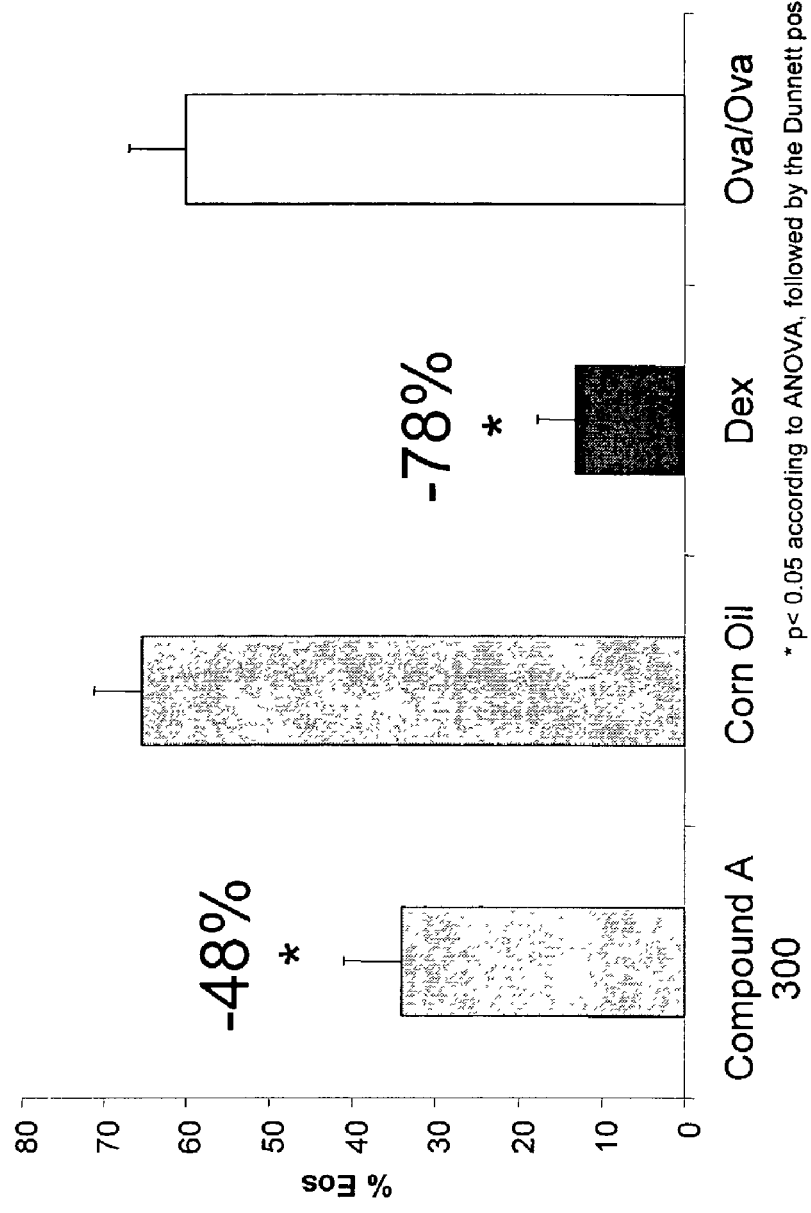

FIG. 16 is a bar graph depicting the effect of orally administered Compound A (300 mg/kg/d) on eosinophil recruitment (measured as the percent eosinophils in a sample of bronchoaveolar lavage fluid) in a murine model of aerosolized ovalbumin-induced asthma. Control animals received either vehicle alone or Dexamethasone (3 gm/kg/d). The results show that Dexamethasone and Compound A significantly decreased eosinophil levels measured in the bronchoaveolar lavage fluid of antigen-challenged mice.

Figure 17:
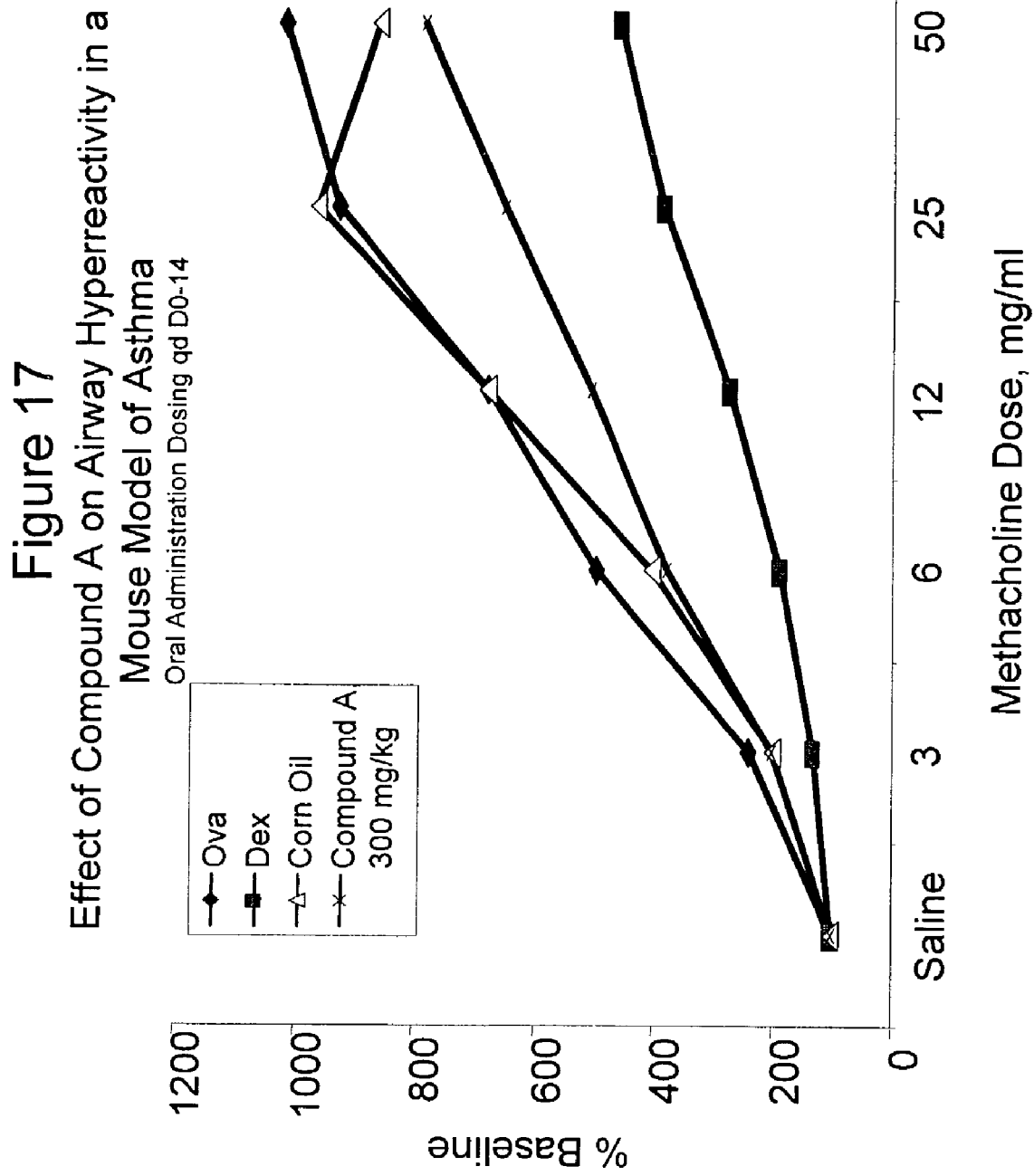

FIG. 17 is a line graph depicting the effect of orally administered Compound A (300 mg/kg/d) on lung function (decreased airway hyperreactivity to methacholine) in a murine model of aerosolized ovalbumin-induced asthma. Control animals received either vehicle alone or Dexamethasone (3 gm/kg/d). The results show that Dexamethasone and Compound A significantly improved lung function (decreased airway hyperreactivity to methacholine).

Figure 18:
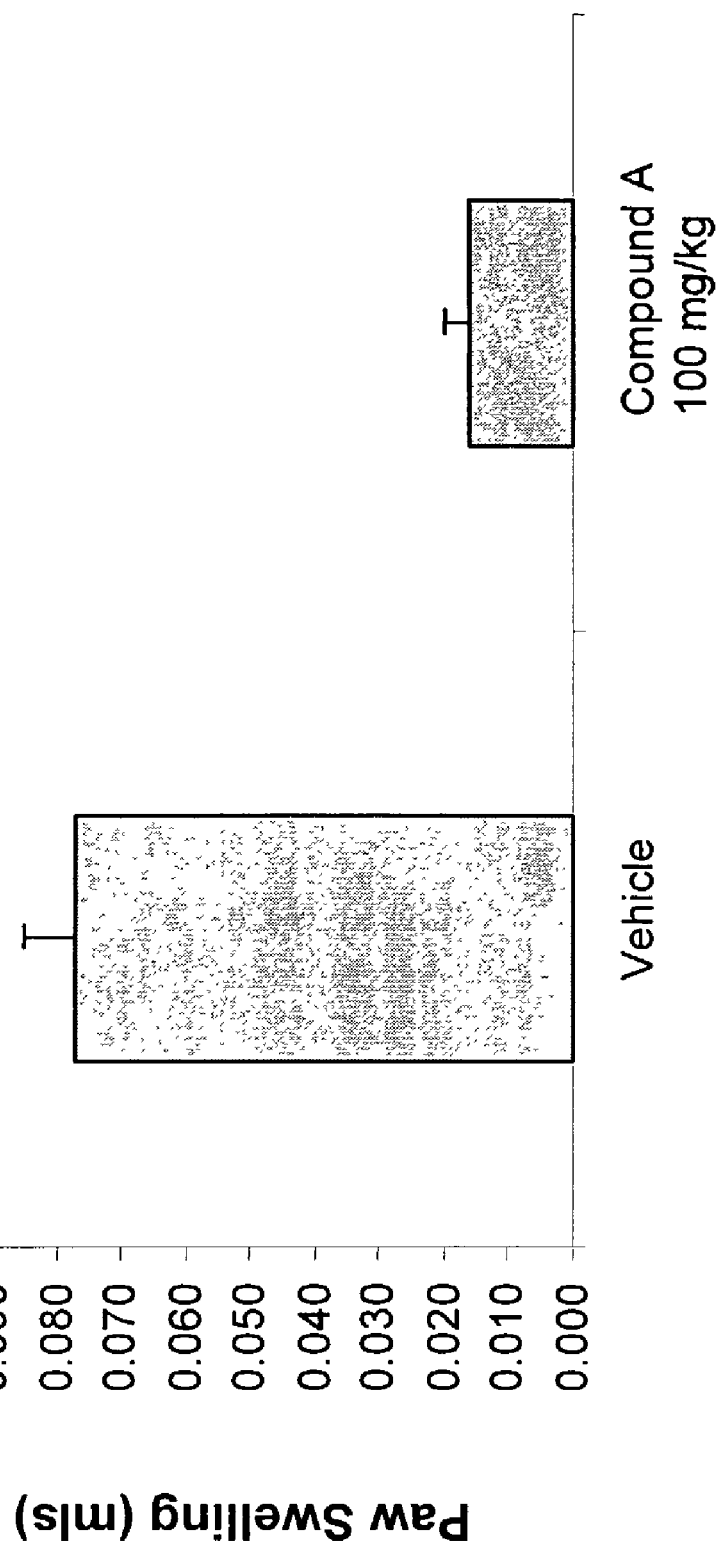

FIG. 18 is a bar graph depicting the effect of intraperitoneal administered Compound A (100 mg/kg/d) in a methylated BSA-induced model of delayed type hypersensitivity—a generalized model for inflammation accompanied by edema. Compound A was administered at either −24, −1 or +6 hrs hours from the time of antigenchallenged mice.

Figure 19:
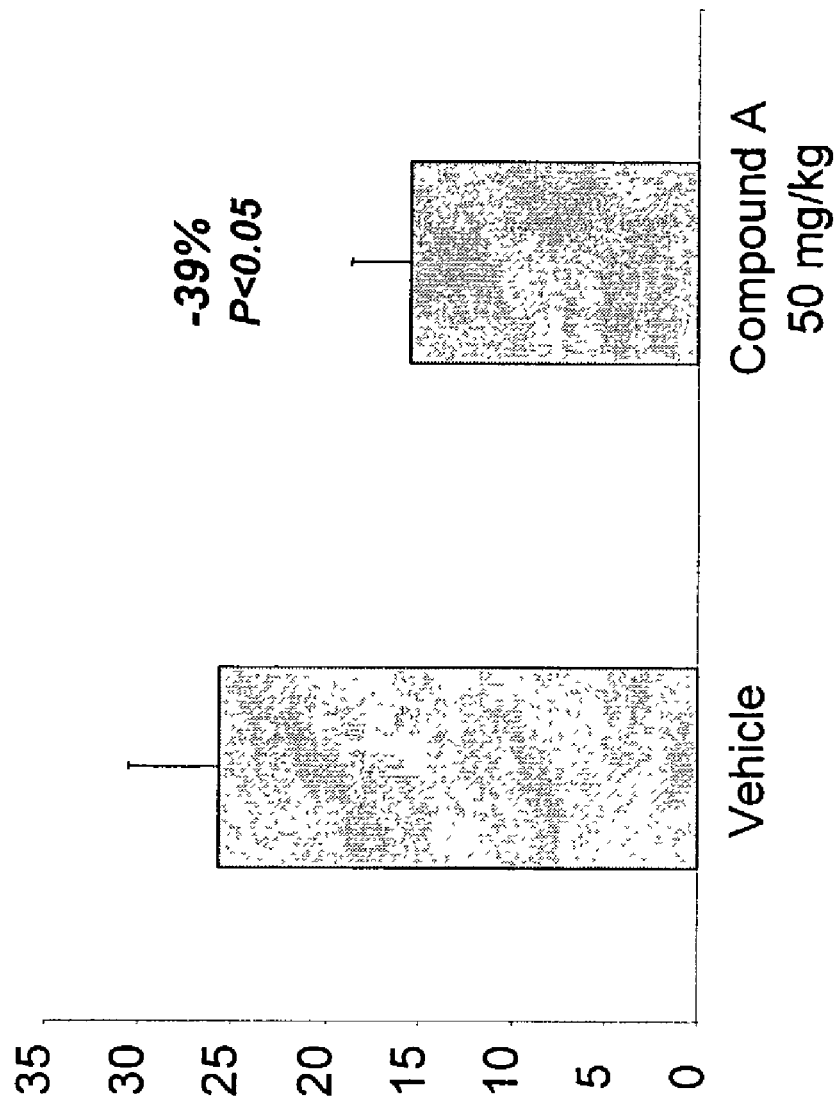

FIG. 19 is a bar graph depicting the effect of intravenously administered Compound G (50 mg/kg/d) on eosinophil recruitment (measured as the percent eosinophils in a sample of peritoneal fluid) in a murine model of allergen-induced peritonitis. The results show that Compound G significantly decreased eosinophil levels measured in the peritoneal fluid of antigen-challenged mice.

DETAILED DESCRIPTION OF THE INVENTION

This invention describes a cytoprotective response element, which can be any of those sequences shown in FIG. 6, which includes a consensus sequence (5'RTGACWNAG-CANW3'(SEQ ID NO:1)). In another embodiment a DNA construct is provided that includes the cytoprotective response element operably linked to a heterologous protein coding sequence, a DNA molecule that includes a vector and the DNA construct, cells and non-human organisms that include the cytoprotective response element, and a method for screening for a compound that increases mRNA regulated by a cytoprotective response element. It has been discovered that the cytoprotective response element induces the coordinate activation of certain genes that protect cells from the potentially damaging effects of oxidative stress, and that it does so, for example during conditions of hemodynamic steady laminar shear stress. Furthermore, it has been discovered that activation of such protective genes (such as NQO1) inhibits TNF-α-induced, redox-sensitive proinflammatory genes such as VCAM-1.

The invention is based on discoveries that provide a more thorough understanding of the cellular mechanisms that are involved in protecting cells from the harmful effects of oxidative stress. The present invention identifies a group of genes that are involved in this type of cellular protection. Furthermore, assays have been developed using these discoveries which identify pharmacological and biological compounds that activate these protective genes. Most importantly, compounds that are identified using the information provided herein can activate antioxidative-protective genes and can thus be utilized to treat inflammatory disorders. The invention discloses a coordinate set of genes that together can account for an anti-inflammatory phenotype exhibited by endothelial cells.

The increased expression of CPRE-regulated genes in response to LSS and oxidative stress signals, via regulatory elements in and around the CPRE region, is a compensatory response that serves to protect the cell from the potential damaging effects of oxidant stress. Since the cellular redox state has been implicated in the pathogenesis of inflammatory disease and plays a direct role in redox-sensitive inflammatory gene expression, identification of pharmaceutical agents that mediate the coordinate induction of CPRE-containing genes provides a beneficial therapeutic effect on disease processes that involve oxidant-mediated pathways including inflammatory conditions.

To identify compounds that will induce the expression of CPRE containing genes, the invention further discloses methods to identify active compounds. Therefore, the invention provides a DNA construct comprising a cytoprotective response element (CPRE) having a DNA consensus sequence depicted in FIG. 6, for example, 5'RTGACWNAGCANW3' (SEQ ID NO:1), operably linked to a heterologous protein coding sequence. The invention also provides a recombinant DNA molecule comprising a vector and the above-described DNA sequence. The invention further provides a cell or non-human organism comprising the above-described DNA construct.

I. Definitions

In the description that follows, a number of terms used in recombinant DNA (rDNA) technology are used. In order to provide a clear and consistent understanding of the specification and claims, including the scope to be given such terms, the following definitions are provided.

Gene. A nucleic acid sequence related to a single polypeptide chain or protein, and as used herein includes 5' and 3' untranslated ends. The polypeptide can be encoded by a full-length sequence or any portion of the coding sequence, so long as the functional activity of the protein is retained.

Complementary DNA (cDNA). Recombinant nucleic acid molecules synthesized by reverse transcription of messenger RNA ("mRNA").

Structural Gene. A DNA sequence that is transcribed into mRNA that is then translated into a sequence of amino acids characteristic of a specific polypeptide.

Protein Coding Sequence. A nucleic acid sequence that encodes a protein or polypeptide.

Protein Complex. Two or more proteins bound together by covalent or noncovalent linkage or a protein and another compound (ex. an inducer or drug).

Reporter Gene. A gene encoding a protein that is easily assayed, wherein the assay provides a quantitative measure of the amount of protein (gene product) present. A first example of a useful reporter gene that can be used in a DNA construct according to the invention is the firefly luciferase gene. The protein encoded by this gene catalyzes a reaction that produces light as one of its reaction products. The amount of light emitted can be easily quantitated and correlates with the amount of luciferase protein present. Another useful reporter gene is the chloramphenicol acetyltransferase (CAT) gene. The resection products of the CAT enzyme can be conveniently assayed to provide a quantitative measure of the amount of CAT present. Other convenient reporter genes will be known to a person skilled in the art.

Vector. A plasmid, phage, or virus DNA or other DNA sequence into which DNA can be inserted to be cloned. The vector can replicate autonomously in a host cell, and can, in some cases, be further characterized by one or a small number of endonuclease recognition sites at which such DNA sequences can be cut in a determinable fashion and into which other DNA can be inserted. The vector can further comprise a marker suitable for use in the identification of cells transformed with the vector. Makers, for example, are tetracycline resistance, ampicillin resistance and G418 resistance. The words "cloning vehicle" are sometimes used for "vector."

Construct: A vector into which a DNA sequence has been inserted.

Expression. Expression is the process by which a structural gene produces a polypeptide. It involves transcription of the gene into mRNA, and the translation of such mRNA into polypeptide(s).

Expression Vector. A vector or vehicle similar to a cloning vector but which is capable of expressing a gene which has been cloned into it, after transformation into a host. The cloned gene is usually placed under the control of (i.e., operably linked to) certain control sequences such as promoter sequences.

Expression control sequences will vary depending on whether the vector is designed to express the operably linked gene in a prokaryotic or eukaryotic host and can additionally comprise transcriptional elements such as enhancer elements, termination sequences, tissue-specificity elements, and/or translational initiation and termination sites.

Nucleic Acid Hybridization. Nucleic acid hybridization depends on the principle that two single-stranded nucleic acid molecules that have complementary base sequences will reform the thermodynamically favored double-stranded structure if they are mixed under the proper conditions. The double-stranded structure will be formed between two complementary single-stranded nucleic acids even if one is immobilized on a nitrocellulose filter. In the Southern hybridization procedure, the latter situation occurs. The DNA of the individual to be tested is digested with a restriction endonuclease, fractionated by agarose gel electrophoresis, converted to the single-stranded form, and transferred to nitrocellulose membrane, making it available for annealing to a hybridization probe.

Polyacrylamide Gel Electrophoresis (PAGE). The most commonly used technique (though not the only one) for achieving a fractionation of polypeptides on the basis of size is polyacrylamide gel electrophoresis. The principle of this method is that polypeptide molecules migrate through the gel as though it were a sieve that retards the movement of the largest molecules to the greatest extent and the movement of the smallest molecules to the least extent. Note that the smaller the polypeptide fragment, the greater the mobility under electrophoresis in the polyacrylamide gel. Both before and during electrophoresis, the polypeptides typically are continuously exposed to the detergent sodium dodecyl sulfate (SDS), under which conditions the polypeptides are denatured. Native gels are run in the absence of SDS. The polypeptides fractionated by polyacrylamide gel electrophoresis can be visualized directly by a staining procedure.

Western Transfer Procedure. The purpose of the western transfer procedure (also referred to as immunoblotting) is to physically transfer polypeptides fractionated by polyacrylamide gel electrophoresis onto a nitrocellulose filter or another appropriate surface, while retaining the relative positions of polypeptides resulting from the fractionation procedure. The blot is then probed with an antibody that specifically binds to the polypeptide(s) of interest.

Purified. A "purified" protein or nucleic acid is a protein or nucleic acid that has been separated from a cellular component. "Purified" proteins or nucleic acids have been purified to a level of purity not found in nature.

Substantially Pure. A "substantially pure" protein or nucleic acid is a protein or nucleic acid preparation that contain only other components that do not materially affect the properties of the nucleic acid or protein.

Induction of expression of a particular coding sequence or gene by a compound. Such induction can occur according to one or more of a number of different mechanisms, as are known to persons skilled in the art:
1. The compound can bind directly to a cis-acting regulatory element (preferably, the cis-acting regulatory element described herein is a CPRE) of the gene, causing an increase in transcription of the gene.
2. The compound can bind to a transcription factor (protein or protein complex) that is already present in the cell in an inactive form, thus activating or depressing it. The depressed transcription factor can then be able to bind, generally with the compound, to a cis-acting regulatory element of the gene, consequently increasing transcription.
3. The compound can bind an inhibitor of the gene, rendering the inhibitor ineffective. For example, the inhibitor can be bound to a cis-acting repressor element of the gene, and binding of the compound to the inhibitor causes it to be released from the repressor element.
4. The compound can stabilize mRNA transcribed from the gene against degradation by the cellular machinery, thus lengthening its persistence in the cell and increasing the number of times it can be translated to protein.
5. The compound can cause increased synthesis of a transcription factor that positively regulates the gene. This can occur by any of mechanisms 1-4 operating on a second gene that encodes the transcription factor. Increased abundance of the transcription factor results in increased expression of the first gene, on which it acts.

The following abbreviations are used in this specification: A is adenine, G is guanine, T is thymine, C is cytosine, U is uracil, R is adenine or guanine, Y is cytosine or thymine, M is cytosine or adenine, W is adenine or thymine, and N is any of A, C, G, or T.

II. Cytoprotective Responsive Element (CPRE)

In one embodiment, the present invention is a cytoprotective responsive element (CPRE) depicted in FIG. 6, which includes the DNA consensus sequence 5'-RTGACWNAGCANW-3' (SEQ ID NO:1).

In another embodiment, the invention is the sequence 5'-RTGACWNAGCANW-3' (SEQ ID NO 1) in isolated or substantially pure form. In another embodiment, the present invention is a CPRE sequence selected from the group consisting of those sequences set forth in FIG. 6 in substantially pure or isolated form. In one preferred embodiment, the present invention is a CPRE consisting essentially of one of the above described sequences.

Figure 7:
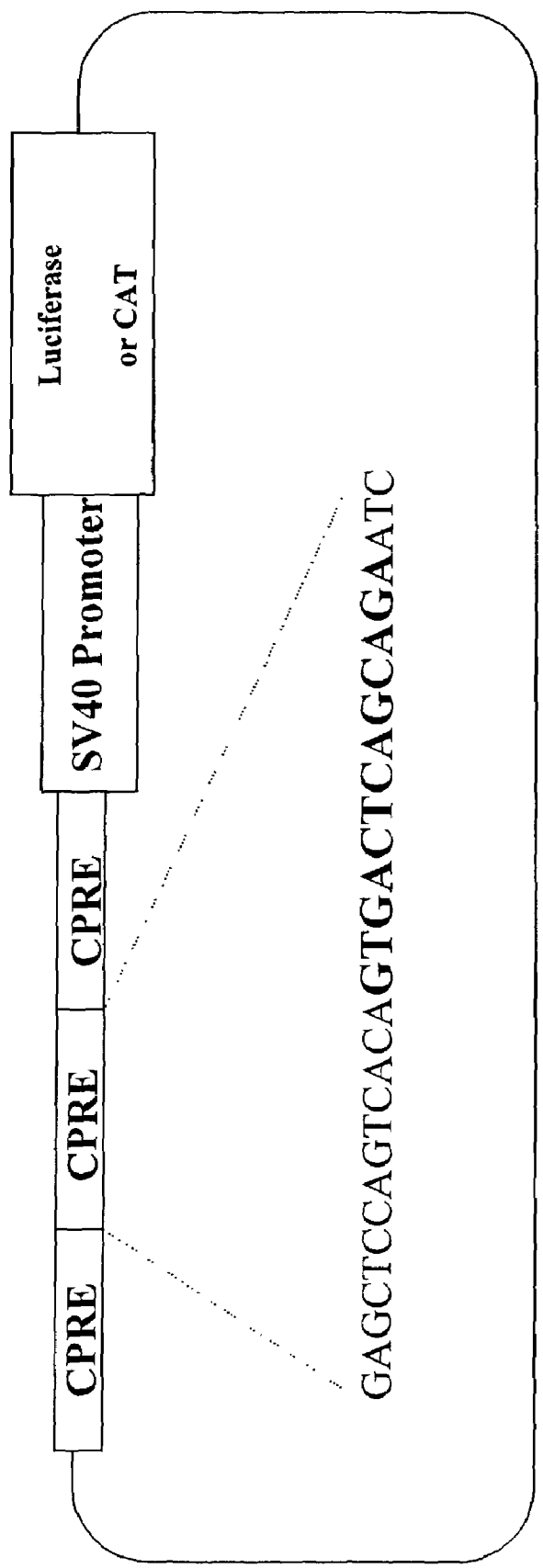
FIG. 7 depicts a diagram of the p3xCPRE, the SV40 Promoter and the luciferase or CAT reporter gene construct. The diagram shows a construct containing 3 copies of the NQO1 CPRE gene (in bold), the additional nucleotides depicted are nucleotides that are present 5' and 3' of the native NQO1 CPRE gene. The full 3xCPRE sequence is represented by the nucleotides.

In one embodiment, at least one copy of the CPRE is present in a nucleic acid construct. In another embodiment, at least one copy of CPRE is operably linked to a promoter. In a further embodiment, at least one copy of the CPRE is operably linked to a promoter, which is operably linked to a reporter gene. . In other embodiments, 1, 2, 3, 4, 5, 6, 7, 8, 9 or 10 copies of CPRE can be present in a nucleic acid contruct, optionally operatively linked to one or more promoter genes and/or one or more reporter genes. In an alternate embodiment, three copies of the CPRE are present in a nucleic acid construct, optionally with promoter genes and/or reporter genes. In a specific embodiment, the three copies of CPRE (3XCPRE) are selected from the following sequences: RTGACWNAGCANWRTGACWNAGCAN-WRTGACWNAGCANW (SEQ. ID. NO 21); GTGACT-CAGCAGAGTGACTCAGCAGAGTGACTCAGCAGA (SEQ. ID. NO 22);GAGCTCCAGTCACAGTGACTCAG-CAGAATCGAGCTCCAGTCACAGTGACT CAGCA-GAATCGAGCTCCAGTCACAGTGACTCAGCAGAATC (SEQ. ID NO.:2). In a further embodiment, the 3XCPRE sequence is optionally operatively linked to one or more promoter genes and/or one or more reporter genes. In a further embodiment, the 3XCPRE sequence is operably linked to a promoter, which is operably linked to a reporter gene. In another embodiment, the CPRE sequence can be surrounded by one pr more of the nucleotides of promoter elements, such as those promoter elements that surround the CPRE in the native gene. In one nonlimiting example, additional promoter elements can surround the CPRE region of the NQO1 gene (SEQ. ID. NO 3), such as the promoter regions surrounding the CPRE sequence of SEQ. ID. NO. 2 (FIG. 7). Therefore, the actual nucleic acid sequence used can comprise, or include, the CPRE sequence, and can also include additional nucleotides at either the 3' or 5' end, such as, but not limited to those found endogenously surrounding the CPRE sequence in cells.

One skilled in the art will realize that organisms other than humans also contain CPREs (for example, eukaryotes; more specifically, mammals, rodents, worms (*C. elegans*), insects (*Drosophila*) birds, fish, yeast and plants; more specifically, gorillas, rhesus monkeys and chimpanzees). Species-specific polymorphism are known to exist in promoter regions across species. Thus, the invention is intended to include, but not be limited to, CPRE nucleic acid molecules isolated from the above-described organisms.

The present invention demonstrates herein that laminar shear stress does induce the expression of a coordinate set of genes, which are involved in maintaining the intracellular oxidative state of a cell. Laminar shear stress was induced in primary human aortic endothelial cells (HAEC). HAECs were seeded onto gelatin-coated glass slides and grown overnight prior to exposure to shear stress. Shear stress experiments were carried out in a parallel plate flow chamber. Cells were exposed to either static conditions (cells maintained on glass slides in a 150 cm2 tissue culture dish) or exposed to shear stress. For each treatment at least two separate plates were pooled for RNA collection.

To determine genes that can be induced due to exposure to laminar shear stress, a gene expression analysis was conducted on the RNA collected from the HAEC. RNA was collected by lysing cells directly in Trizol (Life Technologies, Inc.). RNA was collected by isopropanol precipitation, 3 μg of total RNA was reverse transcribed into cDNA by reverse transcriptase and the levels of each gene product was measured by semi-quantitative end-point RT-PCR analysis. Oligonucleotide primer pairs were designed to amplify an approximately 500 base pair fragment from the 3' end of each mRNA. After amplification, 15 μl of the sample was electrophoresed on a 1.5% agarose gel and stained by ethidium bromide. Relative band intensities were determined by densitometry. Each sample was assayed at least three times from the same RNA sample expressed as relative levels compared to β-actin.

Exposure of HAEC cells to laminar sheer stress resulted in the induction of the following genes: HO-1, GST, NQO1, NQO2, Ferritin (heavy chain), Ferritin (light chain), gamma glutamyl cysteine synthase (γ-GCS), and microsomal epoxide hydrolase (mEH).

Alignment of the 5' regulatory region from these genes generated a 13 nt sequence core with the sequence 5'-RT-GACWNAGCANW-3' (SEQ ID NO 1).

FIG. 6 shows the DNA sequence alignment of CPREs from the shear stress-regulated genes, NQO1, NQO2, mFerritin (H), mFerritin(H), mFerritin(L), mHO-1, mGST and γ-GCE.

The consensus sequence: 5'RTGACWNAGCANW3' (SEQ ID NO 1), is also shown.

III. DNA Constructs, Vectors, Cells and Organisms

In another embodiment, the invention is a DNA construct comprising an above-described cytoprotective responsive element operably linked to a heterologous protein coding sequence. In a preferred embodiment, the DNA construct is an isolated, recombinant, purified or substantially pure DNA construct. The CPRE is operably linked to the heterologous protein coding sequence. The CPRE mediates increased transcription of the heterologous protein coding sequence in vivo in the presence of an appropriate compound.

Two DNA sequences (such as a CPRE and a heterologous protein coding sequence) are operably linked if the nature of the linkage between the two DNA sequences does not (1) result in the introduction of a frame-shift mutation, (2) interfere with the ability of a promoter region sequence to direct the transcription of the heterologous protein coding sequence, or (3) interfere with the ability of the heterologous protein coding sequence to be transcribed by a promoter region sequence. Thus, a CPRE is operably linked to a heterologous protein coding sequence if the CPRE is capable of effecting increased transcription of that sequence relative to an appropriate control.

In a preferred embodiment, the above-described DNA construct further comprises a promoter (which does not include a CPRE) operably linked to the heterologous protein coding sequence. In another preferred embodiment, the DNA construct further comprises an untranslated region that includes a functional polyadenylation signal operably linked to the heterologous protein coding sequence.

In some embodiments of the invention, the DNA construct includes at least two CPREs upstream of the heterologous protein coding sequence. The two CPREs, preferably three, can be arranged in a tandem or inverted repeat relative to each other. A spacer region can be interposed between the two copies of the CPRE (preferably, the spacer region is about 17 nucleotides long).

In another embodiment, the invention provides a recombinant DNA molecule comprising a vector and the above-described CPRE or DNA construct.

In another embodiment, the invention provides a cell or non-human organism that comprises an above-described CPRE or DNA construct.

In another embodiment, the invention provides 1,3-bis-(substituted-phenyl)-2-propen-1-ones and similar compounds that activate CPRE and thus induce the expression of cytoprotective enzymes. In an aspect of this embodiment, the induction is coordinate.

In the context of this disclosure, the term "heterologous" protein coding sequence is defined as a protein coding sequence wherein the regulatory elements of this protein coding sequence do not naturally include a copy of the CPRE.

In one preferred embodiment, the heterologous protein coding sequence refers to a gene encoding a protein that is easily assayed (e.g., a reporter gene), wherein the assay provides a quantitative measure of the amount of protein (gene product) present.

A nucleic acid molecule, such as DNA, is said to be "capable of expressing" a polypeptide (encoded by a protein coding sequence) if it comprises nucleotide sequences that comprise transcriptional and translational regulatory information and such sequences are "operably linked" to nucleotide sequences which encode the polypeptide. The precise nature of the regulatory regions needed for gene sequence expression can vary from organism to organism, but shall in general include a promoter region which, in eukaryotes, comprises both the promoter (which directs the initiation of RNA transcription) as well as DNA sequences which, when transcribed into RNA, will signal protein synthesis initiation. Such regulatory regions will normally include those 5'-non-coding sequences involved with initiation of transcription and translation, such as the TATA box, capping sequence, CAAT sequence, and the like. Additional elements can also be needed for optimal synthesis of the heterologous protein. These elements can include splice signals, as well as transcription promoters, enhancer signal sequences, and termination signals.

The present invention encompasses the expression of the heterologous protein coding sequence operably linked to the CPRE in eukaryotic cells. Preferred eukaryotic hosts include, for example, yeast, fungi, insect cells, and mammalian cells either in vivo, or in tissue culture. Preferred mammalian cells include endothelial cells (preferably, human aortic endothelial cells (HAECs) or human microvascular endothelial cells (HMECs and transformed cell lines such as HeLa). In the examples described in detail below, DNA constructs according to the invention were introduced into endothelial cells and HeLa cells. However, it can for some reason be desirable to practice the invention in other cell types. Different host cells have characteristic and specific mechanisms for the translational and post-translational processing and modification (e.g., glycosylation, cleavage) of proteins. Appropriate cell lines or host systems can be chosen for the presence of appropriate transcription factors for screening of compounds which increase transcription.

Any of a series of yeast gene sequence expression systems can be utilized which incorporate promoter and termination elements from the actively expressed gene sequences coding for glycolytic enzymes. These enzymes are produced in large quantities when yeast are grown in mediums rich in glucose. Known glycolytic gene sequences can also provide very efficient transcriptional control signals.

A wide variety of transcriptional and translational regulatory sequences can be employed, depending upon the nature of the host. The transcriptional and translational regulatory signals can be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, can be employed.

As discussed above, expression of heterologous protein in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., J. Mol. Appl. Gen. 1:273-288 (1982)); the thymidine kinase (TK) promoter of Herpes virus (McKnight, Cell 31:355-365 (1982)); the SV40 early promoter (Benoist et al., Nature (London) 290:304-310 (1981)); the yeast gal4 gene sequence promoter (Johnston et al., Proc. Nati. Acad. Sci. (USA) 79:6971-6975 (1982); Silver et al., Proc. Natl. Acad. Sci. (USA) 81:5951-5955 (1984)) and the cytomegalovirus (CNV) immediate-early gene promoter (Thomsen et al., Proc. Natl. Acad. Sci (USA) 81:659-663 (1984). Other appropriate promoters include, the phage lambda PL promoter, the E. coli lac, trp, pho and tac promoters, the SV40 early and late promoters and promoters of retroviral LTRs, other suitable promoters will be known to those skilled in the art. The expression constructs can further contain sites for transcription initiation, termination, and, in the transcribed region, a ribosome binding site for translation. The coding portion of the transcripts expressed by the constructs include a translation initiating codon at the beginning and a termination codon (UAA, UGA or UAG) appropriately positioned at the end of the polypeptide to be translated. The vector can be, for example, a phage, plasmid, viral, or retroviral vector. Retroviral vectors can be replication competent or replication defective.

A nucleic acid construct comprising a promoter and a CPRE operably linked to a heterologous protein coding sequence can be introduced into a recipient prokaryotic or eukaryotic cell either as a non-replicating DNA (or RNA) molecule, which can either be a linear molecule or, more preferably, a closed covalent circular molecule. Since such molecules are incapable of autonomous replication without an origin of replication, the expression of the gene can occur through the transient expression of the introduced sequence. Alternatively, permanent expression can occur through the integration of the introduced DNA sequence into the host chromosome, which is the preferred embodiment for high throughput screening of libraries of compounds.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the CPRE. The marker can provide for prototrophy to an auxotrophic host, biocide resistance, e.g., resistance to antibiotics, or heavy metals, such as copper, or the like. The selectable marker gene sequence can either be directly linked to the DNA gene sequences to be expressed, or introduced into the same cell by co-transfection. Preferably, expression of the marker can be quantitated and plotted linearly. Such markers also include dihydrofolate reductase, G418, glutamine synthase (Murphy et al., Biochem J. 227:277-279 (1991); Bebbington et al., BioTechnology 10:169-175 (1992)), neomycin resistance for eukaryotic cell culture, and tetracycline, kanamycin or ampicillin resistance genes for culturing in E. coli and other bacteria.

In another embodiment, the introduced nucleic acid molecule will be incorporated into a plasmid or viral vector capable of autonomous replication in the recipient host. Any of a wide variety of vectors can be employed for this purpose. Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species.

Preferred eukaryotic vectors include for example, vaccinia virus, SV40, retroviruses, adenoviruses, adeno-associated viruses and a variety of commercially-available, plasmid-based mammalian expression vectors that are familiar to those experienced in the art.

Once the vector or nucleic acid molecule containing the construct(s) has been prepared for expression, the DNA construct(s) can be introduced into an appropriate host cell by any of a variety of suitable means, i.e., transformation, transfection, viral infection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of the heterologous protein.

Vectors for use in bacteria include pQE70, pQE60 and pQE-9, available from QIAGEN, Inc.; pBluescript, Yectora, Phagescript vectors, pNHSA, pNH16a, 125pNH18A, pNH46A, available from Stratagene Cloning Systems, Inc.; and ptrc99a, pKK223-3, pKK233-3, pDR540, pRIT5 available from Pharmacia Biotech, Inc. Vectors for use in cukaryotes include pWLNEO, pSY2CAT, pOG44,- pyTI and pSG available from Stratagene; and pSVK3, pBPV, pMSG and pSVI, available from Pharmacia. Expression vectors for use in yeast systems include, but are not limited to, pYES2, pYD1, pTEF1/Zco, pYES2/GS, pPICZ, pGAPZ, pGAPZa-lph, pPIC9, pPIC3.5, pHIL-D2, pHIL-S1, pPIC33K, pPIC9K, and PA0815 (all available from Invitrogen, Carlbad, Calif.). Other suitable vectors will be readily apparent to one skilled in the art.

The introduced DNA can either be expressed in cells transiently or "maintained" in cells. Introduced DNA being "maintained" in cells should be understood as the introduced DNA continuing to be present in essentially all of the cells in question as they continue to grow and proliferate. That is, the introduced DNA is not diluted out of the majority of the cells over multiple rounds of cell division. Rather, it replicates during cell proliferation and at least one copy of the introduced DNA remains in almost every daughter cell. Introduced DNA can be maintained in cells in either of two fashions. First, it can integrate directly into the cell's genome. (This occurs at a rather low frequency). Second, it can exist as an extrachromosomal element, or episome. In order for an episome not to be diluted out during cell proliferation, a selectable marker gene can be included in the introduced DNA and the cells grown under conditions where expression of the marker gene is required. Even in the case where the introduced DNA has integrated in the genome, a selectable marker gene can be included to prevent excision of the DNA from the chromosome.

Preferred eukaryotic hosts include, for example, yeast, fungi, insect cells, and mammalian cells either in vivo, or in tissue culture. Preferred mammalian cells include endothelial cells (preferably, human vascular endothelial cells (HMECs), human aortic endothelial cells (HAECs) and HeLa cells). In the examples described in detail below, DNA constructs according to the invention were introduced into endothelial cells and HeLa cells, in view of the fact that many genes that contain the CPRE consensus sequence are expressed in these cells. However, it can for some reason be desirable to practice the invention in other cell types, in which CPRE-containing genes are also expressed.

Different host cells have characteristic and specific mechanisms for the translational and post-translational processing and modification (e.g., glycosylation, cleavage) of proteins. Appropriate cell lines or host systems can be chosen for the presence of appropriate transcription factors—as set forth herein—for screening of compounds which increase transcription.

Mammalian host cells that could be used include, but are not limited to, human HeLa, 293, H9 and Jurkat cells; mouse NIH3T3 and C127 cells; Cos 1, Cos 7 and CV1, quail QCI-3 cells, mouse L cells and Chinese hamster ovary (CHO) cells. The present invention also relates to host cells containing the above-described vector constructs described herein, and additionally encompasses host cells containing nucleotide sequences of the invention that are operably associated with one or more heterologous control regions (e.g., promoter and/or enhancer elements) using techniques known in the art. The host cell can be a higher eukaryotic cell, such as a mammalian cell (e.g., a human derived cell), or a lower eukaryotic cell, such as a yeast cell, or the host cell can be a prokaryotic cell, such as a bacterial cell. A host strain can be chosen which modulates the expression of the inserted gene sequences, or modifies and processes the gene product in the specific fashion desired. Expression from certain promoters can be elevated in the presence of certain inducers; thus expression of the genetically engineered polypeptide can be controlled.

Introduction of the nucleic acids and nucleic acid constructs of the invention into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986).

In another embodiment, the invention also encompasses primary, secondary, and immortalized host cells of vertebrate origin, particularly mammalian origin.

Inducing the Expression of a CPRE-Containing Gene

A transfected cell line as described above provides a convenient tool for screening candidate compounds that increase transcription of a mRNA regulated by a cytoprotective responsive element. In one embodiment, the cell line is transiently transfected. Alternatively, the cell is stably transfected. A culture of the transfected cell line containing the CPRE reporter construct can be grown in the presence of the candidate compound, lysed and the lysate assayed for increased expression of the heterologous protein coding sequence which is operably linked to the CPRE, as described herein. In parallel, a culture grown in the absence of the candidate compound can be lysed and assayed. The assay results are compared to determine whether the candidate compound increased expression of the heterologous protein. The advantage of using a stably transfected cell line is the convenience provided by not having to introduce a DNA construct transiently every time a candidate compound is screened. In a preferred embodiment, the structural gene encoding the heterologous protein is a reporter gene, preferably the chloramphenicol transferase (CAT), luciferase (luc), human growth hormone, $\beta$-galactosidase, $\beta$-glucuronidase, secreted alkaline phosphatase, green fluorescent protein, or other genes that can be detected, e.g., immunologically (by antibody assay) or fluorescently (see, for examples, Table 1). Any of the sequences that are described in FIG. 6 can be used to prepare the DNA construct operably linked to a protein coding sequence.

TABLE 1

| Patent No. | Title |
|---|---|
| 6,329,156 | Method for screening inhibitors of the toxicity of *Bacillus anthracis* |
| 6,326,480 | Antisense reporter system for assaying RNA virus replication |
| 6,326,157 | Recombinant fluorescent protein microsphere calibration standard |
| 6,323,039 | Compositions and methods for assaying subcellular conditions and processes using energy transfer |
| 6,319,669 | Modified green fluorescent proteins |
| 6,316,181 | Establishment of cell lines with persistent expression of a green fluorescent protein (GFP) using a pIRES/EGFP DNA vector construct |
| 6,303,373 | Method of measuring plasma membrane targeting of GLUT4 |
| 6,291,177 | Assay for agents which alter G-protein coupled receptor activity |
| 6,284,519 | Cell systems having specific interaction of peptide binding pairs |
| 6,284,496 | DNA vector for determining the presence of out-of-reading-frame mutations |
| 6,280,934 | Assay for agents which alter G-protein coupled receptor activity |
| 6,274,354 | Methods using cre-lox for production of recombinant adeno-associated viruses |
| 6,270,958 | Detection of negative-strand RNA viruses |
| 6,268,201 | IniB, iniA and iniC genes of mycobacteria and methods of use |
| 6,265,548 | Mutant Aequorea victoria fluorescent proteins having increased cellular fluorescence |
| 6,261,760 | Regulation of the cell cycle by sterols |
| 6,255,558 | Gene expression |
| 6,255,071 | Mammalian viral vectors and their uses |
| 6,251,677 | Hybrid adenovirus-AAV virus and methods of use thereof |
| 6,251,602 | Cell systems having specific interaction of peptide binding pairs |
| 6,251,582 | Alternative G-coupled receptors associated with retroviral entry into cells, methods of identifying the same and diagnostic and therapeutic uses thereof |
| 6,251,384 | Metastasis models using green fluorescent protein (GFP) as a marker |
| 6,248,558 | Sequence and method for genetic engineering of proteins with cell membrane translocating activity |
| 6,248,550 | Assays for protein kinases using fluorescent protein substrates |
| 6,248,543 | Compositions and methods for screening antimicrobials |
| 6,232,107 | Luciferases, fluorescent proteins, nucleic acids encoding the luciferases and fluorescent proteins and the use thereof in diagnostics, high throughput screening and novelty items |
| 6,228,639 | Vectors and methods for the mutagenesis of mammalian genes |
| 6,225,082 | Myelin basic protein MRNA transport and translation enhancer sequences |
| 6,221,612 | Photon reducing agents for use in fluorescence assays |
| 6,218,185 | Piggybac transposon-based genetic transformation system for insects |
| 6,214,567 | Immortalized human keratinocyte cell line |
| 6,214,563 | Photon reducing agents for reducing undesired light emission in assays |
| 6,210,922 | Serum free production of recombinant proteins and adenoviral vectors |
| 6,210,910 | Optical fiber biosensor array comprising cell populations confined to microcavities |
| 6,203,986 | Visualization of RNA in living cells |
| 6,197,928 | Fluorescent protein sensors for detection of analytes |
| 6,180,343 | Green fluorescent protein fusions with random peptides |
| 6,172,188 | Fluorescent proteins |
| 6,153,409 | Process for continuous optimized protein production in insect larvae |

TABLE 1-continued

| Patent No. | Title |
|---|---|
| 6,150,176 | Fluorescent protein sensors for measuring the pH of a biological sample |
| 6,146,826 | Green fluorescent protein |
| 6,140,132 | Fluorescent protein sensors for measuring the pH of a biological sample |
| 6,136,539 | Compositions and methods for the inhibition of MUC-5 mucin gene expression |
| 6,136,538 | Silent inducible virus replicons and uses thereof |
| 6,133,429 | Chromophores useful for the preparation of novel tandem conjugates |
| 6,130,313 | Rapidly degrading GFP-fusion proteins |
| 6,124,128 | Long wavelength engineered fluorescent proteins |
| 6,110,711 | Method of defining cell types by probing comprehensive expression libraries with amplified RNA |
| 6,096,865 | Mutants of the green fluorescent protein having improved fluorescent properties at 37 degrees |
| 6,096,717 | Method for producing tagged genes transcripts and proteins |
| 6,093,808 | I.kappa.BEGFP constructs, cell lines and methods of use |
| 6,090,919 | FACS-optimized mutants of the green fluorescent protein (GFP) |
| 6,083,690 | Methods and compositions for identifying osteogenic agents |
| 6,077,707 | Long wavelength engineered fluorescent proteins |
| 6,066,476 | Modified green fluorescent proteins |
| 6,060,247 | Post-mitotic neurons containing adenovirus vectors that modulate apoptosis and growth |
| 6,054,321 | Long wavelength engineered fluorescent proteins |
| 6,037,133 | I.kappa.BEGFP constructs, cell lines and methods of use |
| 6,027,881 | Mutant Aequorea Victoria fluorescent proteins having increased cellular fluorescence |
| 6,025,192 | Modified retroviral vectors |
| 6,020,192 | Humanized green fluorescent protein genes and methods |
| 6,013,447 | Random intracellular method for obtaining optimally active nucleic acid molecules |
| 6,001,557 | Adenovirus and methods of use thereof |
| 5,994,077 | Fluorescence-based isolation of differentially induced genes |
| 5,994,071 | Assessment of prostate cancer |
| 5,993,778 | Functional expression of, and assay for, functional cellular receptors in vivo |
| 5,989,808 | Identification of compounds affecting specific interaction of peptide binding pairs |
| 5,985,577 | Protein conjugates containing multimers of green fluorescent protein |
| 5,968,773 | System and method for regulation of gene expression |
| 5,968,738 | Two-reporter FACS analysis of mammalian cells using green fluorescent proteins |
| 5,958,713 | Method of detecting biologically active substances by using green fluorescent protein |
| 5,952,236 | Enzyme-based fluorescence biosensor for chemical analysis |
| 5,948,889 | Compositions and methods for screening antimicrobials |
| 5,948,681 | Non-viral vehicles for use in gene transfer |
| 5,942,387 | Combinatorial process for preparing substituted thiophene libraries |
| 5,932,435 | Screening antisense and ribozyme nucleic acids in schizosaccharomyces pombe |
| 5,922,576 | Simplified system for generating recombinant adenoviruses |
| 5,919,445 | Use of green fluorescent protein to trace the infection of baculovirus in insects and to increase viral UV stability |
| 5,914,233 | Screening assay for the identification of agents which alter expression of PTH-rP |
| 5,891,646 | Methods of assaying receptor activity and constructs useful in such methods |

One nonlimiting example of a reporter assay system is the luciferase assay. The luciferase assay system is a method for determining the level of luciferase gene expression in cells transfected with luciferase reporter vectors. The reaction catalyzed by luciferase is the oxidation of luciferin with concomitant production of a photon. This light production can be quantitated using a luminometer (e.g., Turner Designs TD-20/20, Promega) or a scintillation counter. This allows DNA fragments to be analyzed for their transcriptional activity. For example, vectors can be deigned to include, for example, a CPRE element operably linked to a promoter, such as a CMV, SV40 or TK promoter, which is operably linked to a luciferase gene, such as firefly luciferase or *Renilla* luciferase. In addition, a second construct containing a luciferase gene can be used as an internal control. For example, a promoter, such as SV40, CMV, or TK, operably linked to a luciferase gene can be cotransfected with any experimental reporting vector. Examples of experimental reporting vectors include at least one, preferably three, CPRE elements operably linked to a promoter, such as a SV40, CMV or TK promoter, operably linked to a reporter gene, such as luciferase or CAT. Also, see, for example, Lorenz, W. W. et al. (1991) Isolation and expression of a cDNA encoding *Renilla* reniformisluciferase. Proc. Natl. Acad. Sci. USA 88, 4438-42.; Matthews, J. C. et al. (1977) Substrate and substrate analogue binding properties of *Renillaluciferase*. Biochemistry 16, 85-91; Gluzman, Y. (1981) SV40-transformed simian cells support the replication of early SV40 mutants. Cell 23, 175-82; Bothwell, A. L. M. et al. (1981) Heavy chain variable region contribution to the NPb family of antibodies: somatic mutation evident in a gamma 2a variable region. Cell 24, 625-37; Senapathy, P., Shapiro, M. B. and Harris, N. L. (1990) Splice junctions, branch point sites, and exons: sequence statistics, identification, and applications to genome project. Meth. Enzymol.183, 252-78; Gross, M. K., Kainz, M. S. and Merrill, G. F. (1987) Introns are inconsequential to efficient formation of cellular thymidine kinase mRNA in mouse L cells. Mol. Cell. Biol.7, 4576-81; Buchman, A. R. and Berg, P. (1988) Comparison of intron-dependent and intron independent gene expression. Mol. Cell. Biol.8, 4395-405; Evans, M. J. and Scarpulla, R. C. (1989) Introns in the 3'-untranslated region can inhibit chimeric CAT and beta-galactosidase gene expression. Gene 84, 135-42; Huang, M. T. F. and Gorman, C. M. (1990) Intervening sequences increase efficiency of, RNA 3'processing and accumulation of cytoplasmic RNA. Nucl. Acids Res.18, 937-47; Huang, M. T. F. and Gorman, C. M. (1990) The simian virus 40 small-t intron, present in many common expression vectors, leads to aberrant splicing. Mol. Cell. Biol.10, 1805-10; Proudfoot, N. J. (1991) Poly(A) signals. Cell 64, 671-4; Bernstein, P. and Ross, J. (1989) Poly(A), poly(A) binding protein and the regulation of mRNA stability. Trends Biochem. Sci. 14, 373-7; Jackson, R. J. and Standart, N. (1990) Do the poly(A) tail and 3'untranslated region control mRNA translation? Cell 62, 15-24; Carswell, S. and Alwine, J. C. (1989) Efficiency of utilization of the simian virus 40 late polyadenylation site: effects of upstream sequences. Mol. Cell. Biol.9,4248-58; Farr, A. and Roman, A. (1991) A pitfall of using a second plasmid to determine transfection efficiency. Nucl. Acids Res.20, 920; Behr, J. P. et al. (1989) Efficient gene transfer into mammalian primary endocrine cells with lipopolyamine-coated DNA. Proc. Natl. Acad. Sci. USA 86, 6982-6; Loeffler, J. P. et al. (1990) Lipopolyamine-mediated transfection allows gene expression studies in primary neuronal cells. J. Neurochem. 54, 1812-15; Graham, F.L. and van der Eb, A.J. (1973) A new technique for the assay of infectivity of human adenovirus 5 DNA. Virology 52, 456-67; Wigler, M. et al. (1977) Transfer of purified herpes virus thymidine kinase gene to cultured mouse cells. Cell 11, 223-32; McCutchan, J. H. and Pagano, J. S. (1968) Enhancement of the infectivity of simian virus 40 deoxyribonucleic acid with diethylaminoethyl-dextran. J. Natl. Cancer Inst.41, 351-7; Al-Moslih, M. I. and Dubes, G. R. (1973) The kinetics of DEAE-dextran-induced cell sensitization to transfection. J. Gen. Virol.18, 189-93.; Luthman, H. and Magnusson, G. (1983) High efficiency polyoma DNA transfection of chloroquine treated cells. Nucl. Acids Res.11, 1295-308; Kawai, S. and Nishizawa, M. (1984) New procedure for DNA transfection with polycation and dimethyl sulfoxide. Mol. Cell. Biol.4, 1172-4; Aubin, R. J., Weinfeld, M. and Paterson, M. C. (1988) Factors influencing efficiency and reproducibility of polybrene-assisted gene transfer. Som. Cell Mol. Genet.14, 155-67; Andreason, G. L. and Evans, G. A. (1988) Introduction and expression of DNA molecules in eukaryotic cells by electroporation. BioTechniques6, 650-60; Neumann, E. et al. (1982) Gene transfer into mouse lyoma cells by electroporation in high electric fields. EMBO J.1, 841-5.

In yet another embodiment, the present invention provides a method of screening for a compound (preferably, a drug) that increases transcription of an mRNA regulated by a cytoprotective responsive element (preferably by modulating protein-protein interactions at the cytoprotective responsive element; such interaction can be direct or indirect as discussed herein), comprising the steps of:

i) growing a first culture of the cells comprising an above described DNA construct in the absence of the candidate compound, ii) lysing the first culture to produce a first extract;

iii) assaying the first extract for the amount of transcription of a mRNA that comprises the structural coding sequence;

iv) growing a second culture of the cells comprising an above-described DNA construct in the presence of the candidate compound;

v) lysing the second culture to produce a second extract;

vi) assaying the second extract for the amount of transcription of an mRNA which comprises the structural coding sequence; and vii) comparing the amounts of transcription of the first extract and the second extract, wherein a greater amount of transcription in the second extract as compared to the first extract indicates that the candidate compound increases transcription of a mRNA regulated by the cytoprotective responsive element. The above described method can include the first step of introducing into an above-described cell an above-described DNA construct.

In one preferred embodiment, the candidate compound is identified or created via combinatorial chemistry. In another preferred embodiment, the compound interacts with a transcription factor that binds the CPRE. The transcription factor can be a single protein or protein complex. Assays for transcription are meant to include, but not be limited to, (1) the direct analysis of the amount of mRNA present in the extract, (2) analysis of the amount of protein (derived from the fusion of a heterologous protein operably linked to the CPRE) present in the extract (which is generally indicative of the amount of transcription, although other factors such as mRNA stability are also involved here) and (3) analysis of a chemical or phenotypic change which is indicative of the amount of transcription of a protein coding sequence. Preferably, a liner response is obtained.

Thus, in a further embodiment, the present invention relates to a method of screening for a compound that increases transcription of an mRNA regulated by a cytoprotective responsive element (preferably by interacting with the cytoprotective responsive element; such interaction can be direct or indirect as discussed herein), comprising the steps of:

(a) assaying a first cellular extract for the amount of protein produced from a mRNA wherein the mRNA is expressed from a DNA construct, the expression being in the absence of a candidate compound and the DNA construct comprising:

a CPRE having a DNA sequence 5'RTGACWNAG-CANW3' (SEQ ID NO:1) or another sequence depicted in FIG. 6 operably linked to a protein coding sequence;

(b) assaying a second cellular extract for the amount of protein produced from an mRNA wherein the mRNA is expressed from the DNA construct, the transcription being in the presence of the candidate compound; and (c) comparing the amounts of protein of the first extract and the second extract, wherein a greater amount of protein in the second extract as compared to the first extract indicates the candidate compound increases transcription of the mRNA regulated by the cytoprotective responsive element.

In another embodiment, the present invention relates to a method of screening for a compound that increases transcription of a mRNA regulated by a cytoprotective responsive element, comprising the steps of:

growing a first culture of cells comprising an above-described DNA construct in the absence of a candidate compound, lysing the first culture to produce a first extract;

assaying the first extract for the amount of protein encoded by the heterologous protein coding sequence;

growing a second culture of the cells in the presence of the candidate compound, lysing the second culture to produce a second extract;

assaying the second extract for the amount of protein encoded by the heterologous protein coding sequence; and comparing the amount of the protein of the first extract and the second extract, wherein a greater amount of the protein in the second extract as compared to the first extract indicates that the candidate compound increases transcription of a mRNA regulated by the cytoprotective responsive element. The above-described method can include the step of first introducing into a cell an above-described DNA construct.

The construct can also include an additional functional selectable marker gene whose expression is required under certain culture conditions to maintain the introduced DNA in the cells. If the cells are consistently cultured in the presence of a specific selecting agent, only cells comprising this marker gene will survive selection. Thus, the introduced DNA will be stably maintained in essentially all surviving cells. Genes of this type are known to a person skilled in the art.

The present invention as described herein is the first demonstration of coordinate induction of a set of shear stress regulated genes that are under transcriptional control of a common element, the CPRE. The invention described herein provides convenient DNA constructs, and convenient, rapid and efficient methods for screening for candidate compounds that can be involved in increasing the coordinate expression of the set of shear stress regulated genes that are regulated by CPRE.

The invention contemplates the assembly of a kit including reagents with which one can conveniently practice the invention. The kit can, for example, include a DNA construction comprising a reporter gene as described herein, as well as a substrate of the reporter gene so that reporter gene activity can be quantitated. The invention also contemplates automation of the methods described herein. That is, a machine can be constructed that can be used to carry out the invention, further increasing convenience and efficiency.

IV. Compounds (Including Drugs and Proteins) that Directly or Indirectly Activate the CPRE or Activate or Inhibit Proteins in the CPRE Signaling Pathway Such that it Results in an Overall Increase in CPRE Activity.

In another embodiment, the present invention provides a purified compound, for example, a transcription factor or a protein that binds to a cytoprotective responsive element (CPRE) as described in FIG. 6. In one embodiment, the invention utilizes a substantially pure compound.

Thus, the invention additionally contemplates use of the CPRE as a reagent for the purification of a compound (preferably, a transcription factor) with which it interacts. For example, an oligonucleotide including the CPRE is conjugated to a resin to produce an affinity resin. A crude cell extract, such as a nuclear extract, is incubated with the affinity resin under conditions where a transcription factor or factors bind to the CPRE moiety. After first washing the complexed resin to dissociate free and non-specially bound proteins or protein complexes, a more stringent buffer will then be applied to elute specifically bound factors. This procedure is performed using column chromatography or batchwise extraction as is know in the art. The transcription factors are further purified by SDS-PAGE electrophoresis. The amino acid sequence of the transcription factors are determined using protein isolated from the SDS-PAGE gel as is known in the art.

One skilled in the art can readily follow other known methods for isolating proteins in order to obtain the transcription factor free of natural contaminants. These include, but are not limited to: size-exclusion chromatography, HPLC, ion-exchange chromatography and immuno-affinity chromatography.

In one embodiment, the purification procedures comprise ion-exchange chromatography and size exclusion chromatography. Any one of a large number of ion-exchange resins known in the art can be employed, including for example, phosphocellulose, DEAE-Sephadex, monoQ, sepharose, macro-prepQ, AG1-X2, or HQ. Examples of suitable size exclusion resins include, but are not limited to, Superdex 2000, Superose 12 and Sephycryl 200. Elution can be achieved, for example, with aqueous solutions of potassium chloride or sodium chloride at concentrations ranging from 0.01 M to 2.0 M.

In another embodiment, the invention is a purified compound (preferably, a low molecular weight organic compound, e.g., less than 1000, and preferably less than 750) that binds to an above-described cytoprotective responsive element (CPRE) or a CPRE transcription factor, or another signaling molecule such as Keap-1 that is involved in regulating CPRE expression (see below). In yet another embodiment, the invention is the bound form of the purified compound (preferably, a drug, protein, peptide or nucleic acid, including a transcriptional factor) with a cytoprotective responsive element (CPRE) or a CPRE transcription factor as illustrated in FIG. 6, or another signaling molecule such as Keap-1 that is involved in regulating CPRE expression.

Thus, the invention additionally contemplates use of the CPRE as a reagent for the identification of a compound (preferably, a drug) with which it directly or indirectly interacts.

V. A Method of Identifying Upstream Signaling Factors that Directly or Indirectly Modulate CPRE Activity Any method suitable for detecting protein-protein interactions can be employed for identifying upstream signaling factors that can be cellular or extracellular proteins, which interact to modulate CPRE gene expression. Those represent pathway proteins and the genes that encode them represent pathway genes.

Among the traditional methods that can be employed are co-immunoprecipitation, crosslinking and co-purification through gradients or chromatographic columns. Utilizing procedures such as these allows for the identification of pathway gene products. Once identified, a pathway protein can be used, in conjunction with standard techniques, to identify its corresponding pathway gene. For example, at least a portion of the amino acid sequence of the pathway protein can be ascertained using techniques well known to those of skill in the art, such as via the Edman degradation technique (see, e.g., Creighton, 1983, Proteins: Structures and Molecular Principles, W. H. Freeman & Co., N.Y., pp.34-49). The amino acid sequence obtained can be used as a guide for the generation of oligonucleotide mixtures that can be used to screen for pathway gene sequences. Screening made be accomplished, for example by standard hybridization or PCR techniques. Techniques for the generation of oligonucleotide mixtures and screening are well-known. (See, e.g., Ausubel, supra., and PCR Protocols: A Guide to Methods and Applications, 1990, Innis, M. et al., eds. Academic Press, Inc., New York).

Additionally, methods can be employed which result in the simultaneous identification of pathway genes that encode the protein interacting with a protein involved in the upstream signaling cascade to activate the CPRE. These methods include, for example, probing expression libraries with labeled protein known or suggested to be involved in the signaling cascade to activate the CPRE, for example Nrf-2, using this protein in a manner similar to the well known technique of antibody probing of λgt11 libraries.

One such method that detects protein interactions in vivo, the two-hybrid system, is described in detail for illustration only and not by way of limitation. One version of this system has been described (Chien et al., 1991, Proc. Natl. Acad. Sci. USA, 88:9578-9582) and is commercially available from Clontech (Palo Alto, Calif.).

Briefly, utilizing such a system, plasmids are constructed that encode two hybrid proteins: one consists of the DNA-binding domain of a transcription activator protein fused to a known protein, and the other consists of the activator protein's activation domain fused to an unknown protein that is encoded by a cDNA which has been recombined into this plasmid as part of a cDNA library. The plasmids are transformed into a strain of the yeast *Saccharomyces cerevisiae* that contains a reporter gene (e.g., luciferase) whose regulatory region contains the activator's binding sites. Either hybrid protein alone cannot activate transcription of the reporter gene, the DNA-binding domain hybrid because it does not provide activation function and the activation domain hybrid because it cannot localize to the activator's binding sites. Interaction of the two proteins reconstitutes the functional activator protein and results in expression of the reporter gene, which is detected by an assay for the reporter gene product.

The two-hybrid system or related methodology can be used to screen activation domain libraries for proteins that interact with a known "bait" gene protein. Total genomic or cDNA sequences can be fused to the DNA encoding an activation domain. Such a library and a plasmid encoding a hybrid of the bait gene protein fused to the DNA-binding domain can be cotransformed into a yeast reporter strain, and the resulting transformants can be screened for those that express the reporter gene. These colonies can be purified and the library plasmids responsible for reporter gene expression can be isolated. DNA sequencing can then be used to identify the proteins encoded by the library plasmids.

For example, and not by way of limitation, the bait gene can be cloned into a vector such that it is translationally fused to the DNA encoding the DNA-binding domain of the GAL4 protein.

A cDNA library of the cell line from which proteins that interact with bait gene are to be detected can be made using methods routinely practiced in the art. According to the particular system described herein, for example, the cDNA fragments can be inserted into a vector such that they are translationally fused to the activation domain of GAL4. This library can be co-transformed along with the bait gene-GAL4 fusion plasmid into a yeast strain that contains a luciferase gene driven by a promoter, which contains the GAL4 activation sequence. A cDNA encoded protein, fused to the GAL4 activation domain, that interacts with bait gene will reconstitute an active GAL4 protein and thereby drive expression of the luciferase gene. The cDNA can then be purified from these strains, and used to produce and isolate the bait gene-interacting protein using techniques routinely practiced in the art.

VI. A Method to Identify Compounds that Bind to Nrf-2 or Keap-1 and Induce Transcription Via CPRE.

For example, and not by way of limitation, one pathway protein, described herein as a target protein, that can be used to identify other pathway proteins (possibly by, but not limited to, the methods described above) is Nrf-2. Nrf-2 has previously been shown to induce transcription of the CPRE. In a preferred embodiment, pathway proteins can be identified that enhance the affinity of Nrf-2 for the CPRE.

For example, and not by way of limitation, another pathway protein, described herein as a target protein, that can be used to identify other pathway proteins (possibly by, but not limited to the methods described above) is Keap-1.

In a preferred embodiment, a newly identified pathway protein can bind to Keap-1 and thereby prevent the binding of Keap-1 to Nrf-2. Thus, this new pathway protein will allow for the translocation of Nrf-2 into the nucleus to induce CPRE expression.

The two target proteins, Nrf-2 and Keap-1, or any other pathway protein identified as described above, can, in vivo, interact with one or more cellular or extracellular proteins. Such proteins can include, but are not limited to, those proteins identified via methods such as those described above. For the purposes of this discussion, these cellular and extracellular proteins are referred to herein as "binding partners". Compounds that disrupt such interactions can be useful in regulating the activity of the CPRE. Such compounds can include, but are not limited to molecules such as antibodies, peptides, as well as, preferably, small molecular weight organic compounds.

The basic principle of the assay systems used to identify compounds that interfere with the interaction between the target proteins described above and protein binding partner or partners involves preparing a reaction mixture containing the target protein and the binding partner under conditions and for a time sufficient to allow the two proteins to interact and bind, thus forming a complex. In order to test a compound for inhibitory activity, the reaction mixture is prepared in the presence and absence of the test compound. The test compound can be initially included in the reaction mixture or can be added at a time subsequent to the addition of target protein and its cellular or extracellular binding partner. Control reaction mixtures are incubated without the test compound or with a placebo. The formation of any complexes between the target protein and the cellular or extracellular binding partner is then detected. The formation of a complex in the control reaction, but not in the reaction mixture containing the test compound, indicates that the compound interferes with the interaction of the target protein and the interactive binding partner protein.

The assay for compounds that interfere with the interaction of the binding partners can be conducted in a heterogeneous or homogeneous format. Heterogeneous assays involve anchoring one of the binding partners onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the binding partners, e.g., by competition, can be identified by conducting the reaction in the presence of the test substance; i.e., by adding the test substance to the reaction mixture prior to or simultaneously with the target gene protein and interactive cellular or extracellular protein. Alternatively, test compounds that disrupt preformed complexes, e.g. compounds with higher binding constants that displace one of the binding partners from the complex, can be tested by adding the test compound to the reaction mixture after complexes have been formed. The various formats are described briefly below.

In a heterogeneous assay system, either the target gene protein or the interactive cellular or extracellular binding partner protein, is anchored onto a solid surface, and its binding partner, which is not anchored, is labeled, either directly or indirectly. In practice, microtitre plates are conveniently utilized. The anchored species can be immobilized by non-covalent or covalent attachments. Non-covalent attachment can be accomplished simply by coating the solid surface with a solution of the protein and drying. Alternatively, an immobilized antibody specific for the protein can be used to anchor the protein to the solid surface. The surfaces can be prepared in advance and stored.

In order to conduct the assay, the binding partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the binding partner was pre-labeled, the detection of label immobilized on the surface indicates that complexes were formed. Where the binding partner is not pre-labeled, an indirect label can be used to detect complexes anchored on the surface; e.g., using a labeled antibody specific for the binding partner (the antibody, in turn, can be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one binding partner to anchor any complexes formed in solution, and a labeled antibody specific for the other binding partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the target protein and the interactive cellular or extracellular protein is prepared in which one of the binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the binding partners from the preformed complex will result in the generation of a signal above background. In this way, test substances that disrupt target protein-cellular or extracellular protein interaction can be identified.

In another embodiment of the invention, these same techniques can be employed using peptide fragments that correspond to the binding domains of the target protein and the interactive cellular or extracellular protein, respectively, in place of one or both of the full length proteins. Any number of methods routinely practiced in the art can be used to identify and isolate the protein's binding site. These methods include, but are not limited to, mutagenesis of one of the genes encoding the proteins and screening for disruption of binding in a co-immunoprecipitation assay. Compensating mutations in the target gene can be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain can remain associated with the solid material, which can be isolated and identified by amino acid sequencing. Also, once the gene coding for the for the cellular or extracellular protein is obtained, short gene segments can be engineered to express peptide fragments of the protein, which can then be tested for binding activity and purified or synthesized.

VII. A Method to Modulate the Expression of VCAM-1 or Another Redox-sensitive Gene Product Comprising Administering a Compound that Activates CPRE.

Cells that contain and express the CPRE sequences can be utilized to identify compounds that exhibit cytoprotective and/or anti-inflammatory disease activity.

Such cells can include endothelial cells such as HAECs and HMECs as well as generic mammalian cell lines such as HeLa cells.

Such cells can be treated with compounds and examined for phenotypes associated with inflammatory disease.

In a nonlimiting example, HMECs can be treated with test compounds. The HMECs can then be examined for phenotypes associated with an anti-inflammatory phenotype, including, but not limited to changes in cellular morphology, cell proliferation, cell migration, and mononuclear cell adhesion; or for the effects on production of other proteins involved in inflammation such as ICAM, VCAM, and MCP-1.

VIII. CPRE Regulated Gene Products that are Induced by Shear Stress

Cells that contain and express the CPRE sequences can be utilized to identify genes that are induced by shear stress conditions. Such cells can include endothelial cells such as HAECs and HMECs as well as generic mammalian cell lines such as HeLa cells. Such cells can be exposed to shear stress conditions and examined for the selected upregulation of genes associated with this condition.

In a nonlimiting example, laminar shear stress was induced in primary human aortic endothelial cells (HAEC). HAECs were seeded onto gelatin-coated glass slides and grown overnight prior to exposure to shear stress. Shear stress experiments were carried out in a parallel plate flow chamber. Cells were exposed to either static conditions (cells maintained on glass slides in a 150 cm2 tissue culture dish) or exposed to shear stress. For each treatment at least two separate plates were pooled for RNA collection.

In a preferred embodiment, to determine genes that can be induced due to exposure to laminar shear stress, a gene expression analysis was conducted on the RNA collected from the HAECs. RNA was collected by lysing cells directly in Trizol (Life Technologies, Inc.) RNA was collected by isopropanol precipitation, 3 µg of total RNA was reverse transcribed into cDNA by reverse transcriptase and the levels of each gene product was measured by semi-quantitative end-point RT-PCR analysis. Oligonucleotide primer pairs were designed to amplify an approximately 500 base pair fragment from the 3' end of each mRNA. After amplification, 15 µl of the sample was electrophoresed on a 1.5% agarose gel and stained by ethidium bromide. Relative band intensities were determined by densitometry. Each sample was assayed at least three times from the same RNA sample expressed as relative levels compared to β-actin.

Exposure of HAEC cells to laminar shear stress resulted in the induction of the following genes: HO-1, GST, NQO1, NQO2, Ferritin (heavy chain), Ferritin (light chain), gamma glutamyl cysteine synthase (γ-GCS), and microsomal epoxide hydrolase (mEH).

One skilled in the art will realize that there are other methods used to assess differential gene expression in response to a physiological condition, such as shear stress. In order to identify differentially expressed genes, RNA, either total or mRNA, can be isolated from cells exposed to different physiological conditions. RNA samples are obtained from experimental cells and from corresponding control cells. Any RNA isolation technique that does not select against the isolation of mRNA can be utilized for the purification of such RNA samples. See, for example, Sambrook et al., 1989, Molecular Cloning, A Laboratory Manual, Cold Spring Harbor Press, N.Y.; and Ausubel, F. M. et al., eds., 1987-1993, Current Protocols in Molecular Biology, John Wiley & Sons, Inc. New York, both of which are incorporated herein by reference in their entirety. Additionally, large numbers of tissue samples can readily be processed using techniques well known to those of skill in the art, such as, for example, the single-step RNA isolation process of Chomczynski, P. (1989, U.S. Pat. No. 4,843,155), which is incorporated herein by reference in its entirety.

Transcripts within the collected RNA samples which represent RNA produced by differentially expressed genes can be identified by utilizing a variety of methods which are well known to those of skill in the art. For example, differential screening (Tedder, T. F. et al., 1988, Proc. Natl. Acad. Sci. USA 85:208-212), subtractive hybridization (Hedrick, S. M. et al., 1984, Nature 308:149-153; Lee, S. W. et al., 1984, Proc. Natl. Acad. Sci. USA 88:2825), and differential display (Liang, P., and Pardee, A. B., 1993, U.S. Pat. No. 5,262,311, which is incorporated herein by reference in its entirety), can be utilized to identify nucleic acid sequences derived from genes that are differentially expressed.

Differential screening involves the duplicate screening of a cDNA library in which one copy of the library is screened with a total cell cDNA probe corresponding to the mRNA population of one cell type while a duplicate copy of the cDNA library is screened with a total cDNA probe corresponding to the mRNA population of a second cell type. For example, one cDNA probe can correspond to a total cell cDNA probe of a cell type derived from a control condition, while the second cDNA probe can correspond to a total cell cDNA probe of the same cell type derived from an experimental condition. Those clones that hybridize to one probe but not to the other potentially represent clones derived from genes differentially expressed in the cell type of interest in control versus experimental conditions.

Subtractive hybridization techniques generally involve the isolation of mRNA taken from two different sources, e.g., control and experimental tissue, the hybridization of the mRNA or single-stranded cDNA reverse-transcribed from the isolated mRNA, and the removal of all hybridized, and therefore double-stranded, sequences. The remaining non-hybridized, single-stranded cDNAs, potentially represent clones derived from genes that are differentially expressed in the two mRNA sources. Such single-stranded cDNAs are then used as the starting material for the construction of a library comprising clones derived from differentially expressed genes.

The differential display technique describes a procedure, utilizing the well known polymerase chain reaction (PCR; the experimental embodiment set forth in Mullis, K. B., 1987, U.S. Pat. No. 4,683,202) which allows for the identification of sequences derived from genes that are differentially expressed. First, isolated RNA is reverse-transcribed into single-stranded cDNA, utilizing standard techniques that are well known to those of skill in the art. Primers for the reverse transcriptase reaction can include, but are not limited to, oligo dT-containing primers, preferably of the reverse primer type of oligonucleotide described below. Next, this technique uses pairs of PCR primers, as described below, which allow for the amplification of clones representing a random subset of the RNA transcripts present within any given cell. Utilizing different pairs of primers allows each of the mRNA transcripts present in a cell to be amplified. Among such amplified transcripts can be identified those which have been produced from differentially expressed genes. The reverse oligonucleotide primer of the primer pairs can contain an oligo dT stretch of nucleotides, preferably eleven nucleotides long, at its 5' end, which hybridizes to the poly(A) tail of mRNA or to the complement of a cDNA reverse transcribed from an mRNA poly(A) tail. Second, in order to increase the specificity of the reverse primer, the primer can contain one or more, preferably two, additional nucleotides at its 3' end. Because, statistically, only a subset of the mRNA derived sequences present in the sample of interest will hybridize to such primers, the additional nucleotides allow the primers to amplify only a subset of the mRNA derived sequences present in the sample of interest. This is preferred in that it allows more accurate and complete visualization and characterization of each of the bands representing amplified sequences. The forward primer can contain a nucleotide sequence expected, statistically, to have the ability to hybridize to cDNA sequences derived from the tissues of interest. The nucleotide sequence can be an arbitrary one, and the length of the forward oligonucleotide primer can range from about 9 to about 13 nucleotides, with about 10 nucleotides being preferred. Arbitrary primer sequences cause the lengths of the amplified partial cDNAs produced to be variable, thus allowing different clones to be separated by using standard denaturing sequencing gel electrophoresis. PCR reaction conditions should be chosen which optimize amplified product yield and specificity, and, additionally, produce amplified products of lengths that can be resolved utilizing standard gel electrophoresis techniques. Such reaction conditions are well known to those of skill in the art, and important reaction parameters include, for example, length and nucleotide sequence of oligonucleotide primers as discussed above, and annealing and elongation step temperatures and reaction times. The pattern of clones resulting from the reverse transcription and amplification of the mRNA of two different cell types is displayed via sequencing gel electrophoresis and compared. Differences in the two banding patterns indicate potentially differentially expressed genes.

Once potentially differentially expressed gene sequences have been identified via bulk techniques such as, for example, those described above, the differential expression of such putatively differentially expressed genes should be corroborated. Corroboration can be accomplished via, for example, such well known techniques as Northern analysis and/or RT-PCR. Upon corroboration, the differentially expressed genes can be further characterized.

Also, amplified sequences of differentially expressed genes obtained through, for example, differential display can be used to isolate full length clones of the corresponding gene. The full length coding portion of the gene can readily be isolated, without undue experimentation, by molecular biological techniques well known in the art. For example, the isolated differentially expressed amplified fragment can be labeled and used to screen a cDNA library. Alternatively, the labeled fragment can be used to screen a genomic library.

PCR technology can also be utilized to isolate full length cDNA sequences. As described above, the isolated, amplified gene fragments obtained through differential display have 5' terminal ends at some random point within the gene and have 3' terminal ends at a position preferably corresponding to the 3' end of the transcribed portion of the gene. Once nucleotide sequence information from an amplified fragment is obtained, the remainder of the gene (i.e., the 5' end of the gene, when utilizing differential display) can be obtained using, for example, RT-PCR.

In one embodiment of such a procedure for the identification and cloning of full length gene sequences, RNA can be isolated, following standard procedures, from an appropriate tissue or cellular source. A reverse transcription reaction can then be performed on the RNA using an oligonucleotide primer complimentary to the mRNA that corresponds to the amplified fragment, for the priming of first strand synthesis. Because the primer is anti-parallel to the mRNA, extension will proceed toward the 5' end of the mRNA. The resulting RNA/DNA hybrid can then be "tailed" with guanines using a standard terminal transferase reaction, the hybrid can be digested with RNAase H, and second strand synthesis can then be primed with a poly-C primer. Using the two primers, the 5' portion of the gene is amplified using PCR. Sequences obtained can then be isolated and recombined with previously isolated sequences to generate a full-length cDNA of the differentially expressed genes of the invention. For a review of cloning strategies and recombinant DNA techniques, see e.g., Sambrook et al., 1989, supra; and Ausubel et al., 1989, supra.

IX. Illustrative Compounds for the Activation of CPRE

In one embodiment, 1,3-bis-(substituted-phenyl)-2-propen-1-ones (chalcones) and similar compounds are used to activate CPRE, and thus induce the expression of a cytoprotective enzyme or the coordinate induction of such enzymes. These compounds are extensively described in U.S. patent application Ser. No. 09/886,348, incorporated herein by reference in its entirety. In a specific embodiment, the compound is 3-(5-benzo[b]thiophene-2-yl-2,4-dimethoxy-phenyl)-1-(3,4,5-trimethoxyphenyl)-propenone (Compound A). Other compounds can be identified easily using the instructions provided in detail in this specification.

In one nonlimiting embodiment, the invention provides the use of a compound of the formula (I) to induce CPRE activated gene products.

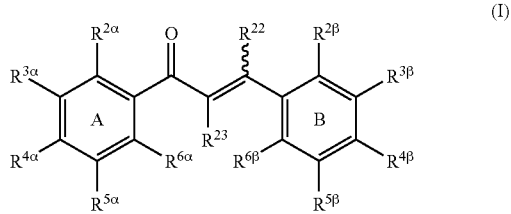

(I)

or its pharmaceutically acceptable salt, wherein:

i) the wavy line indicates that the compound can be in the form of the E or Z isomer;

ii) $R^{22}$ and $R^{23}$ are independently hydrogen or ($C_1$-$C_4$) alkyl;

iii) $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$, and $R^{6\beta}$ are independently iv) hydrogen, alkyl, carbocycle, aryl, heteroaryl, heterocycle, cycloalkyl, alkoxy, aryloxy, arylalkoxy, heteroaryloxy, heteroarylalkoxy, alkylthio, alkylamino, aminoalkyl, haloalkylthio, acyl, haloalkyl, aryloxy, amido, acylamino, amino, dialkylamino, aminodialkyl, trifluoroalkoxy, alkylsulfonyl, haloalkylsulfonyl, aminocarbonyl, alkenyl, alkynyl, halogen, hydroxyl, thiol, cyano, nitro, sulfonic acid, sulfonate, sulfate, sulfinic acid, sulfenic acid, sulfamide, sulfonamide, sulfoxide, metal sulfinate, phosphate, phosphonate, metal phosphonate, phosphinate, alditol, carbohydrate, amino acid, $OC(R^1)_2CO_2H$, $SC(R^1)_2CO_2H$, $NHCHR^1CO_2H$, $CO-R^2$, $CO_2R^1$, polyoxyalkylene, polyol alkyl, oxyalkylamino, alkylcarbonylalkyl, lower alkyl S(O)-lower alkyl, lower alkyl-S(O)$_2$-lower alkyl; hydroxyalkyl, aralkoxy, heteroaryl lower alkoxy, heterocyclo lower alkoxy, heteroaryloxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, any of which can be optionally substituted with a moiety that does not adversely affect the biological properties of the molecule; —C(O)(CH$_2$)$_2$CO$_2$$^-$M$^+$, —SO$_3$M$^+$, or -lower alkyl-O—R, wherein R is PO$_2$(OH)$^-$M$^+$, PO$_3$(OH)$^-$M$^+$ or —SO$_3$M$^+$, wherein M$^+$ is a pharmaceutically acceptable cation; -lower alkylcarbonyl-lower alkyl; carboxy lower alkyl; -lower alkylamino-lower alkyl; N,N-di-substituted amino lower alkyl-, wherein the substituents each independently represent lower alkyl;

v) $R^1$ is H, lower alkyl, an optionally substituted carbocycle, aryl, heteroaryl, heterocycle, alkylaryl, alkylheteroaryl, alkylheteroaryl or alkylheterocycle;

vi) $R^2$ is an optionally substituted alkyl, alkenyl, alkynyl, aryl, carbocycle, heteroaryl, heterocycle, alkylaryl, alkylheteroaryl, alkylheteroaryl or alkylheterocycle;

vii) alternatively, $R^{22}$ and $R^{6\alpha}$ or $R^{23}$ and $R^{6\alpha}$ can join together to form a bridged carbocycle, aryl, heterocycle or heteroaromatic;

viii) $R^{2\alpha}$ and $R^{3\alpha}$, $R^{3\alpha}$ and $R^{4\alpha}$, $R^{4\alpha}$ and $R^{5\alpha}$, $R^{5\alpha}$ and $R^{6\alpha}$, $R^{2\beta}$ and $R^{3\beta}$, $R^{3\beta}$ and $R^{4\beta}$, $R^{4\beta}$ and $R^{5\beta}$ or $R^{5\beta}$ and $R^{6\beta}$ can independently join to form a bridged compound selected from the group consisting of an optionally substituted carbocycle, an optionally substituted cycloalkenyl, an optionally substituted cycloalkylcarbonyl, an optionally substituted cycloalkenylcarbonyl; an optionally substituted aryl, an optionally substituted heterocyclic or an optionally substituted heteroaromatic, or alkylenedioxy or wherein the ring can include a carbonyl, cyclic ester, amide, amine, sulfonate, or phosphonate;

ix) at least one of $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ or $R^{6\beta}$ is, or $R^{2\alpha}$ and $R^{3\alpha}$, $R^{3\alpha}$ and $R^{4\alpha}$, $R^{4\alpha}$ and $R^{5\alpha}$, $R^{5\alpha}$ and $R^{6\alpha}$, $R^{2\beta}$ and $R^{3\beta}$, $R^{3\beta}$ and $R^{4\beta}$, $R^{4\beta}$ and $R^{5\beta}$ or $R^{5\beta}$ and $R^{6\beta}$ join together to be, an aryl, heterocycle or heteroaromatic; and x) at least one of $R^{2\alpha}$, $R^{3\alpha}$, $R^{4\alpha}$, $R^{5\alpha}$, or $R^{6\alpha}$, and at least one of $R^{2\beta}$, $R^{3\beta}$, $R^{4\beta}$, $R^{5\beta}$ or $R^{6\beta}$ is a substituent other than hydrogen.

In another embodiment, the compound is of the formula (II):

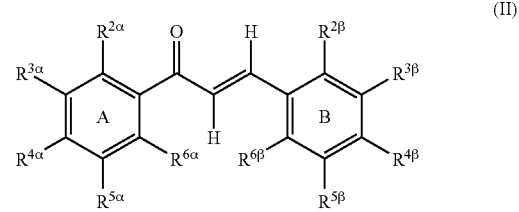

(II)

or its pharmaceutically acceptable salt.

In another embodiment, $R^1$ is independently H or lower alkyl, R2 is an optionally substituted alkyl; and at least one of $R^{2\alpha}$, $R^{3\alpha}$, $R^{4\alpha}$, $R^{5\alpha}$ or $R^{6\alpha}$ and at least one of $R^{2\beta}$, $R^{3\beta}$, $R^{4\beta}$, $R^{5\beta}$ or $R^{6\beta}$ is a substituent other than hydrogen.

In another embodiment, $R^{43\beta}$ or $R^{50\beta}$ is optionally substituted heteroaryl or heterocycle; and at least one of $R^{2\alpha}$, $R^{3\alpha}$, $R^{4\alpha}$, $R^{5\alpha}$, or $R^{6\alpha}$ is a substituent other than hydrogen.

In another embodiment, $R^{4\alpha}$ or $R^{5\alpha}$ is optionally substituted heteroaryl or heterocycle; and at least one of $R^{2\beta}$, $R^{3\beta}$, $R^{40\beta}$, $R^{5\beta}$, or $R^{6\beta}$ is a substituent other than hydrogen.

In a particular embodiment, $R^{5\beta}$ is optionally substituted thienyl or benzothienyl; $R^{2\alpha}$, $R^{3\alpha}$, $R^{4\alpha}$, $R^{5\alpha}$, $R^{6\alpha}$, or $R^{2\beta}$, $R^{3\beta}$, $R^{4\beta}$, and $R^{6\beta}$ are independently hydrogen, methoxy, ethoxy, propoxy, benzyloxy, 4-carboxybenzyloxy, 4-ethoxycarbonylbenzyloxy, 4-aminobenzyloxy, fluoro, chloro, bromo, iodo, hydroxy, $OCH_2CO_2H$, $SCH_2CO_2H$, $NHCH_2CO_2H$, $CO_2H$, pyrid-2-ylmethoxy, pyrid-3-ylmethoxy, pyrid-4-ylmethoxy; thien-2-ylmethoxy, thien-3-ylmethoxy, fur-2-ylmethoxy, fur-3-ylmethoxy and at least one of $R^{2\alpha}$, $R^{3\alpha}$, $R^{4\alpha}$, $R^{5\alpha}$, or $R^{6\alpha}$ is a substituent other than hydrogen.

In another embodiment, at least one of $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ or $R^{6\beta}$, is or $R^{2\alpha}$ and $R^{3\alpha}$, $R^{3\alpha}$ and $R^{4\alpha}$, $R^{4\alpha}$ and $R^{5\alpha}$, $R^{5\alpha}$ and $R^{6\alpha}$, $R^{2\beta}$ and $R^{3\beta}$, $R^{3\beta}$ and $R^{4\beta}$, $R^{4\beta}$ and $R^{5\beta}$ or $R^{5\beta}$ and $R^{6\beta}$ join to form a carbocycle, aryl, heterocycle or heteroaromatic in which the carbocycle, aryl, heteroaryl or heterocycle is a 5, 6 or 7 membered ring, optionally conjugated to another carbocycle, aryl, heteroaryl or heterocycle.

In one embodiment, the heteroaryl group is not an oxazole.

In yet another embodiment, either $R^{3\alpha}$ and $R^{4\alpha}$ or $R^{5\alpha}$ and $R^{4\alpha}$ join to form a 5-membered methylendioxyphenyl group.

In one alternative embodiment, one of the A or B rings has only hydrogen substituents. In another alternative embodiment, both of the A or B rings have only hydrogen substituents. In yet another embodiment, one or both of the rings have non-hydrogen substituents that are limited to non-aryl, non-heterocycle or non-heteroaromatic moieties.

Examples of active chalcone derivatives prepared in this invention are listed in Table 2.

TABLE 2

| X | Z |
|---|---|
| 4-carboxymethoxy-3,5-dimethoxy, sodium salt | 2,4-dimethoxy-5-(benzo[b]thien-2-yl) |
| 2,4,6-trimethoxy | 2,4-difluoro |
| 2,3-dichloro-4-methoxy | 5-bromo-2-methoxy |
| 2,4,6-trimethoxy | 4-hydroxy-3,5-dimethoxy |
| 3,5-dimethoxy-4-(4-methoxybenzyloxy) | 3,4,5-trimethoxy |
| 3,4,5-trimethoxy | 5-bromo-2-methoxy |
| 2,3,4-trimethoxy | 3-bromo-4,5-dimethoxy |
| 3,4,5-trimethoxy | 3,4-dimethoxy-5-phenyl |
| 4-hydroxy-3,5-dimethoxy | 2,4-dimethoxy-5-(benzo[b]thien-2-yl) |
| 4-carboxymethoxy-3,5-dimethoxy | 2,4-dimethoxy-5-(benzo[b]thien-2-yl) |
| 2,3,4-trimethoxy | 5-(benzo[b]thien-2-yl)-3,4-dimethoxy |
| 3,4,5-trimethoxy | 2-methoxy-5-(4-methylthien-2-yl) |

TABLE 2-continued

| X | Z |
|---|---|
| 3,4-dimethoxy | 2-methoxy-5-(5-methylthien-2-yl) |
| 3,4,5-trimethoxy | 2-methoxy-5-(5-methylthien-2-yl) |
| 3,5-dimethoxy-4-(1,4-benzodioxan-3-methoxy) | 3,4,5-trimethoxy |
| 2,5-dimethoxy | 2-methoxy-5-(thien-2-yl) |
| 3,4,5-trimethoxy | 3,4-dimethoxy-5-(thien-2-yl) |
| 3,4-dichloro-2-hydroxy, sodium salt | 2-methoxy-5-(thien-2-yl) |
| 3,4-dimethoxy | 2-methoxy-5-(4-methylthien-2-yl) |
| 3,4,5-trimethoxy | 3,4-dimethoxy-5-(3-pyridyl) |
| 3,4,5-trimethoxy | 2,4-dimethoxy-5-(thien-2-yl) |
| 3,4,5-trimethoxy | 5-bromo-2,4-dimethoxy |
| 3,5-dimethoxy | 2-methoxy-5-(thien-2-yl) |
| 4-iodo-2-methoxy | 2-methoxy-5-(thien-2-yl) |
| 4-(3,4-dimethoxybenzyloxy)-3-methoxy | 3,4,5-trimethoxy |
| 4-(3,4-dimethoxybenzyloxy)-3,5-dimethoxy | 3,4,5-trimethoxy |
| 2,4,5-trimethoxy | 3,4,5-trimethoxy |
| 3,4,5-trimethoxy | 2-bromo-4,5-dimethoxy |
| 3,4-dichloro-2-hydroxy | 5-bromo-2-methoxy |
| 3-methoxy-4-(3,4,5-trimethoxybenzyloxy) | 3,4,5-trimethoxy |
| 3-methoxy-4-(4-pyridylmethoxy), hydrogen chloride | 2-methoxy-5-(thien-2-yl) |
| 3-methoxy-4-(2-pyridylmethoxy), hydrogen chloride | 2-methoxy-5-(thien-2-yl) |
| 2-methoxy-4-(thien-2-yl) | 3,4-difluoro |
| 3,4,5-trimethoxy | 5-benzo[b]thien-2-yl)-2-methoxy |
| 3,4-dichloro-2-hydroxy | 2-methoxy-5-(thien-2-yl) |
| 3,4-dimethoxy | 5-(benzo[b]thien-2-yl)-2-methoxy |
| 2,3,4-trimethoxy | 2,4-dimethoxy-5-(thien-2-yl) |
| 3-methoxy-4-(2-pyridylmethoxy) | 2-methoxy-5-(thien-2-yl) |
| 4-(fur-2-ylmethoxy)-3,5-dimethoxy | 3,4,5-trimethoxy |
| 4-iodo-2-methoxy | 3,4,5-trimethoxy |
| 2,4,6-trimethoxy | 3-bromo-4,5-dimethoxy |
| 3,4-methylenedioxy | 2-methoxy-5-(5-methylthien-2-yl) |
| 4-hydroxy-3,5-dimethoxy, sodium salt | 2,4-dimethoxy-5-(benzo[b]thien-2-yl) |
| 3-methoxy-4-(3-pyridylmethoxy) | 2-methoxy-5-(thien-2-yl) |
| 4-methoxy | 5-(benzo[b]thien-2-yl)-2-methoxy |
| 3,5-dimethoxy-4-(3,4-methylenedioxybenzyloxy) | 3,4,5-trimethoxy |
| 3,5-dimethoxy-4-(thien-2-ylmethoxy) | 3,4,5-trimethoxy |
| 3,4,5-trimethoxy | 3-fluoro-4-methoxy |
| 3,4-dimethoxy | 3-bromo-4,5-dimethoxy |
| 2,3,4-trimethoxy | 3,4-dimethoxy-5-(thien-2-yl) |
| 3,5-dimethoxy-4-(3,4,5-trimethoxybenzyloxy) | 3,4,5-trimethoxy |
| 3,4,5-trimethoxy | 5-(5-acetylthien-2-yl)3,4-dimethoxy |
| 4-methoxy | 2-methoxy-5-(thien-2-yl) |
| 2,6-dimethoxy | 2-methoxy-5-(thien-2-yl) |
| 3,4-dimethoxy | 2-methoxy-5-(thien-2-yl) |
| 2,4,6-trimethoxy | 2-methoxy-5-(thien-2-yl) |
| 3,4,5-trimethoxy | 2-methoxy-5-(thien-2-yl) |
| 5-(2,4-dimethoxyphenyl) | 3,4,5-trimethoxy |
| 2-bromo-4,5-dimethoxy | 2-bromo-4,5-dimethoxy |
| 3,4,5-trimethoxy | 4-hydroxy |
| 3-methoxy-4-(4-methoxybenzyloxy) | 3,4,5-trimethoxy |
| 4-(4-ethoxycarbonyl-benzyloxy)-3-methoxy | 2-methoxy-5-(thien-2-yl) |
| 4-(2,3-isopropylidenedioxy-1-propoxy)-3,5-dimethoxy | 5-(benzo[b]thien-2-yl)-2,4-dimethoxy |

TABLE 2-continued

[Structure: chalcone with X-substituted phenyl — C(=O)—CH=CH— Z-substituted phenyl]

| X | Z |
|---|---|
| 3-methoxy-4-(4-pyridylmethoxy) | 2-methoxy-5-(thien-2-yl) |
| 4-(3-acetylphenyl)-2-methoxy | 3,4,5-trimethoxy |
| 3,4,5-trimethoxy | 3-bromo-4,5-dimethoxy |
| 3,4-methylenedioxy | 5-bromo-2-methoxy |
| 3,4-methylenedioxy | 2-methoxy-5-(thien-2-yl) |
| 3,4-methylenedioxy | 2-methoxy-5-(4-methylthien-2-yl) |
| 2-methoxy-5-(thien-2-yl) | 4-ethoxy-3-fluoro |
| 3,4,5-trimethoxy | 5-(benzo[b]thien-2-yl)-2-carboxymethoxy-4-methoxy, sodium salt |
| 3,4,5-trimethoxy | 5-(benzo[b]thien-2-yl)-3,4-dimethoxy |
| 3,4,5-trimethoxy | 5-(benzo[b]thien-2-yl)-2,4-dimethoxy |
| 4-(4-carboxybenzyloxy)-3-methoxy | 2-methoxy-5-(thien-2-yl) |
| 3,5-dimethoxy-4-(2-methoxyethoxy) | 3,4,5-trimethoxy |
| 2,3,4-trimethoxy | 5-(4-formylphenyl)-3,4-dimethoxy |
| 2,4-dimethoxy | 4-trifluoromethyl |
| 3,4-difluoro | 2-methoxy-5-(thien-2-yl) |
| 3,4,5-trimethoxy | hydrogen |
| 4-(3-chlorophenyl) | 3,4,5-trimethoxy |
| 3,4,5-trimethoxy | 4-(thien-2-yl) |
| 5-(3-chlorophenyl)-2,4-dimethoxy | 3,4,5-trimethoxy |
| 4-(4-aminobenzyloxy)-3-methoxy | 2-methoxy-5-(thien-2-yl) |
| 3-methoxy-4-(3,4-methylenedioxybenzyloxy) | 3,4,5-trimethoxy |
| 4-hydroxy-3-methoxy | 2-methoxy-5-(thien-2-yl) |
| 2,3,4-trimethoxy | 5-(benzo[b]thien-2-yl)-2,4-dimethoxy |
| 3,4,5-trimethoxy | 5-(benzo[b]thien-2-yl)-2-carboxymethoxy-4-methoxy |
| 3,5-di-tert-butyl-4-methoxy | hydrogen |
| 3,5-dimethoxy-4-(2-morpholinoethoxy) | 5-(benzo[b]thien-2-yl)-2,4-dimethoxy |
| 2-methoxy-4-(3-methoxyphenyl) | 2-methoxy-5-(thien-2-yl) |
| 3,4-dimethoxy | 5-(benzo[b]thien-2-yl)-2,4-dimethoxy |
| 3,4,5-trimethoxy | 4-bromo |
| 2,5-dimethoxy-4-(thien-2-yl-methoxy) | 2-methoxy-5-(thien-2-yl) |
| 3,4-dimethoxy | 4-(thien-2-yl) |
| 2,4-dihydroxy | 4-hydroxy |
| 5-bromo-2,4-dimethoxy | 3,4,5-trimethoxy |
| 2,4,5-triethoxy | 3-bromo-4,5-dimethoxy |
| 4-methoxy | 3,4-dimethoxy |
| 2-methoxy-4-(thien-2-yl) | 2-methoxy-4-(thien-2-yl) |
| 3,5-di-tert-4-methoxy | 4-methoxy |
| hydrogen | hydrogen |
| 4-fluoro | 4-fluoro |
| hydrogen | 4-nitro |
| 4-methoxy | hydrogen |
| 3,4-dichloro-2-hydroxy | 5-(benzo[b]thien-2-yl)-2-methoxy |
| 3-chloro | hydrogen |
| 3,5-di-tert-butyl-4-hydroxy | 4-methoxy |
| 4-methyl | 3,5-di-tert-butyl-4-hydroxy |
| hydrogen | 3,5-di-tert-butyl-4-hydroxy |
| 3-methoxy-4-(4-tert-butyloxycarbonylaminobenzyloxy) | 2-methoxy-5-(thien-2-yl) |
| hydrogen | 2,4,6-triisopropyl |
| 4-bromo | 3,4,5-trimethoxy |
| 4-benzyloxy-3,5-dimethoxy | 3-bromo-4,5-dimethoxy |
| 3,5-dimethoxy-4- | 5-(benzo[b]thien-2-yl)-2,4-dimethoxy |

TABLE 2-continued

[Structure: chalcone with X-substituted phenyl — C(=O)—CH=CH— Z-substituted phenyl]

| X | Z |
|---|---|
|   | [Structure: bicyclic lactone with isopropylidene dioxolane and CH₂O— linkage] |

Alternative embodiments include the compounds illustrated below, or their pharmaceutically acceptable salts, wherein the variables are as defined above.

[Structure 1: chalcone with $R^{2\alpha}$, $R^{3\alpha}$, $R^{4\alpha}$, $R^{5\alpha}$, $R^{6\alpha}$ substituted phenyl on left; right ring has 2-OCH₃, 4-OCH₃, and 5-(benzo[b]thien-2-yl)]

[Structure 2: chalcone with $R^{2\alpha}$, $R^{3\alpha}$, $R^{5\alpha}$, $R^{6\alpha}$ on left phenyl bearing 4-OCH₂COOH (HOOC-CH₂-O-); right ring has 2-OCH₃, 4-OCH₃, and 5-(benzo[b]thien-2-yl)]

[Structure 3: chalcone with $R^{2\alpha}$, $R^{3\alpha}$, $R^{5\alpha}$, $R^{6\alpha}$ on left phenyl bearing 4-OH; right ring has 2-OMe, 4-OMe, and 5-(benzo[b]thien-2-yl)]

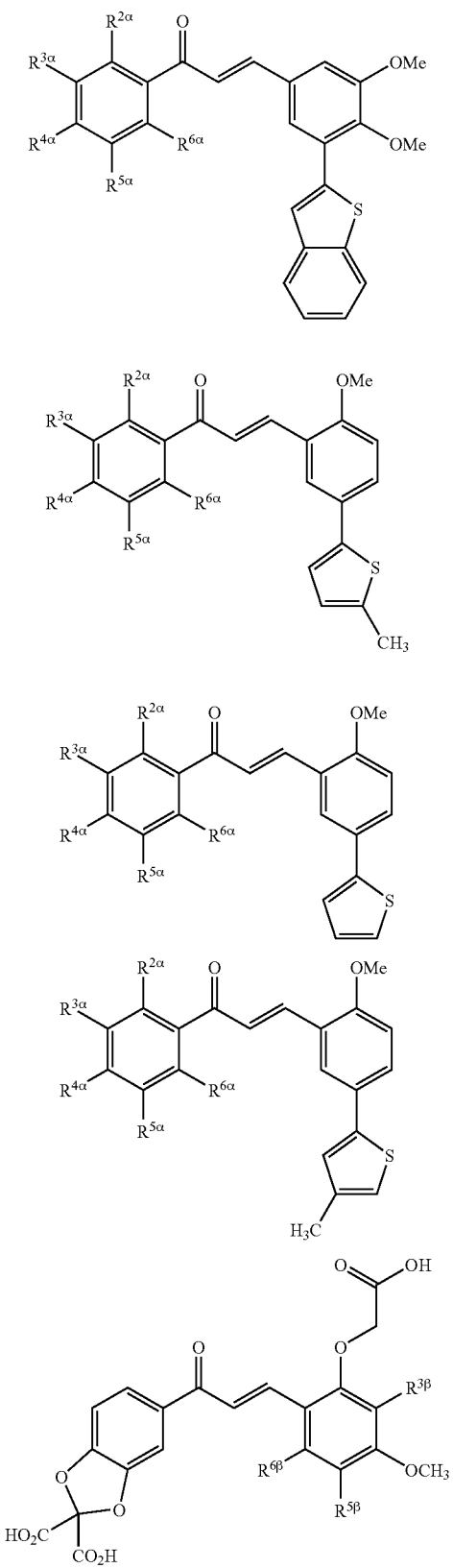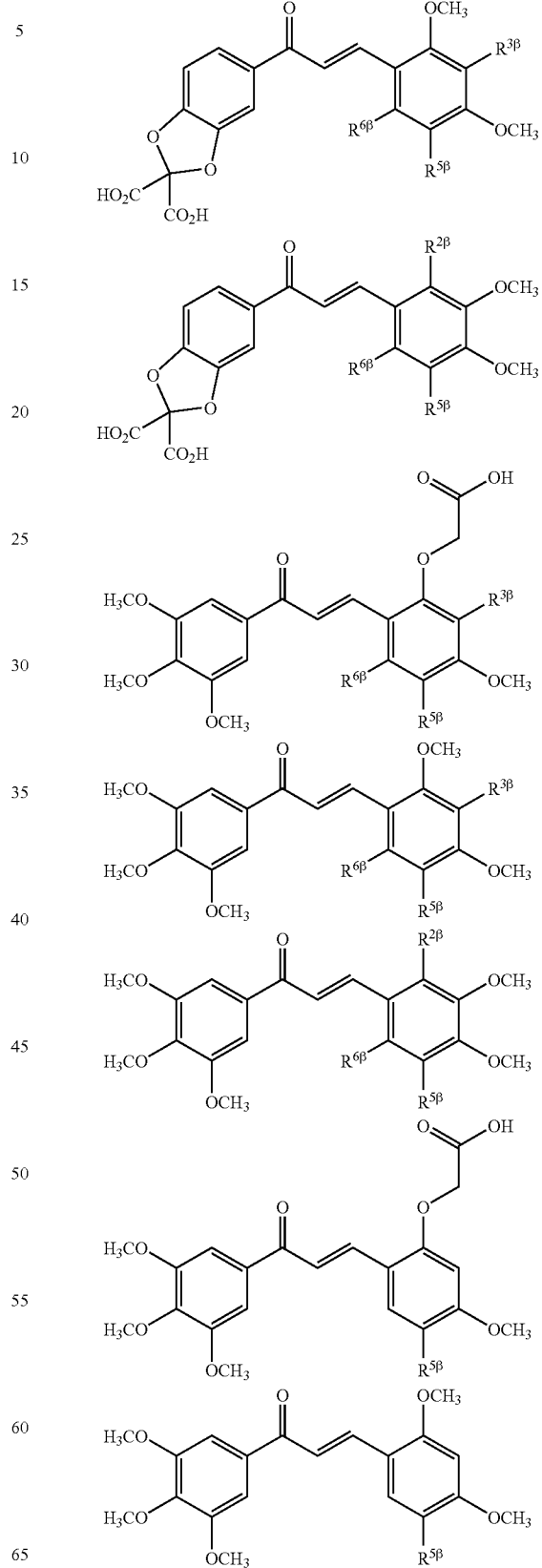

-continued

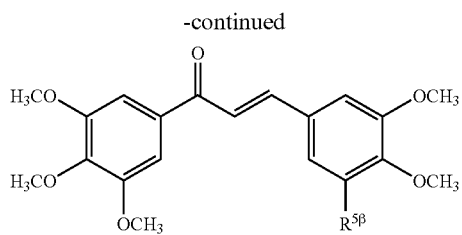

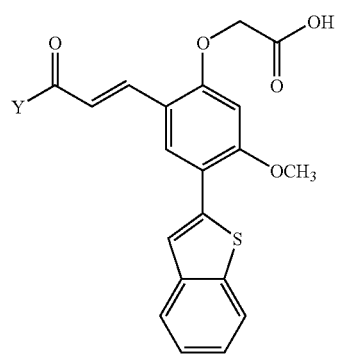

wherein Y is a phenyl ring conjugated to another heteroaromatic or heterocycle.

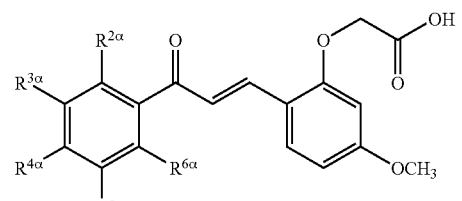

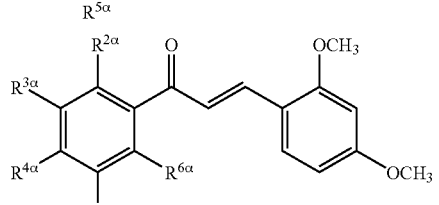

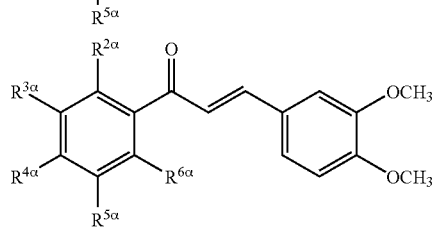

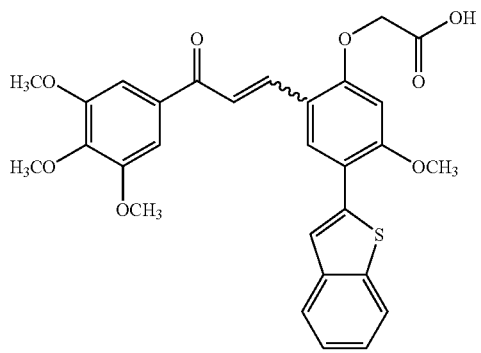

-continued

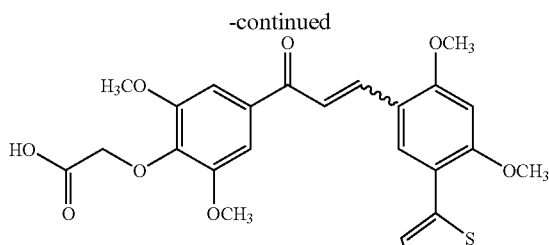

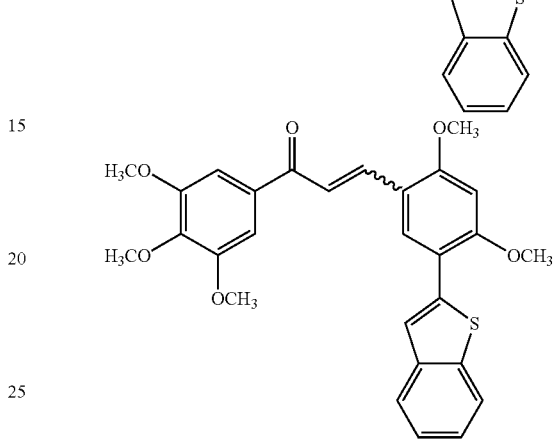

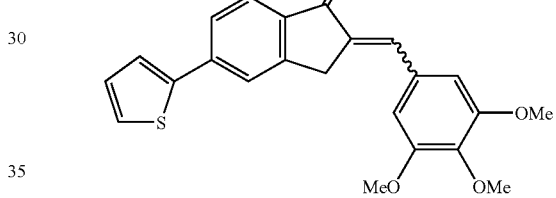

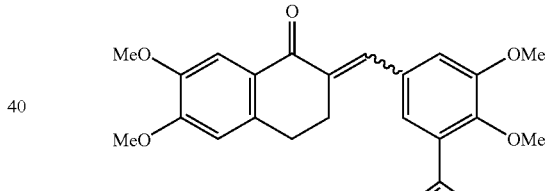

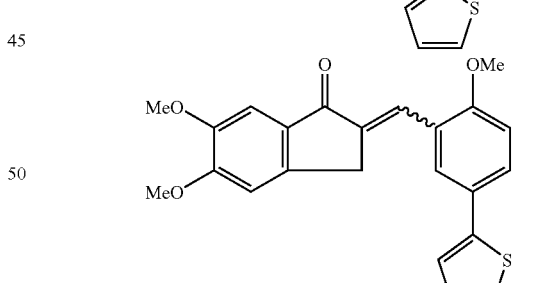

In yet another embodiment, the compound is selected from the following:

3-[5-(benzo[b]thien-2-yl)-2,4-dimethoxyphenyl]-1-(4-carboxymethoxy-3,5-dimethoxyphenyl)-2-propen-1-one sodium salt;

3-[2,4-dimethoxy-5-(thien-2-yl)phenyl]-1-(4-carboxymethoxy-3,5-dimethoxyphenyl)-2-propen-1-one;

3-[2,4-dimethoxy-5-(thien-2-yl)phenyl]-1-(4-carboxymethoxy-3,5-dimethoxyphenyl)-2-propen-1-one sodium salt;

3-[5-(benzo[b]thien-2-yl)-2,4-dimethoxyphenyl]-1-(4-hydroxy-3,5-dimethoxyphenyl)-2-propen-1-one;

3-[2,4-dimethoxy-5-(thien-2-yl)phenyl]-1-(4-hydroxy-3,5-dimethoxyphenyl)-2-propen-1-one;

3-[5-(benzo[b]thien-2-yl)-2,4-dimethoxyphenyl]-1-(4-carboxymethoxy-3,5-dimethoxyphenyl)-2-propen-1-one;

3-[2,4-dimethoxy-5-(thien-2-yl)-phenyl]-1-(4-carboxymethoxy-3,5-dimethoxyphenyl)-2-propen-1-one;

3-[5-(benzo[b]thien-2-yl)-3,4-dimethoxyphenyl]-1-(2,3,4-trimethoxyphenyl)-2-propen-1-one;

3-[2-methoxy-5-(4-methylthien-2-yl)phenyl]-1-(3,4,5-trimethoxy phenyl)-2-propen-1-one;

3-[2-methoxy-5-(5-methylthien-2-yl)phenyl]-1-(3,4-dimethoxyphenyl)-2-propen-1-one;

3-[2-methoxy-5-(5-methylthien-2-yl)phenyl]-1-(3,4,5-trimethoxy phenyl)-2-propen-1-one;

3-[2-methoxy-5-(thien-2-yl)phenyl]-1-(2,5-dimethoxyphenyl)-2-propen-1-one;

3-[3,4-dimethoxy-5-(thien-2-yl)phenyl]-1-(3,4,5-trimethoxyphenyl)-2-propen-1-one;

3-[2-methoxy-5-(thien-2-yl)phenyl]-1-(3,4-dichloro-2-hydroxyphenyl)-2-propen-1-one sodium salt;

3-[2-methoxy-5-(4-methylthien-2-yl)phenyl]-1-(3,4-dimethoxyphenyl)-2-propen-1-one;

3-[3,4-dimethoxy-5-(3-pyridyl)phenyl]-1-(3,4,5-trimethoxyphenyl)-2-propen-1-one;

3-[2,4-dimethoxy-5-(thien-2-yl)phenyl]-1-(3,4,5-trimethoxyphenyl)-2-propen-1-one;

3-[2-methoxy-5-(thien-2-yl)phenyl]-1-(3,5-dimethoxyphenyl)-2-propen-1-one;

3-[2-methoxy-5-(thien-2-yl)phenyl]-1-(4-iodo-2-methoxyphenyl)-2-propen-1-one;

3-[2-methoxy-5-(thien-2-yl)phenyl]-1-(3-methoxy-4-(4-pyridylmethoxyphenyl)-2-propen-1-one, hydrochloride salt;

3-[2-methoxy-5-(thien-2-yl)phenyl]-1-(3-methoxy-4-(2-pyridylmethoxyphenyl)-2-propen-1-one hydrochloride salt;

3-(3,4-difluorophenyl)-1-[2-methoxy-4-(thien-2-yl)phenyl]-2-propen-1-one;

3-[5-(benzo[b]thien-2-yl)-2-methoxyphenyl]-1-(3,4,5-trimethoxyphenyl)-2-propen-1-one;

3-[2-methoxy-5-(thien-2-yl)phenyl]-1-(3,4-dichloro-2-hydroxyphenyl)-2-propen-1-one;

3-[5-(benzo[b]thien-2-yl)-2-methoxyphenyl]-1-(3,4-dimethoxyphenyl)-2-propen-1-one;

3-[2,4-dimethoxy-5-(thien-2-yl)phenyl]-1-(2,3,4-trimethoxyphenyl)-2-propen-1-one;

3-[2-methoxy-5-(thien-2-yl)phenyl]-1-(3-methoxy-4-(2-pyridylmethoxyphenyl)-2-propen-1-one;

3-[2-methoxy-5-(5-methylthien-2-yl)phenyl]-1-(3,4-methylenedioxyphenyl)-2-propen-1-one;

3-[5-(benzo[b]thien-2-yl)-2,4-dimethoxyphenyl]-1-(4-hydroxy-3,5-dimethoxyphenyl)-2-propen-1-one sodium salt;

3-[2-methoxy-5-(thien-2-yl)phenyl]-1-(3-methoxy-4-(3-pyridylmethoxphenyl)-2-propen-1-one;

3-[5-(benzo[b]thien-2-yl)-2-methoxyphenyl]-1-(4-methoxyphenyl)-2-propen-1-one;

3-[3,4-dimethoxy-5-(thien-2-yl)phenyl]-1-(2,3,4-trimethoxyphenyl)-2-propen-1-one;

3-[5-(5-acetylthien-2-yl)-3,4-dimethoxyphenyl]-1-(3,4,5-trimethoxyphenyl)-2-propen-1-one;

3-[2-methoxy-5-(thien-2-yl)phenyl]-1-(4-methoxyphenyl)-2-propen-1-one;

3-[2-methoxy-5-(thien-2-yl)phenyl]-1-(2,6-dimethoxyphenyl)-2-propen-1-one;

3-[2-methoxy-5-(thien-2-yl)phenyl]-1-(3,4-dimethoxyphenyl)-2-propen-1-one;

3-[2-methoxy-5-(thien-2-yl)phenyl]-1-(2,4,6-trimethoxyphenyl)-2-propen-1-one;

3-[2-methoxy-5-(thien-2-yl)phenyl]-1-(3,4,5-trimethoxyphenyl)-2-propen-1-one;

3-[2-methoxy-5-(thien-2-yl)phenyl]-1-[4-(4-ethoxycarbonylenzyloxy)-3-methoxyphenyl]-2-propen-1-one;

3-[5-(benzo[b]thien-2-yl)-2,4-dimethoxyphenyl]-1-[4-(2,3-isopropylidenedioxy-1-propoxy)-3,5-dimenthoxypheny]-2-propen-1-one;

3-[2-methoxy-5-(thien-2-yl)phenyl]-1-[3-methoxy-4-(4-pyridylmethoxy)phenyl]-2-propen-1-one;

3-[2-methoxy-5-(thien-2-yl)phenyl]-1-(3,4-methylenedioxyphenyl)-2-propen-1-one;

3-[2-methoxy-5-(4-methylthien-2-yl)phenyl]-1-(3,4-methylenedioxyphenyl)-2-propen-1-one;

3-(4-ethoxy-3-fluorophenyl)-1-[2-methoxy-5-(thien-2-yl)phenyl]-2-propen-1-one;

3-[5-(benzo[b]thien-2-yl)-2-carboxymethoxy-4-methoxyphenyl]-1-(3,4,5-trimethoxyphenyl)-2-propen-1-one sodium salt;

3-[5-(benzo[b]thien-2-yl)-4-carboxymethoxy-2-methoxyphenyl]-1-(3,4,5-trimethoxyphenyl)-2-propen-1-one;

3-[5-(benzo[b]thien-2-yl)-4-carboxymethoxy-2-methoxyphenyl]-1-(3,4,5-trimethoxyphenyl)-2-propen-1-one sodium salt;

3-[2-carboxymethoxy-4-methoxy-5-(thien-2-yl)phenyl]-1-(3,4,5-trimethoxyphenyl)-2-propen-1-one;

3-[2-carboxymethoxy-4-methoxy-5-(thien-2-yl)phenyl]-1-(3,4,5-trimethoxyphenyl)-2-propen-1-one sodium salt;

3-[4-carboxymethoxy-2-methoxy-5-(thien-2-yl)phenyl]-1-(3,4,5-trimethoxyphenyl)-2-propen-1-one sodium salt;

3-[4-carboxymethoxy-2-methoxy-5-(thien-2-yl)phenyl]-1-(3,4,5-trimethoxyphenyl)-2-propen-1-one;

3-[5-(benzo[b]thien-2-yl)-3,4-dimethoxyphenyl]-1-(3,4,5-trimethoxyphenyl)-2-propen-1-one;

3-[5-(benzo[b]thien-2-yl)-2,4-dimethoxyphenyl]-1-(3,4,5-trimethoxyphenyl)-2-propen-1-one;

3-[5-(benzo[b]thien-2-yl)-2,4-dimethoxyphenyl]-1-(3,4,5-trimethoxyphenyl)-2-buten-1-one;

3-[2-methoxy-5-(thien-2-yl)phenyl]-1-[4-(4-carboxybenzyloxy)-3-methoxyphenyl]-2-propen-1-one;

3-[2-methoxy-5-(thien-2-yl)phenyl]-1-(3,4-difluorophenyl)-2-propen-1-one;

3-[4-(thien-2-yl)phenyl]-1-(3,4,5-trimethoxyphenyl)-2-propen-1-one;

3-[2-methoxy-5-(thien-2-yl)phenyl]-1-[4-(4-aminobenzyloxy)-3-methoxyphenyl]-2-propen-1-one;

3-[2-methoxy-5-(thien-2-yl)phenyl]-1-(4-hydroxy-3-methoxyphenyl)-2-propen-1-one;

3-[5-(benzo[b]thien-2-yl)-2,4-dimethoxyphenyl]-1-(2,3,4-trimethoxyphenyl)-2-propen-1-one;

3-[5-(benzo[b]thien-2-yl)-2-carboxymethoxy-4-methoxyphenyl]-1-(3,4,5-trimethoxyphenyl)-2-propen-1-one;

3-[5-(benzo[b]thien-2-yl)-2,4-dimethoxyphenyl]-1-[3,5-dimethoxy-4-(2-morpholinoethoxy)phenyl]-2-propen-1-one;

3-[2-methoxy-5-(thien-2-yl)phenyl]-1-[2-methoxy-4-(3-methoxyphenyl)phenyl]-2-propen-1-one;

3-[5-(benzo[b]thien-2-yl)-2,4-dimethoxyphenyl]-1-(3,4-dimethoxyphenyl)-2-propen-1-one;

3-[2-methoxy-5-(thien-2-yl)phenyl]-1-(2,5-dimethoxy-4-(thien-2-ylmethoxy)phenyl)-2-propen-1-one;

3-[4-(thien-2-yl)phenyl]-1-(3,4-dimethoxyphenyl)-2-propen-1-one;

3-[2-methoxy-4-(thien-2-yl)-phenyl]-1-[2-methoxy-4-(thien-2-yl)phenyl)-2-propen-1-one phenyl]-2-propen-1-one;

2-[[3,4-dimethoxy-5-(thien-2-yl)phenyl]ethylene]-3,4-dihydro-6,7-dimethoxy-1(2H)-naphthalenone.

The term alkyl, as used herein, unless otherwise specified, refers to a saturated straight, branched, or cyclic, primary, secondary, or tertiary hydrocarbon, including but not limited to those of $C_1$ to $C_{10}$, and preferably $C_1$-$C_4$, including methyl, ethyl, propyl, isopropyl, cyclopropyl, methylcyclopropyl, butyl, isobutyl, t-butyl, sec-butyl, cyclobutyl, and (cyclopropyl)methyl. The alkyl group specifically includes fluorinated alkyls such as $CF_3$ and other halogenated alkyls such as $CH_2CF_2$, $CF_2CF_3$, the chloro analogs and the like.

The alkyl group can be optionally substituted with one or more moieties selected from the group consisting of aryl, heteroaryl, heterocyclic, carbocycle, alkoxy, heterocycloxy, heterocylalkoxy, aryloxy; arylalkoxy; heteroaryloxy; heteroarylalkoxy, carbohydrate, amino acid, amino acid esters, amino acid amides, alditol, halo, haloalkyl, hydroxyl, carboxyl, acyl, acyloxy, amino, amido, alkylamino, dialkylamino, arylamino, nitro, cyano, thiol, imide, sulfonic acid, sulfate, sulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide, substituted or unsubstituted urea connected through nitrogen including but not limited to $NHCONH_2$ and NHCONHR; or any other desired functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term aryl, as used herein, and unless otherwise specified, refers to phenyl, biphenyl, or naphthyl, and preferably phenyl. The aryl group can be optionally substituted with one or more of the moieties selected from the group consisting of alkyl, heteroaryl, heterocyclic, carbocycle, alkoxy, aryloxy, aryloxy; arylalkoxy; heteroaryloxy; heteroarylalkoxy, carbohydrate, amino acid, amino acid esters, amino acid amides, alditol, halo, haloalkyl, hydroxyl, carboxyl, acyl, acyloxy, amino, amido, alkylamino, dialkylamino, arylamino, nitro, cyano, thiol, imide, sulfonic acid, sulfate, sulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide or any other desired functional group that does not inhibit the pharmacological activity of this compound, either unprotected, or protected as necessary, as known to those skilled in the art, for example, as taught in Greene, et al., "Protective Groups in Organic Synthesis," John Wiley and Sons, Second Edition, 1991. Alternatively, adjacent groups on the aryl ring can combine to form a 5 to 7 membered carbocyclic, aryl, heteroaryl or heterocyclic ring. In another embodiment, the aryl ring is substituted with an optionally substituted cycloalkyl (such as cyclopentyl or cyclohexyl), or an alkylene dioxy moiety (for example methylenedioxy).

The term heterocyclic refers to a nonaromatic cyclic group that can be partially (contains at least one double bond) or fully saturated and wherein there is at least one heteroatom, such as oxygen, sulfur, nitrogen, or phosphorus in the ring. The term heteroaryl or heteroaromatic, as used herein, refers to an aromatic that includes at least one sulfur, oxygen, nitrogen or phosphorus in the aromatic ring. Non-limiting examples of heterocyclics and heteroaromatics are pyrrolidinyl, tetrahydrofuryl, piperazinyl, piperidinyl, morpholino, thiomorpholino, tetrahydropyranyl, imidazolyl, pyrolinyl, pyrazolinyl, indolinyl, dioxolanyl or 1,4-dioxanyl. aziridinyl, furyl, furanyl, pyridyl, pyrimidinyl, benzoxazolyl, 1,2,4-oxadiazolyl, 1,3,4-oxadiazolyl, 1,3,4-thiadiazole, indazolyl, 1,3,5-triazinyl, thienyl, isothiazolyl, imidazolyl, tetrazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, benzothiazolyl, isothiazolyl, 1,2,4-thiadiazolyl, isooxazolyl, pyrrolyl, quinazolinyl, cinnolinyl, phthalazinyl, xanthinyl, hypoxanthinyl, pyrazole, imidazole, 1,2,3-triazole, 1,2,4-triazole, 1,2,3-oxadiazole, thiazine, pyridazine, or pteridinyl wherein said heteroaryl or heterocyclic group can be optionally substituted with one or more substituent selected from the same substituents as set out above for aryl groups. Functional oxygen and nitrogen groups on the heteroaryl group can be protected as necessary or desired. Suitable protecting groups can include trimethylsilyl, dimethylhexylsilyl, t-butyldimethylsilyl and t-butyldiphenylsilyl, trityl or substituted trityl, alkyl groups, acyl groups such as acetyl and propionyl, methanesulfonyl, and p-toluenesulfonyl.

The term thienyl refers to a five member cyclic group wherein the ring contains one sulfur atom and two double bonds. The thienyl group can optionally be substituted with one or more moieties selected from the group consisting of those described above for aryl substituents.

The term benzothienyl refers to a five member cyclic group wherein the ring contains one sulfur atom and two double bonds fused to a phenyl ring. The benzothienyl group can optionally be substituted with one or more moieties selected from the group consisting of those described above for aryl substituents.

The term aralkyl, as used herein, and unless otherwise specified, refers to an aryl group as defined above linked to the molecule through an alkyl group as defined above. The aryl and alkyl portions can be optionally substituted as described above.

The term heteroaralkyl, as used herein, and unless otherwise specified, refers to an heteroaryl group as defined above linked to the molecule through an alkyl group as defined above.

The term heterocyclealkyl, as used herein, refers to a heterocyclic group bound to the molecule through an alkyl group. The heterocyclic group and the alkyl group can be optionally substituted as described above.

The term aryloxy, as used herein, refers to an aryl group bound to the molecule through an oxygen atom. The aryl group can be optionally substituted as set out above for aryl groups.

The term heteroaryloxy, as used herein, refers to a heteroaryl group bound to the molecule through an oxygen atom. The heteroaryl group can be optionally substituted as set out above for aryl groups.

The term aralkoxy refers to an aryl group attached to an alkyl group that is attached to the molecule through an oxygen atom. The aryl and alkyl groups can be optionally substituted as described above.

The term heterocyclearalkoxy refers to a heterocyclic group attached to an aryl group attached to an alkyl-O— group. The heterocyclic, aryl and alkyl groups can be optionally substituted as described above.

The term halo or halogen, as used herein, includes chloro, bromo, iodo and fluoro.

The term alkoxy, as used herein, and unless otherwise specified, refers to a moiety of the structure —O-alkyl, wherein alkyl is as defined above. The alkyl group can be optionally substituted as described above. Alkoxy groups can include $OCF_3$, $OCH_2CF_3$, $OCF_2CF_3$ and the like.

The term alkylthio as used herein refers to an alkyl group attached to the molecule through a sulfur atom. The alkyl group can be optionally substituted as described above.

The term acyl, as used herein, refers to a group of the formula C(O)R', wherein R' is an alkyl, aryl, alkaryl or aralkyl group, or substituted alkyl, aryl, aralkyl or alkaryl, wherein these groups are as defined above.

The term "alditol," as referred to herein, and unless otherwise specified, refers to a carbohydrate in which the aldehyde or ketone group has been reduced to an alcohol moiety. The alditols of the present invention can also be optionally substituted or deoxygenated at one or more positions. Exemplary substituents include hydrogen, halo, haloalkyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, amino acid, amino acid esters and amides, phosphonyl, phosphinyl, phosphoryl, thioester, thioether, oxime, hydrazine, carbamate, phosphonic acid, phosphonate, or any other viable functional group that does not inhibit the pharmacological activity of this compound. Particular exemplary substituents include amine and halo, particularly fluorine. The substituent or alditol can be either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The alditol can have 3, 4, 5, 6 or 7 carbons. Examples of useful alditols are those derived from reduction of monosaccharides, including specifically those derived from the reduction of pyranose and furanose sugars.

The term "carbohydrate," as referred to herein, and unless otherwise specified, refers to a compound of carbon, hydrogen and oxygen that contains an aldehyde or ketone group in combination with at least two hydroxyl groups. The carbohydrates of the present invention can also be optionally substituted or deoxygenated at one or more positions. Carbohydrates thus include substituted and unsubstituted monosaccharides, disaccharides, oligosaccharides, and polysaccharides. The saccharide can be an aldose or ketose, and can comprise 3, 4, 5, 6, or 7 carbons. In one embodiment the carbohydrates are monosaccharides. In another embodiment the carbohydrates are pyranose and furanose sugars.

Non limiting examples of pyranose and furanose sugars include threose, ribulose, ketose, gentiobiose, aldose, aldotetrose, aldopentose, aldohexose, ketohexose, ketotetrose, ketopentose, erythrose, threose, ribose, deoxyribose, arabinose, xylose, lyxose, allose, altrose, glucose, mannose, gulose, idose, glactose, talose, erythrulose, ribulose, xylulose, psicose, fructose, sorbose, tagatose, dextrose, maltose, lactose, sucrose, cellulose, aldose, amylose, palatinose, trehalose, turanose, cellobiose, amylopectin, glucosamine, mannosamine, fucose, phamnose, glucuronate, gluconate, glucono-lactone, muramic acid, abequose, rhamnose, gluconic acid, glucuronic acid, and galactosamine.

The carbohydrate can be optionally deoxygenated at any corresponding C-position, and/or substituted with one or more moieties such as hydrogen, halo, haloalkyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, amino acid, amino acid esters, amides. phosphonyl, phosphinyl, phosphoryl, thioester, thioether, oxime, hydrazine, carbamate, phosphonic acid, phosphonate, or any other viable functional group that does not inhibit the pharmacological activity of this compound. Particular exemplary substituents include amine and halo, particularly fluorine. The substituent or carbohydrate can be either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis. The term aryl, as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

As used herein, the term "patient" refers to warm-blooded animals or mammals, and in particular humans, who are in need of the therapy described herein. The term host, as used herein, refers to a unicellular or multicellular organism, including cell lines and animals, and preferably a human.

X. A Method of Treating a Human Being or Animal with an Inflammatory Disorder Comprising Administering an Effective Amount of a Compound Identified Above.

Any of the compounds, including but not limited to compounds such as those identified in the foregoing assay systems, can be tested and used for the ability to ameliorate inflammatory and cardiovascular disease symptoms. Cell-based and animal model-based assays for the identification of compounds exhibiting such an ability to ameliorate inflammatory disease symptoms are described below.

First, cell-based systems such as those described above can be used to identify compounds that can act to ameliorate inflammatory disease symptoms. For example, such cell systems can be exposed to a compound, suspected of exhibiting an ability to ameliorate inflammatory disease symptoms, at a sufficient concentration and for a time sufficient to elicit such an amelioration of inflammatory disease symptoms in the exposed cells. After exposure, the cells are examined to determine whether one or more of the inflammatory disease cellular phenotypes has been altered to resemble a more normal or more wild type, anti-inflammatory disease phenotype. For example, and not by way of limitation, the expression of certain redox sensitive genes can be used to assess the antiinflammatory phenotype of a cell, these redox sensitive genes, such as those that are involved in the presentation of an immune response including, but are not limited to, those expressing cytokines involved in initiating the immune response (e.g., IL-1.beta.), chemoattractants that promote the migration of inflammatory cells to a point of injury (e.g., MCP-1), growth factors (e.g., IL-6 and the thrombin receptor), and adhesion molecules (e.g., VCAM-1 and E-selectin).

In addition, animal-based inflammatory disease systems, such as the murine model of Type 1 hypersensitivity, can be used to identify compounds capable of ameliorating inflammatory disease symptoms. Such animal models can be used as test substrates for the identification of drugs, pharmaceuticals, therapies and interventions that can be effective in treating inflammatory disease. For example, animal models can be exposed to a compound, suspected of exhibiting an ability to ameliorate inflammatory disease symptoms, at a sufficient concentration and for a time sufficient to elicit such an amelioration of inflammatory disease symptoms in the exposed animals. The response of the animals to the exposure can be monitored by assessing the reversal of disorders associated with inflammatory disease, for example, by counting the number of eosinophils elicited into the peritoneum before and after treatment.

Further, animal-based inflammatory disease systems, such as the murine asthma model of airway eosinophilia and hyperreactivity, can be used to identify compounds capable of ameliorating asthma symptoms. Such animal models can be used as test substrates for the identification of drugs, pharmaceuticals, therapies and interventions that can be effective in treating asthma. For example, animal models can be exposed to a compound, suspected of exhibiting an ability to ameliorate asthma symptoms, at a sufficient concentration and for a time sufficient to elicit such an amelioration of asthma symptoms in the exposed animals. The response of the animals to the exposure can be monitored by assessing the reversal of disorders associated with asthma, for example, by counting the number of eosinophils elicited into the bronchoaveolar lavage fluid before and after treatment or by testing for improvement in luncg function after treatment, for example, by accessing airway hyperreactivity to methacholine.

Additionally, animal-based inflammatory disease systems, such as the murine delayed type hypersensitivity model, a generalized model for inflammation accompanied by edema, can be used to identify compounds capable of ameliorating inflammation. Such animal models can be used as test substrates for the identification of drugs, pharmaceuticals, therapies and interventions that can be effective in treating inflammation. For example, animal models can be exposed to a compound, suspected of exhibiting an ability to ameliorate inflammation symptoms, at a sufficient concentration and for a time sufficient to elicit such an amelioration inflammation symptoms in the exposed animals. The response of the animals to the exposure can be monitored by assessing the reversal of disorders associated with inflammation accompanied by edema, for example, by measuring the amount of swelling in a limb after intradermal injection methylated BSA (metBSA) into the limb.

The CPRE can regulate cytoprotective effects by inducing the expression of cytoprotective enzymes or other factors either singularly or coordinately. Thus, the assay described herein can be used to identify compounds that activate the CPRE and cause the cytoprotective effect and/or anti-inflammatory effect. Compounds that reverse any aspect of inflammatory disease symptoms should be considered as candidates for human inflammatory disease therapeutic intervention. Moreover, any of the compounds, including but not limited to compounds such as those identified in the foregoing assay systems can be used in the diagnosis, prognosis, prevention, and/or treatment of inflammatory conditions. For example, since the compounds, including but not limited to compounds such as those identified in the foregoing assay systems can inhibit the activation, proliferation, and/or differentiation of cells involved in an inflammatory response, these molecules can be used to prevent and/or treat chronic and acute inflammatory conditions. Such inflammatory conditions include, but are not limited to, for example, inflammation associated with infection (e.g., septic shock, sepsis, or systemic inflammatory response syndrome), ischemia-reperfusion injury, endotoxin lethality, complement-mediated hyperacute rejection, nephritis, cytokine or chemokine induced lung injury, inflammatory bowel disease, Crohn's disease, over production of cytokines (e.g., TNF or IL-1.), respiratory disorders (e.g., asthma and allergy); gastrointestinal disorders (e.g., inflammatory bowel disease); cancers (e.g., gastric, ovarian, lung, bladder, liver, and breast); CNS disorders (e.g., multiple sclerosis; ischemic brain injury and/or stroke, traumatic brain injury, neurodegenerative disorders (e.g., Parkinson's disease and Alzheizmer's disease); AIDS-related dementia; and prion disease); cardiovascular disorders (e.g., atherosclerosis, myocarditis, cardiovascular disease, and cardiopulmonary bypass complications); as well as many additional diseases, conditions, and disorders that are characterized by inflammation (e.g., hepatitis, rheumatoid arthritis, gout, trauma, pancreatitis, sarcoidosis, dermatitis, renal ischemia-reperfusion injury, Grave's disease, systemic lupus erythematosus, diabetes mellitus, and allogenic transplant rejection).

Because inflammation is a fundamental defense mechanism, inflammatory disorders can effect virtually any tissue of the body. Accordingly, compounds, including but not limited to compounds such as those identified in the foregoing assay systems, have uses in the treatment of tissue-specific inflammatory disorders, including, but not limited to, adrenalitis, alveolitis, angiocholecystitis, appendicitis, balanitis, blepharitis, bronchitis, bursitis, carditis, cellulitis, cervicitis, cholecystitis, chorditis, cochiflis, colitis, conjunctivitis, cystitis, dermatitis, diverticulitis, encephalitis, endocarditis, esophagitis, eustachitis, fibrositis, folliculitis, gastritis, gastroenteritis, gingivitis, glossitis, hepatosplenitis, keratitis, labyrinthitis, laryngitis, lymphangitis, mastitis, media otitis, meningitis, metritis, mucitis, myocarditis, myosititis, myringitis, nephritis, neuritis, orchitis, osteochondritis, otitis, pericarditis, peritendonitis, peritonitis, pharyngitis, phlebitis, poliomyelitis, prostatititis, Pulpitis, retinitis, rhinitis, salpingitis, scleritis, sclerochoroiditis, scrotitis, sinusitis, spondylitis, steatitis, stomatitis, synovitis, syringitis, tendonitis, tonsillitis, urethritis, and vaginitis.

The CPRE can regulate cytoprotective effects by inducing the expression of cytoprotective enzymes or other factors either singularly or coordinately. Thus, the assay described herein can be used to identify compounds that activate the CPRE and cause the cytoprotective effect and/or reverse the effects of oxidative stress. Compounds that reverse any aspect of oxidative stress or induce a cytoprotective phenotype should be considered as candidates for human proliferative disease therapeutic intervention. These compounds may inhibit the proliferation of the disorder through direct or indirect interactions.

Examples of hyperproliferative disorders that can be treated include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvis, skin, soft tissue, spleen, thorax, and urogenital tract; Acute Childhood Lymphoblastic Leukemia; Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphorria, Adult Lymphocytic Leukemia, Adult Non-Hodgkin's Lymphoma, Adult Primary Liver Cancer, Adult Soft Tissue Sarcoma, AIDS-Related Lymphorria, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphorria, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalanic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma. Endometrial Cancer, Ependymoma, Epithelial Cancer, Esophageal Cancer, Ewing's Sarcoma and Related Tumors, Exocrine Pancreatic Cancer, Extraeranial Germ Cell Tumor, Extragonadal Germ Cell Tumor, Extrahepatie Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lympho proliferative Disorders, Macroglobulinemia, Male Breast Cancer, Malignant Mesothelioma, Malignant Thymoma, Medulloblastomia, Melanoma, Mesothelioma, Metastatie Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyrigeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo/Malignant Fibrous Sarcoma,Osteosarcoma/ Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid, Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethial Cancer, Uterine Cancer, Uterine Sarcoma, Vaginal Cancer, Visual Pathway and Hypothalarruc Glioma, Vulvar Cancer, Waldenstroin's Macroglobulinemia, Wilm's Tumor, and any other hyperproliferative disease, besides neoplasia, located in an organ system listed above, or included in Table 3 below.

TABLE 3

Types of Proliferative Disorders associated with Particular Organ Systems

| Organ System | Disease/Pathology |
| --- | --- |
| Dermatological | Psoriasis (all forms), acne vulgaris, acne rosacea, common warts, anogenital (venereal) warts, eczema; lupus associated skin lesions; dermatitides such as seborrheic dermatitis and solar dermatitis; keratoses such as seborrheic keratosis, senile keratosis, actinic keratosis, photo-induced keratosis, skin ageing, including photo-induced skin aging, keratosis follicularis, keloids |

TABLE 3-continued

Types of Proliferative Disorders associated with Particular Organ Systems

| Organ System | Disease/Pathology |
| --- | --- |
| | and Prophylaxis against keloid formation; leukoplakia, lichen, planus, keratitis, contact dermatitis, eczema, urticaria, pruritus, hidradenitis, acne inverse |
| Cardiovascular | Hypertension, vasculo-occlusive diseases including Atherosclerosis, thrombosis and restenosis after angioplasty; acute coronary syndromes such as unstable angina, myocardial infarction, ischemic and non-ischemic cardiomyopathies, post-MI cardiomyopathy and myocardial fibrosis, substance-induced cardiomyopathy. |
| Endocrine | Insulin resistant states including obesity, diabetes mellitus (types 1 & 2), diabetic retinopathy, macular degeneration associated with diabetes, gestational diabetes, impaired glucose tolerance, polycystic ovarian syndrome; osteoporosis, osteopenia, accelerated aging of tissues and organs including Werner's syndrome. |
| Urogenital | Endometriosis, benign prostatic hyperplasia, leiomyoma, Polycystic kidney disease, diabetic nephropathy. |
| Pulmonary | Asthma, chronic obstructive pulmonary disease (COPD), reactive Airway disease, pulmonary fibrosis, pulmonary hypertension. |
| Connective tissue/joints | Immunological Rheumatoid arthritis, Raynaud's phenomenon/disease, Sjogren's Syndrome, systemic sclerosis, systemic lupus erythematosus, vasculitides, ankylosing spondylitis, osteoarthritis, reactive arthritis, psoriatic arthritis, fibromyalgia. |
| Other | Fibrocystic breast disease, fibroadenoma, chronic fatigue syndrome. |

Further nonlimiting examples of neoplastic diseases or malignancies treatable are listed in Table 4.

TABLE 4

Malignancy/Cancer Type listed by Organ System

| Organ System | Malignancy/Cancer type |
| --- | --- |
| Skin | Basal cell carcinoma, melanoma, squamous cell carcinoma; cutaneous T cell lymphoma; Kaposi's sarcoma. |
| Hematological | Acute leukemia, chronic leukemia and myelodysplastic syndromes. |
| Urogenital | Prostatic, renal and bladder carcinomas, anogenital carcinomas including cervical, ovarian, uterine, vulvar, vaginal, and those associated with human papilloma virus infection. |
| Neurological | Gliomas including glioblastomas, astrocytoma, ependymoma, medulloblastoma, oligodendroma; meningioma, pituitary adenoma, neuroblastoma, craniopharyngioma. |
| Gastrointestinal | Colon, colorectal, gastric, esophageal, mucocutaneous carcinomas. |
| Breast | Breast cancer including estrogen receptor and progesterone Receptor positive or negative subtypes, soft tissue tumors. |
| Metastasis | Metastases resulting from the neoplasms. |
| Skeletal | Osteogenic sarcoma, malignant fibrou histeocytoma, chondrosarcoma, rhabdomyosarcoma, leiomyosarcoma, myeloma. |
| Diffuse Tumors | Lymphoma (non-Hodgkin's or Hodgkin's), sickle cell anemia. |
| Other | Angiomata, angiogenesis associated with the neoplasms. |

The CPRE can regulate cytoprotective effects by inducing the expression of cytoprotective enzymes or other factors either singularly or coordinately. Thus, the assay described herein can be used to identify compounds that activate the CPRE and cause the cytoprotective effect. Cytoprotective agents can be administered to protect normal tissues and organs from the damaging effects of chemotherapeutic drugs, radiation therapy and disease processes. For example, cytoprotectants can minimize the dose-limiting adverse effects of chemotherapy without diminishing the anticancer effect of treatment. Examples of cytoprotective drugs include Epogen (Amgen), hematopoetic growth factors, amifostine (Medimmune Oncology), dexrazoxane (Zinecard, Pharmacia), albumin granulocyte colony stimulating factor (Albugranin™, Human Genome Sciences), leucovorin, and methotrexate. In one nonlimiting example, cytoprotectants can rescue hamatopoeitic stem cells from the deleterious effects of radiation or chemotherapy. Cytoprotective agents of the present invention may be used alone or in combination with other drugs that act as cytoprotectants.

Additionally, gene expression patterns can be utilized to assess the ability of a compound to ameliorate inflammatory disease symptoms. For example, the expression pattern of one or more fingerprint genes can form part of a "fingerprint profile" which can be then be used in such an assessment. "Fingerprint profile", as used herein, refers to the pattern of mRNA expression obtained for a given tissue or cell type under a given set of conditions. Such conditions can include, but are not limited to different shear stress conditions. Fingerprint profiles can be generated, for example, by utilizing a differential display procedure, as discussed above, Northern analysis and/or RT-PCR. Fingerprint profiles can be characterized for known states, either inflammatory disease or normal, within the cell- and/or animal-based model systems. Subsequently, these known fingerprint profiles can be compared to ascertain the effect a test compound has to modify such fingerprint profiles, and to cause the profile to more closely resemble that of a more desirable fingerprint.

For example, administration of a compound can cause the fingerprint profile of an inflammatory disease model system to more closely resemble the control system. Administration of a compound can, alternatively, cause the fingerprint profile of a control system to begin to mimic an inflammatory disease state. Such a compound can, for example, be used in further characterizing the compound of interest, or can be used in the generation of additional animal models.

The identified compounds that induce CPRE expression or modulate upstream signaling pathways of the CPRE cascade can be administered to a patient or animal at therapeutically effective doses to treat or ameliorate inflammatory disease. A therapeutically effective dose refers to that amount of the compound sufficient to result in amelioration of symptoms of inflammatory disease.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Pharmaceutical compositions for use in accordance with the present invention can be formulated in conventional manner using one or more physiologically acceptable carriers or excipients.

Thus, the compounds and their physiologically acceptable salts and solvates can be formulated for administration by inhalation or insufflation (either through the mouth or the nose) or oral, buccal, parenteral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

The present invention is described in further detail in the following examples. These examples are intended to be illustrative only, and are not intended to limit the scope of the invention.

EXAMPLES

The preceding protocols and experimental details are referenced in the examples that follow.

Through the following experiments the CPRE has been identified as important transcriptional control elements in the regulation of cytoprotective genes in endothelial cells. Through a bioinformatic analysis of the promoter regions of these endothelial, shear stress-regulated genes, a common control element has bee identified that is called the CPRE. Furthermore, it has been demonstrated that this control element is highly responsive to shear stress and demonstrate a method for screening for pharmacological agents with anti-inflammatory properties that increase expression through the CPRE.

Example 1

Expression of ARE-containing Genes is Elevated in LSS-exposed EC, Compared to OSS or Static Control Cultures.

Figure 1:
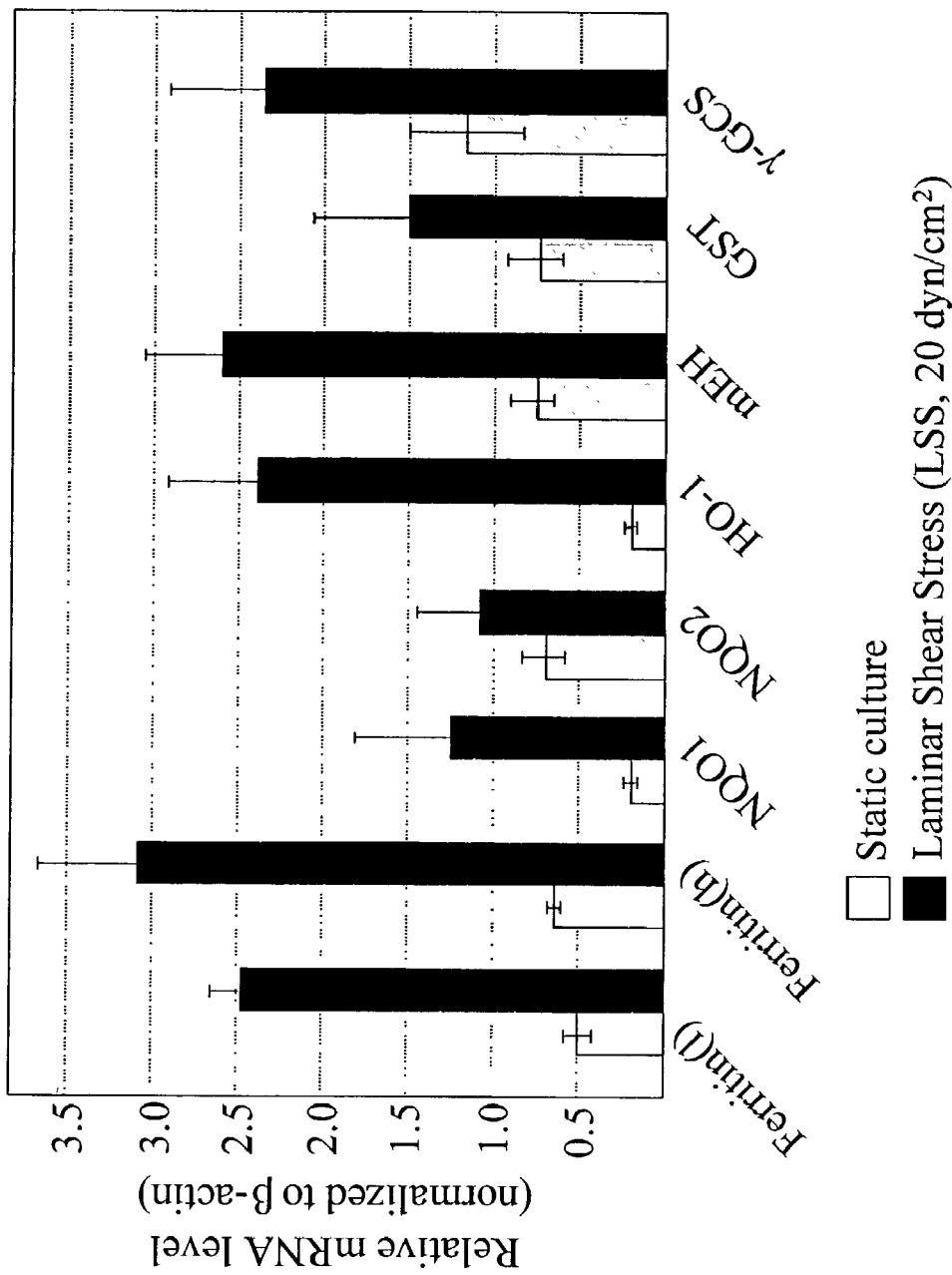
FIG. 1 is a bar graph showing the effect on the relative mRNA levels (normalized to β-actin) of the CPRE-regulated genes, ferritin (l), ferritin(h), NQO1, NQO2, HO-1, mEH, GST, γ-GCS in static culture (stippled bars) and during 20 dyn/cm2 of laminar shear stress (LSS) (solid bars). LSS elevated the mRNA levels of the eight CPRE-regulated genes tested.

DNA sequencing of subtracted libraries and DNA microarray analysis identified several genes that were upregulated by LSS (vs. static or OSS). Several of these genes were previously reported to be regulated by oxidative stress. Furthermore, some of these genes were reported to be regulated by the antioxidant response element (ARE). To confirm that LSS induces the expression of these genes, mRNA levels were assayed by semi-quantitative RT-PCR. As can be seen from FIG. 1, all of the genes were induced (although to various degrees) by LSS. These include ferritin (heavy and light chains), quinone oxidoreductase-1 & 2 (NQO1 & NQO2), heme oxygenase-1 (HO-1), microsomal epoxide hydrolase (mEH), glutathione-S-transferase (GST), and gamma glutamyl cysteine synthase (γ-GCS). These observations confirm that exposure of EC to LSS for 48 hrs increases expression of these genes compared to static controls.

Figure 2:
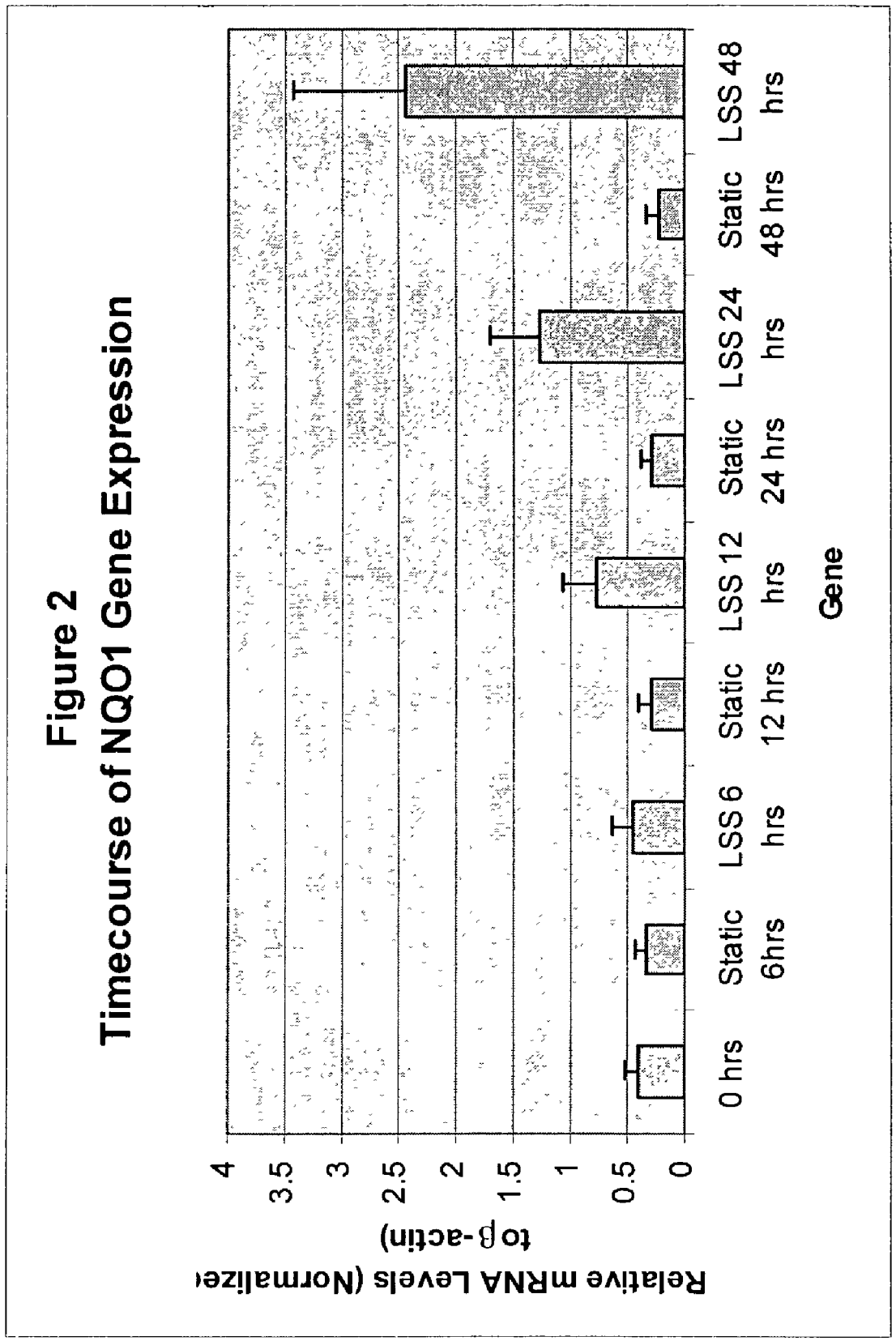
FIG. 2 is a bar graph showing the time course of NQO1 gene expression under static and laminar shear stress (LSS) conditions. NQO1 mRNA levels (normalized to β-actin) were measured following 6, 12, 24, and 48 hours of LSS. NQO1 mRNA levels were elevated 12, 24 and 48 hours after the initiation of LSS.
Figure 3:
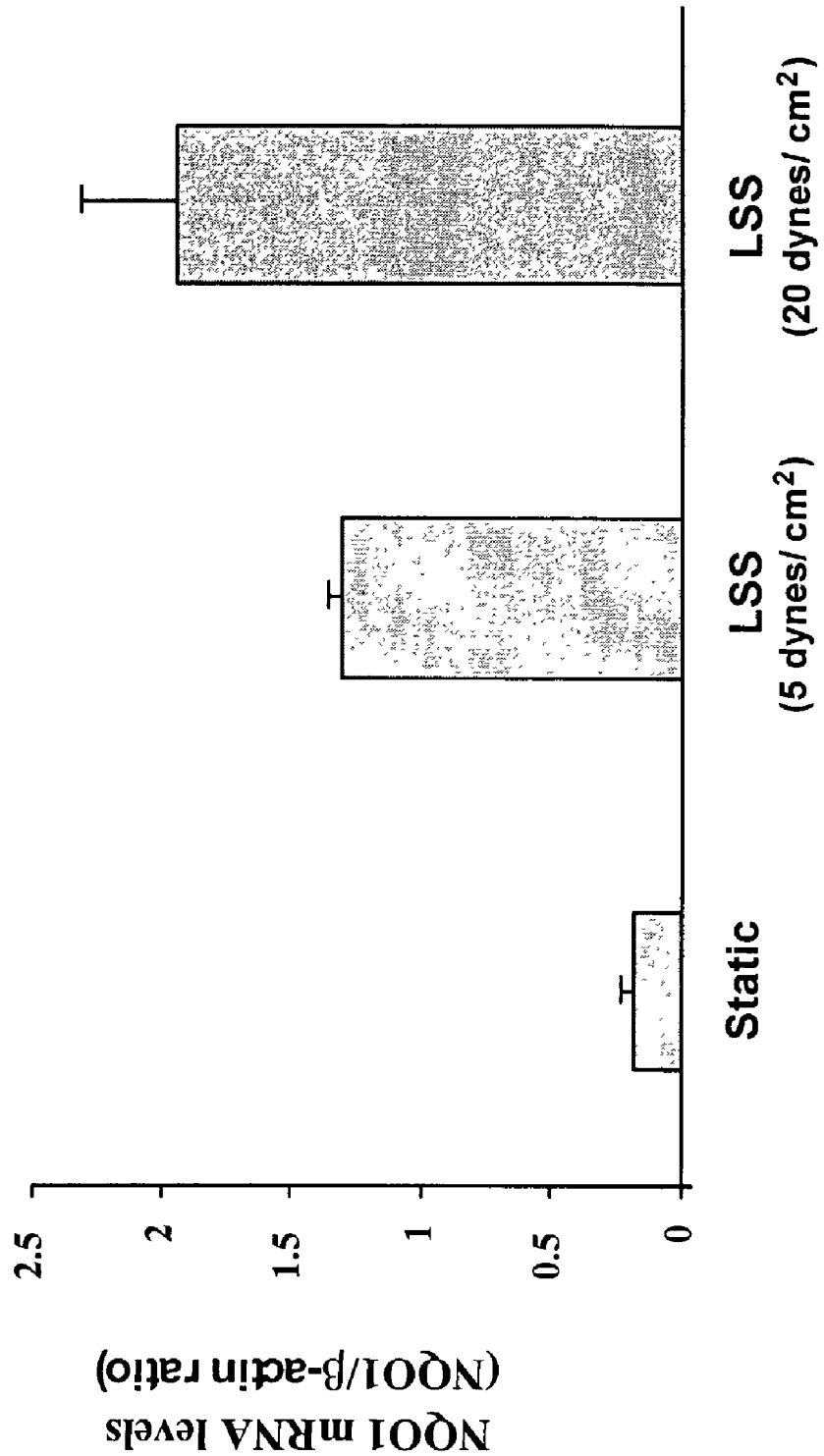
FIG. 3 is a bar graph comparing the effects of laminar shear stress (LSS) at 5 and 20 dynes/cm2 on NQO1 mRNA levels (normalized to β-actin) in cultured endothelial cells. NQO1 mRNA levels where significantly elevated at 5 and 20 dynes/cm2 of LSS compared to static conditions.
Figure 4:
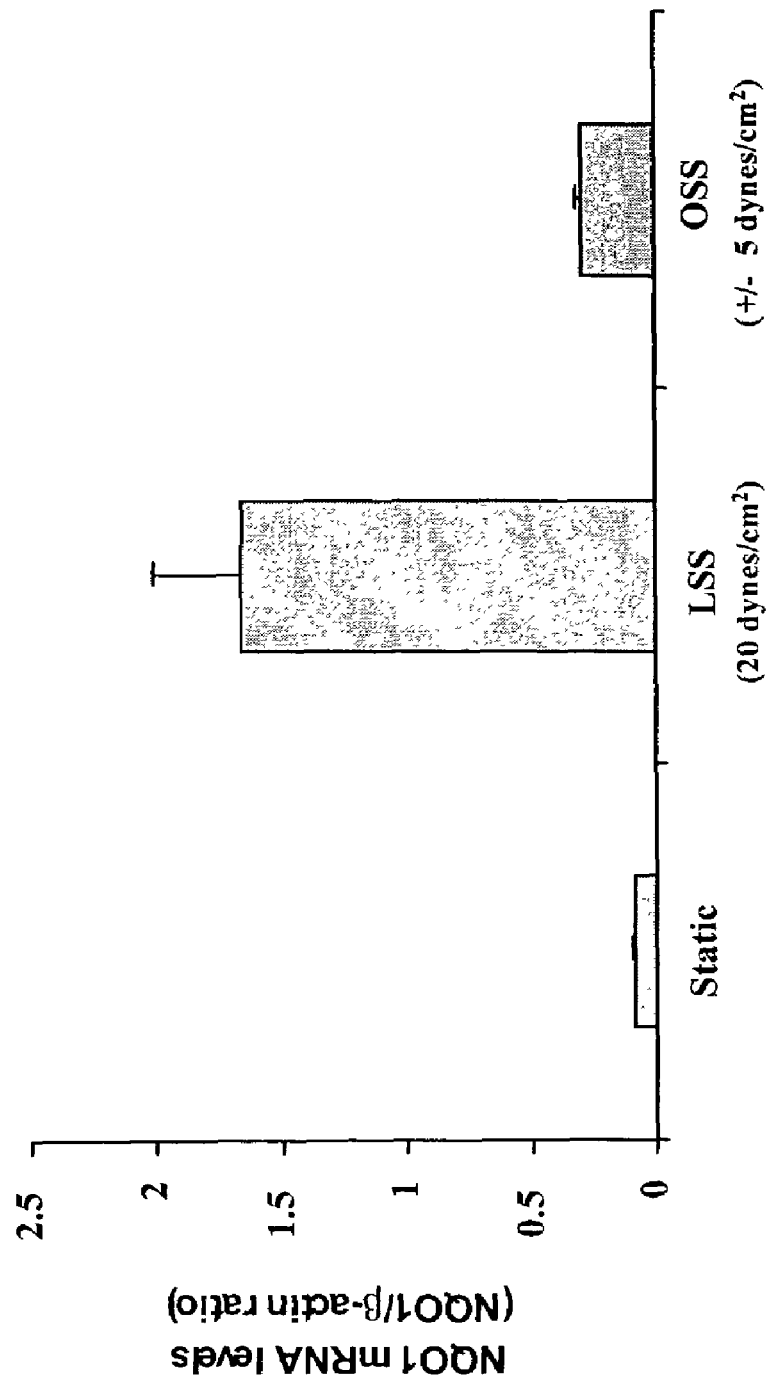
FIG. 4 is a bar graph comparing the effect of laminar shear stress (LSS) (20 dynes/cm2) with oscillatory shear stress (OSS) (+/−5 dynes/cm2) on NQO1 mRNA levels (normalized to β-actin) in cultured endothelial cells. NQO1 mRNA levels were significantly elevated in both LSS and OSS conditions, but to a larger extent by LSS than OSS conditions.

The effect of time, flow rate, and type of shear stress were also evaluated for their contribution to modulating NQO1 gene expression. As can be seen in FIG. 2, the inducible expression of NQO1 in response to LSS increased progressively from 6 to 48 hrs. In contrast, the relative expression of NQO1 in static cultures remained relatively constant throughout the time course. In addition, the effect of varying levels of LSS on NQO1 gene expression was investigated. As shown in FIG. 3, there appears to be a force-dependent effect on the expression of NQO1. As compared to static cultures, 5 dyn/cm2 of LSS increased the expression of NQO1 approximately 5-fold by 48 hrs. Increasing the flow rate to 20 dyn/cm2 resulted in even greater levels of expression of NQO1 at 48 hrs. The effects of oscillatory shear stress (OSS) and LSS on NQO1 gene expression at 48 hrs were compared next. As can be seen in FIG. 4, although exposure of endothelial cells for 48 hr. to OSS (+/− 5 dyn/cm2) induced the level of NQO1 gene expression compared to static cultures, the increase was not as great as exposure to LSS. In considering the observations from FIG. 3 and FIG. 4, these results suggest that the type of shear stress (OSS vs. LSS) differentially determines the level of gene expression of NQO1. OSS at +/− 5 dyn/cm2 demonstrated only a 2-3 fold increased expression of NQO1 over static controls, whereas LSS at 5 dyn/cm2 demonstrated an approximately 7-fold increased expression. Therefore, not only the type of shear stress (OSS vs. LSS), but also the relative levels of shear stress (5 vs. 20 dyn/cm2) modulate NQO1 gene expression at 48 hrs in endothelial cells.

Cell Culture and Shear Stress Experiments:

Primary human aortic endothelial cells (HAEC) were obtained from Clonetics, Inc. and maintained at 37° C. in 5% $CO_2$ incubator in EGM-2 as recommended by the supplier. Cells were used between passage 5 and passage 9. HAECs were seeded onto gelatin-coated glass slides and grown overnight prior to exposure to shear stress. Shear stress experiments were carried out in a parallel plate flow chamber as described previously (Chappell et al., (1998) Circ. Res. 82 (5): 532-539). Cells were exposed to either static conditions (cells maintained on glass slides in a 150 $cm^2$ tissue culture dish, or exposed to shear stress. For each treatment at least two separate plates were pooled for RNA collection.

Gene Expression Analysis:

Oligonucleotide primer pairs were designed to amplify an approximately 500 base pair fragment from the 3' end of each mRNA. Total RNA was collected from HAECs exposed to either static conditions or varying shear stress conditions. RNA was collected by lysing cells directly in Trizol (Life Technologies, Inc.) RNA was collected by isopropanol precipitation, suspended in nuclease-free water and maintained at −80° C. 3 µg of total RNA was reverse transcribed into cDNA by reverse transcriptase (Life Technologies) and the levels of each gene product was measured by semi-quantitative end-point RT-PCR analysis. PCR conditions were performed in a 30 µL reaction volume. Each reaction contained 1 µL of diluted cDNA, dNTP mixture (0.2 mM final concentration, 1×PCR buffer, 1 unit TAQ polymerase (Sigma, RedTaq,~3.0 ng). Cycling conditions were as follows:95° C. initial denaturation for 5 min, 26 cycles of 94° C. denaturation (20 sec), 55° C. annealing (30 sec) and 72° C. extension (20 sec) followed by a 7 min extension at 72° C. After amplification, 15 iL of the sample was electrophoresed on a 1.5% agarose gel and stained by ethidium bromide. Relative band intensities were determined by densitometry using the BioRad Quantity ONE software. For each primer pair, serial dilutions of each cDNA were assayed and a dilution that resulted in linear amplification under the PCR conditions used was used for further experiments. Each sample was assayed at least three times from the same RNA sample and results are expressed as relative levels compared to βactin. DNA sequences for the primer pairs used are set out in Table 5

TABLE 5

| Gene Name | Genebank Accession Number | Primer Sequence | |
|---|---|---|---|
| Gamma glutamyl cysteine synthase (heavy subunit) | M90656 | 5'-TGAGGCCAACATGCGAAAAC<br>3'-AAATCACTCCCCAGCGACAATC | (SEQ ID NO 26)<br>(SEQ ID NO 27) |
| Quinone Oxidoreductase 2 (NQO2) | J02888 | 5'-ACTGAGCAGGCAGGGCT<br>3'-ATCTGAGGGGCAAGGACTT | (SEQ ID NO 28)<br>(SEQ ID NO 29) |
| Glutathione S-transferase | XM_012235 | 5'-GTTTTTGCCAATCCAGAAGAC<br>3'-GCTCCCCTCCTACCTAAAATC | (SEQ ID NO 30)<br>(SEQ ID NO 31) |
| Quinone Oxidoreductase 1 (NQO1) | J03934 | 5'-CCTGGCCCTTGCAATCTTCTAC<br>3'-CAGCTCGGTCCAATCCCTTCA | (SEQ ID NO 32)<br>(SEQ ID NO 33) |

TABLE 5-continued

| Gene Name | Genebank Accession Number | Primer Sequence | |
|---|---|---|---|
| Ferritin (heavy chain) | NM_002032 | 5'-CTGGCCACTGACAAAAATGACC | (SEQ ID NO 34) |
| | | 3'-AACGGCATTAAGGAATCTGGA | (SEQ ID NO 35) |
| Heme Oxygenase-1 | XM_009946 | 5'-TTGCTGTAGGGCTTTATGC | (SEQ ID NO 36) |
| | | 3'-CTGCATTTGAGGCTGAGCC | (SEQ ID NO 37) |
| Ferritin (light chain) | M10119 | 5'-GCGCGAGGGCTACGAG | (SEQ ID NO 38) |
| | | 3'-CTATTGGCTGGAGGGAGAGG | (SEQ ID NO 39) |
| Beta-Actin | XM_004814 | 5'-ATCGGCGGCTCCATCC | (SEQ ID NO 40) |
| | | 3'-GGGGCACGAAGGCTCATC | (SEQ ID NO 41) |

Example 2

Shear Stress Activation of the NQO1 Gene is Mediated Via the ARE

To determine if the effect of LSS on NQO1 gene expression is mediated through transcriptional activation, transient transfection assays were used with a region of the NQO1 promoter. This promoter construct contains the previously characterized ARE region cloned upstream of the chloramphenicol acetyltransferase gene (CAT). The data shown in FIG. 5 demonstrates that exposure of endothelial cells for 48 hours to LSS results in substantial activation of the NQO1 promoter. When a plasmid containing a deletion of the ARE element from NQO1 was used, no activation was observed by LSS. These observations directly demonstrate that LSS activation of the NQO1 gene in endothelial cells occurs at the transcriptional level. More importantly, activation by LSS requires a functional ARE element.

Human microvascular endothelial cells (HMEC) were grown to 60% confluence on glass plates. The cells were transiently transfected with 5 µg of a pNQO1CAT1.55 or pNQO1CAT1.55ΔARE using Superfect transfection reagent according to manufacturer's instructions (Qiagen, Inc.). pNQO1CAT1.55 contains coordinates −1550 to +110 of the human NQO1 gene promoter (Li & Jaiswal (1992) J. Biol. Chem. 267: 15097-15104) cloned upstream of the CAT reporter gene. pNQO1CAT1.55ΔARE has a deletion between −471 and −447 within the ARE. Four hours following transfection, the cells were exposed to either LSS (20 dyn/cm2) or static conditions for 48 hrs. Cells were harvested, protein extracts were prepared and total protein was quantitated (BioRad). CAT activity was determined (Gorman et al. (1982) Cell 62: 841-843) and normalized to protein levels.

Example 3

Determination of Consensus CPRE Sequence from Alignment of ARE Sequences from the 5' Regulatory Regions of LSS-activated Genes.

The observation that the ARE from the NQO1 gene mediates transcriptional activity in response to LSS suggests that the ARE transcriptional element is an important mediator of signals generated in endothelial cells by hemodynamic forces. In addition, since several ARE-containing genes are regulated by LSS (FIG. 1) the sequence similarity of the ARE in the 5' regions of these genes was examined (FIG. 6).

Alignment of the 5' regulatory region from genes that were demonstrated to be inducible by LSS generated a 13 nt sequence core with the sequence 5'-RTGACWNAGCANW-3' (SEQ ID NO 1). The genes that contain this consensus sequence all have in common the ability to regulate and maintain redox balance within the cell and are responsive to oxidative signals. Based on alignments of these shear stress regulated genes, the consensus sequence was extended beyond what others have termed the ARE. Therefore, this new consensus sequence, that is common among a subset of endothelial cell LSS-activated genes, has been termed the cytoprotective response element, or CPRE. Like the ARE the CPRE has two well-conserved cores motifs: TGAC separated by three variant nucleotides and a well-conserved GCA motif.

Example 4

Diagram of the CPRE-luciferase Expression Vector

Coordinate induction of CPRE-containing genes in the vasculature will be beneficial. Increased expression of these genes will protect the cell from oxidant-mediated damage to DNA and or macromolecules. Furthermore, since oxidative stress and redox-mediated gene expression is known to be important in the pathogenesis of inflammatory disease, reduction of the intracellular oxidative state by coordinately increasing the amount of enzymes and proteins that function to reduce oxidant stress and oxidant signals can potentially be therapeutically beneficial for the treatment of inflammatory disease. Therefore, a reporter construct has been designed composed of three tandem copies of the CPRE operably linked to a minimal promoter (SV40) and fused to a heterologous reporter gene (luciferase) (FIG. 7).

Construction of the CPRE-luc Reporter Vector p3xCPRE-Luc

Three tandem copies of the CPRE consensus sequence were synthesized as single stranded, complimentary oligonucleotides.

Sense strand: GAGCTCCAGTCACAGTGACTCAGCAGAATCCAGTCACAGTGACTCAGCAGAATTCC AGTCACAGTGACTCAGCAGAATCAGATCT (SEQ ID NO 42). The oligonucleotides were annealed by heating to 94° C. and cooling down to room temperature. The annealed oligonucleotides were ligated into the SacI and BglII sites of pGL3-Promoter (Promega). Recombinant inserts were selected and screened for the presence of the CPRE element by restriction enzyme analysis. Plasmid DNA was purified (Qiagen, Inc) for analysis by transient transfection analysis.

Example 5

CPRE-luc is Inducible by LSS in EC

To demonstrate that the 3XCPRE/Luc reporter construct is functional, human microvascular endothelial cells (HMECs) were transiently transfected and cell extracts were assayed for luciferase activity. FIG. 8 shows that, as expected, LSS treatment of HMECs results in a dramatic increase in the activity of this reporter construct. This observation suggests that the same or similar signals that activate endogenous CPRE-containing genes also activate the 3X CPRE/Luc reporter construct.

HMEC cells were seeded onto glass plates and were transiently transfected with 5 micrograms of p3xCPRE/Luc and 0.5 micrograms of pRL-SV40 (renilla luciferase constitutively expressed under the control of the SV40 promoter). pRL-SV40 was used to normalize for transfection efficiency. 24 hours following transfection, cells were either maintained as static cultures or were exposed to LSS (20 dyn/cm2) for 48 hrs. Cells were scraped into lysis buffer supplied by the manufacturer (Promega) and luciferase activity was measured by using dual luciferase reporter assay system according to the manufacturer's instructions (Promega, Inc.). All data were normalized to the renilla activity and reported as relative firefly/renilla luciferase activity.

Example 6

Regulation of CPRE by Nrf-2 and Keap-1

The transcription factor NF-E2-related factor 2 (Nrf-2) has been shown to bind to and activate transcription from the ARE (Nguyen et al. (2000) J. Biol. Chem. 275(20):15466-15473.; Venugopal R and Jaiswal A (1996) Proc. Natl. Acad. Sci. 2:8965-8969). To demonstrate that Nrf-2 can similarly activate transcription from the CPRE in endothelial cells, CPRE-luc was cotransfected with an expression vector encoding Nrf-2 into both HMEC and HeLa cells (FIG. 9). As shown in FIG. 9a, coexpression of Nrf2 in HeLa cells activates transcription from the reporter construct p3xCPRE/Luc. Similarly, expression of Nrf-2 activates p3xCPRE/Luc reporter activity in HMEC cells (FIG. 9b). Furthermore, a mutation in the CPRE element (p3xmutCPRE/Luc) demonstrated no induced activity when Nrf-2 was expressed.

A recent study suggest that Nrf-2 activity is normally repressed through its localization in the cytoplasm by binding to the cytoskeleton-associated protein Keap-1(Itoh K, et al. (1999) Genes Dev 13(1):76-86). Immunocytochemical analysis involving cotransfection of Keap-1 and Nrf-2 showed that electrophilic agents released Nrf-2 from Keap1, allowing the translocation of Nrf-2 from the cytoplasm to the nucleus to activate transcription. It has been suggested that the Nrf-2-Keap1 interaction can constitute a cytoplasmic sensor for oxidative stress. The role of Keap-1 on inducible activation of the CPRE in endothelial cells and HeLa cells was also examined. As shown in FIG. 9c, overexpression of Keap-1 in HeLa cells inhibited the induction of CPRE transcriptional activity mediated by Compound A. These results demonstrate that the transcription factor Nrf-2 and the repressor protein Keap-1 regulate transcription from the CPRE element in endothelial cells and suggest that the molecular mechanisms that activate CPRE gene expression in endothelial cells and epithelial cells are similar. Additionally, these results show for the first time that Nrf-2 can regulate expression from an ARE-like element in endothelial cells.

HMEC cells (passage 20) and HeLa cells were seeded into 6 well plates and were grown to approximately 60-70% confluency. Cells were transfected with 2 µg (HeLa) or 1 µg (HMEC) each of p3xCPRE/Luc reporter and Nrf-2 expression vector (an expression vector containing the full-length murine Nrf-2 gene under the control of the CMV promoter (Asakura & Karino (1990) Circ Res, 66:1045-1066). Cells were cultured for an additional 48 hours, and luciferase activity was determined (Promega). An average of at least three independent determinations were made for each experimental sample. Results are expressed as ratio of firefly/*renilla* luciferase.

Example 7

Overexpression of the CPRE-regulated Gene NQO1 Suppresses VCAM-1 Gene Expression Expression of several inflammatory gene products including VCAM-1 and MCP-1 in endothelial cells is redox sensitive (Kunsch & Medford (1999) Circ. Res. 85:753-766). The CPRE-regulated gene NQO1 has been shown to generate antioxidant forms of ubiquinone and vitamin E after free radical attack (Beyer, et al. (1996) Natl. Acad. Sci. 93:2528-2532; and Siegel, et al. (1997) *Mol Pharmacol.* 52:300-305), providing strong evidence that this enzyme forms a part of the body's natural antioxidant defense system. To determine if overexpression of NQO1 in endothelial cells will affect redox-mediated inflammatory gene expression, the VCAM-1 promoter in the presence and absence of NQO1 was assayed. As seen in FIG. 10, treatment of endothelial cells that have been transiently transfected with a VCAM-1 reporter construct (p85VCAM/CAT) with TNF-α results in an increase in VCAM-1 promoter activity. Overexpression of NQO1 reduces the TNF-α induced promoter activity by more than 50%. This observation suggests that NQO1 can modulate cytokine-induced VCAM-1 gene expression in endothelial cells. These results suggest that therapeutic agents that increase the expression of NQO1 (and possibly other CPRE-regulated genes) can inhibit inflammatory gene expression.

HMEC cells grown in 6-well plates were transiently transfected with 0.7 µg of p85VCAM/CAT (containing coordinates −85 to +12 of the VCAM-1 promoter linked to a CAT reporter gene) plus either 1.4 µg of pcDNA-LacZ or 1.4 µg of pcDNA-NQO1 (an expression vector containing full length human NQO1 gene under the control of the CMV promoter). One day after transfection, cells were treated with TNF-α (100 U/ml) for 16 hours and lysates were collected for CAT analysis. The data shown is an average of 3 experiments.

Example 8

Nrf-2 Modulates Cytokine-Mediated VCAM-1 Gene Expression

Since NQO1 modulates cytokine-activated VCAM-1 gene expression in endothelial cells (FIG. 10) and Nrf-2 activates gene transcription via the CPRE (FIG. 9), it was examined if overexpression of Nrf-2, will also modulate cytokine-inducible VCAM-1 gene expression in endothelial cells. As seen in FIG. 11, overexpression of Nrf-2 in HMEC cells inhibited the cytokine activation of the VCAM-1 promoter. Although the levels of Nrf-2-activated genes were not evaluated in this experiment, presumably the observed inhibition of VCAM-1 is mediated, at least in part, via activation of genes such as NQO1 and likely other CPRE-regulated genes. These observations provide further support that activation of CPRE-mediated gene expression modulate redox-sensitive processes such as inflammatory gene expression. In addition, these results suggest that Nrf-2 can be a molecular regulator that mediates changes in redox state to CPRE-regulated genes in endothelial cells.

HMEC cells were transiently transfected with 0.7 μg of p85VCAM-CAT plus various expression vectors (1.4 μg of pcDNA-LacZ, LNCX-Nrf-2 or pcDNA-Keap-1). One day after transfection, cells were treated with TNF-α (100 U/ml) for 16 hours.

Example 9

Activation of p3xCPRE/Luc by Small Molecular Weight Organic Compounds

In an effort to determine the utility of the CPRE-Luc reporter construct for the identification of small molecular weight compounds that activate the CPRE, the p3xCPRE/Luc reporter was transiently transfected into both HeLa and endothelial cells (HMECs). As shown in FIG. 12a, t-BHQ, a known inducer of phase II genes and the ARE (Xie, et al. (1995) J. Biol. Chem. 270:6894), induced CPRE-dependent gene expression in endothelial cells when used at 20 μM. In addition, Compound A, when tested at 10 micromolar, also induced the transcription from the CPRE greater than two-fold in the same cell type. Similar results were obtained in HeLa cells with both t-BHQ and compound A (FIG. 12b). Transient transfection in HeLa cells demonstrated a dose-dependent response for induction of CPRE promoter activity by compound A (FIG. 13).

Although transient transfection methods are useful for understanding molecular mechanisms of gene expression and cellular biology, they are not suitable for high-throughput screening of libraries of compounds. Therefore, a stable HeLa cell line was generated that contains a stably-integrated copy of the CPRE-Luc gene. As shown in FIG. 14, compound A also activates the CPRE promoter in a dose-dependent manner with maximum activation observed at approximately 20 μM.

HMECs and HeLa cells were transiently transfected with 1 μg of 3xCPRE-Luc and 0.1 μg of pRL-SV40. One day after transfection, cells were treated with t-BHQ or compound A. Luciferase activities were determined 16 hours after exposure to tBHQ. To generate stable HeLa cell lines that contain a stably-integrated copy of the CPRE-Luc gene, HeLa cells were transfected with p3xCPRE-Luc plus pcDNA-LacZ-Hyg (an expression vector containing the hygromycin drug resistance gene) using SuperFect transfection reagent. Two days after transfection, cells were cultured in hygromycin (400 μg/ml)-containing selection medium until individual colonies were identified. The colonies were expanded and the presence of CPRE-Luc-containing clones was examined by inducible luciferase activity. All experiments are an average of at least three independent determinations for each experimental sample.

Example 10

Activation of p3xCPRE/Luc by Small Molecular Weight Organic Compounds

In the in vitro assay system described above, a stable HeLa cell line was generated that contains a stably-integrated copy of the CPRE-Luc gene.

HMECs and HeLa cells were transiently transfected with 1 μg of 3xCPRE-Luc and 0.1 μg of pRL-SV40. One day after transfection, cells were treated with the compounds listed in Table 6 Luciferase activities were determined 16 hours after exposure to the compounds. To generate stable HeLa cell lines that contain a stably-integrated copy of the CPRE-Luc gene, HeLa cells were transfected with p3xCPRE-Luc plus pcDNA-LacZ-Hyg (an expression vector containing the hygromycin drug resistance gene) using SuperFect transfection reagent. Two days after transfection, cells were cultured in hygromycin (400 μg/ml)-containing selection medium until individual colonies were identified. The colonies were expanded and the presence of CPRE-Luc-containing clones was examined by inducible luciferase activity. All experiments are an average of at least three independent determinations for each experimental sample. several small molecular weight compounds were found to achieve a two-fold induction of CPRE activity over control. Table 6 below provides illustrative activities of these compounds in inducing CPRE expression.

TABLE 6

Activation of p3xCPRE/Luc by small molecular weight organic compounds

| Compound Identification | Structure | Name | CPRE Activity* |
|---|---|---|---|
| A | 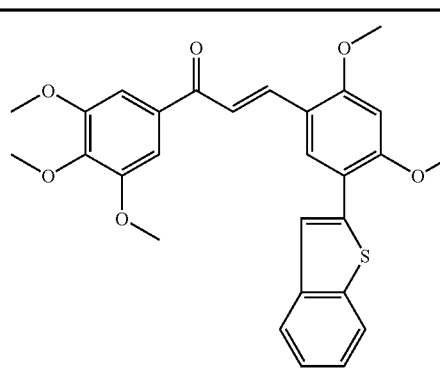 | 3-(5-Benzo-[b]-thiophene-2-yl-2,4-dimethoxy-phenyl)-1-(3,4,5-trimethoxy-phenyl)propenone | 4.5 |

TABLE 6-continued

Activation of p3xCPRE/Luc by small molecular weight organic compounds

| Compound Identification | Structure | Name | CPRE Activity* |
|---|---|---|---|
| B | 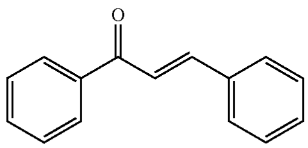 | 1,3-diphenylpropenone | 25 |
| C | 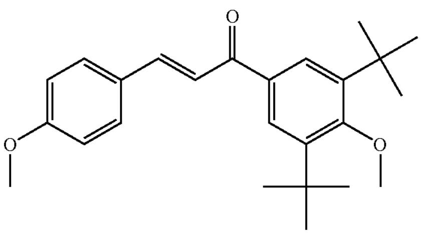 | 1-(3,5-di-tert-butyl-4-methoxyphenyl)-3-(4-methoxyphenyl)-propenone | 5 |
| D | 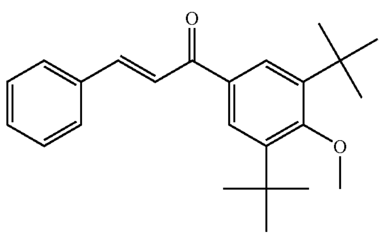 | 1-(3,5-Di-tert-butyl-4-methoxyphenyl)-3-phenyl-propenone | 2.5 |
| E | 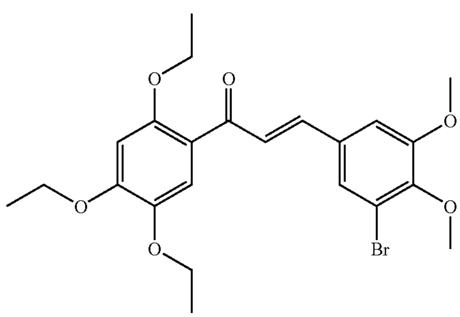 | 3-(3-Bromo-4,5-dimethoxyphenyl)-1-(2,4,5-triethoxyphenyl)-propenone | 12.5 |
| F | 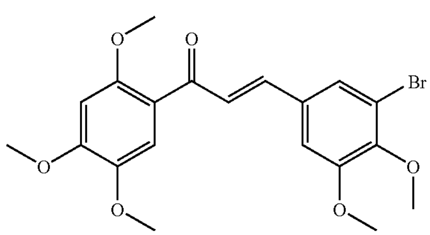 | 1-(3-Bromo-4,5-dimethoxyphenyl)-1-(2,4,5-trimethoxy-phenyl)propenone | 1 |
| G | 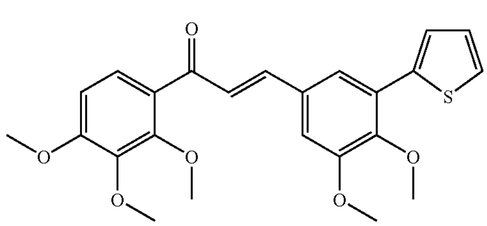 | 3-(3,4-Dimethoxy-5-thiophen-2-ylphenyl)-1-(2,3,4-trimethoxy-phenyl)propenone | 3 |

TABLE 6-continued

Activation of p3xCPRE/Luc by small molecular weight organic compounds

| Compound Identification | Structure | Name | CPRE Activity* |
|---|---|---|---|
| H | 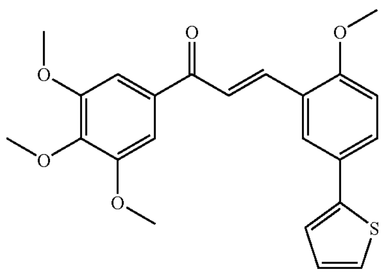 | 3-(2-Methoxy-5-thiophen-2-ylphenyl)-1-(3,4,5-trimethoxyphenyl)propenone | 2 |
| I | 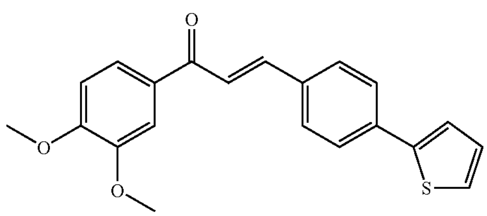 | 1-(3,4-Dimethoxyphenyl)-3-(4-thiophen-2-ylphenyl)propenone | 8 |
| J | 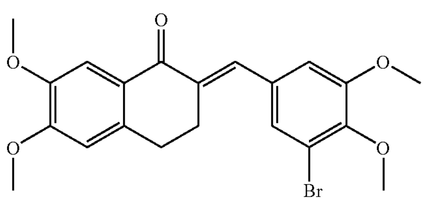 | 2-(3-Bromo-4,5-dimethoxybenzylidene)-6,7-dimethoxy-3,4-dihydro-2H-naphthalen-1-one. | 3 |
| K | 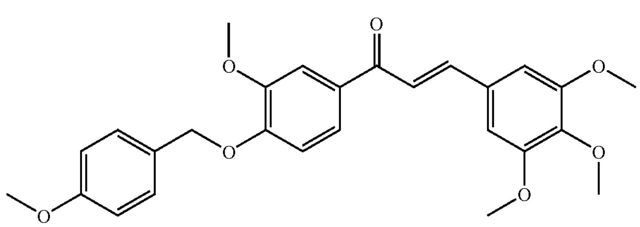 | 1-[3-(Methoxy-4-(4-methoxybenzyloxy)-phenyl]-3-(3,4,5-trimethoxyphenyl)-propenone | 2 |
| L | 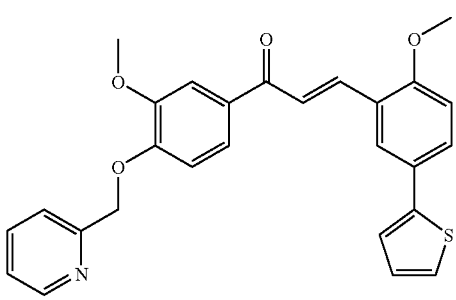 | 1-[3-Methoxy-4-(pyridin-2-ylmethoxy)-phenyl]-3-(2-methoxy-5-thiophen-2-yl-phenyl)propenone | 0.7 |

TABLE 6-continued

Activation of p3xCPRE/Luc by small molecular weight organic compounds

| Compound Identification | Structure | Name | CPRE Activity* |
|---|---|---|---|
| M | 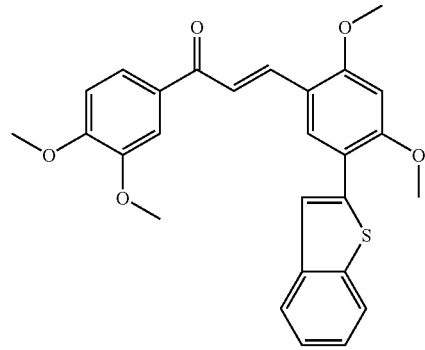 | 3-(5-Benzo[b]thiophene-2-yl-2,4-dimethoxyphenyl)-1-(3,4-dimethoxyphenyl)-propenone | 2.5 |
| N | 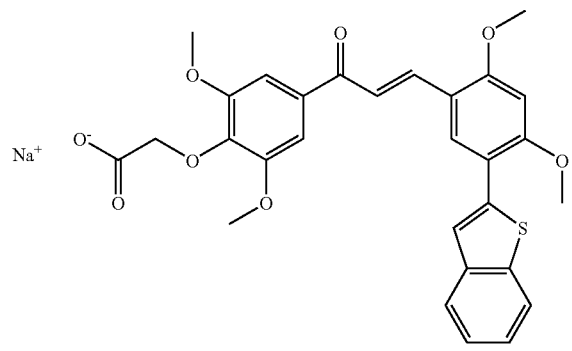 | Sodium {4-[3-(5-benzo[b]thiophene-2-yl-2,4-dimethoxyphenyl)acryloyl]-2,6-dimethoxyphenoxy}-acetate | 1.4 |
| O | 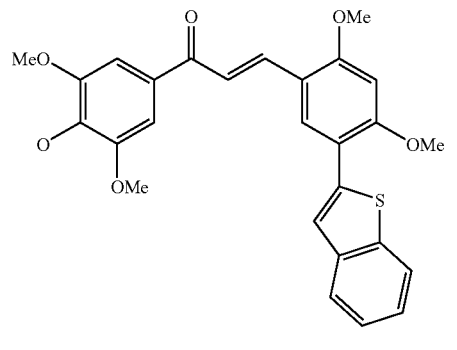 | 3-(5-Benzo[b]thiophene-2-yl-2,4-dimethoxyphenyl)-1-(4-hydroxy-3,5-dimethoxyphenyl)-propenone | 0.7 |
| P | 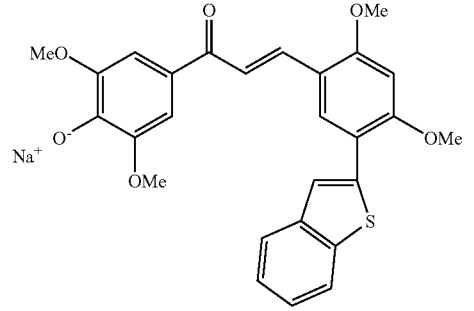 | Sodium 4-[3-(5-benzo[b]thiophene-2-yl-2,4-dimethoxyphenyl)acryloyl]-2,6-dimethoxyphenolate | 1 |

TABLE 6-continued

Activation of p3xCPRE/Luc by small molecular weight organic compounds

| Compound Identification | Structure | Name | CPRE Activity* |
|---|---|---|---|
| Q | 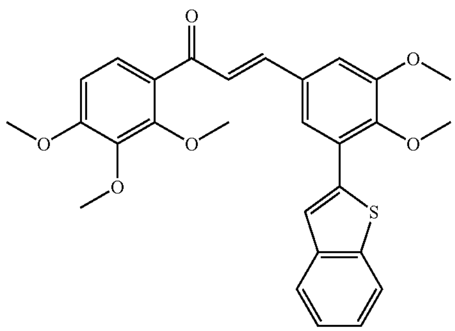 | 3-(3-Benzo[b]thiophene-2-yl-4,5-dimethoxyphenyl)-1-(2,3,4-trimethoxyphenyl)propenone | 2.5 |
| R | 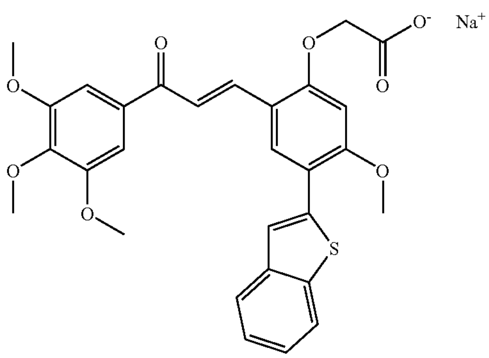 | Sodium {4-benzo[b]thiophene-2-yl-5-methoxy-2-[3-oxo-3-(3,4,5-trimethoxyphenyl)-propenyl]phenoxy}-acetate | 14 |

*Value represents the concentration (µM) to achieve a two-fold induction of CPRE activity over control.

Example 11

Compound A Demonstrates Anti-inflammatory Activity in Vivo

Compounds that activate the CPRE can demonstrate anti-inflammatory activity. This is because many inflammatory processes, including expression of the redox sensitive genes VCAM-1 and MCP-1, are subject to regulation by redox pathways. Therefore, if CPRE-regulated genes modulate the redox balance of the cell by preventing the accumulation of oxidant signals, then it is likely that compound that activate the CPRE can demonstrate anti-inflammatory properties in vivo. In cell culture models compound A inhibits the TNF-α-activated cell surface expression of VCAM-1 with an $IC_{50}$ of~1.4 µM.

To evaluate the anti-inflammatory potential of compound A, a murine model of Type 1 hypersensitivity was used. In this model mice are sensitized to ovalbumin and subsequently challenged with ovalbumin by intraperitoneal injection. This leads to eosinophil recruitment and accumulation in the peritoneal cavity 24-48 hours after the challenge. As shown in FIG. 15, compound A, when administered by intravenous injection either one or four hours prior to antigen challenge resulted in a significantly significant reduction in the number of eosinophils elicited into the peritoneum. The level of inhibition was comparable to dexamethosone that was used as a positive control. These results demonstrate that compounds that activate transcription of the CPRE also have anti-inflammatory properties in animal models of inflammation. These results therefore demonstrate the utility of using a CPRE-based reporter construct in either transient transfections or as stable cell lines to screen for inhibitors of inflammatory processes.

6-8 week old Balb/c mice (weighing 20-30 g) were given subcutaneous injections of ovalbumin in alum (0.4 ml of 100 µg ovalbumin and 3.3 mg of Alum Inject) on days 0 and 7. The mice were challenged on day 14 with an intraperitoneal injection of ovalbumin (10 µg in 0.2 ml saline). The mice were sacrificed and peritoneal lavage fluid collected 48 hours after the challenge. The peritoneal fluid was concentrated and slide smears made using a cytospin centrifuge. Slides were stained with Diff-Quik and differential counts obtained by counting 300 cells. Compound A was administered by intravenous injection, in a vehicle composed of 95% Liposyn and 5% Tween 20, 4 or 1 hour prior to challenge. Compound A was compared to dexamethosone administered orally at a dose of 2.5 mg/kg/d.

Example 12

Effects of Compound A in Mouse Asthma Model-airway Eosinophilia and Hyperreactivity Male BALB-C mice, 6 weeks of age, were randomly assigned to one of following groups: ova/ova, vehicle control, dexamethasone (3 mg/kg) treatment, and Compound A. Animals were weighed on day 0, 7, 12 and 14 and were given access to food and water ad libidum. Mice were sensitized intraperitoneally with 8 µg of ovalbumin and 1 mg of aluminum hydroxide on Day 0 and Day 5. The animals were exposed to aerosolized ovalbumin (0.5%) twice on Day 12 (1 hr & 10 minutes per exposure). The ovalbumin exposures were separated by at least 4 hours. Differentials were performed on bronchoaveolar lavage fluid on Day 14 to determine % eosinophils. Compound A was orally administered daily at a dose of 300 mg/kg from time of sensitization to termination of study to the Compound A group. Compound A was found to inhibit eosinophilia by 48% compared with vehicle controls (p<0.05) in the bronchoaveolar lavage fluid of ovalbumin-sensitized and challenge mice. See FIG. 16. In addition, it improved lung function (decreased airway hyperreactivity to methacholine) in these mice compared to vehicle controls. See FIG. 17.

Example 13

Effect of Compound A in Mouse Delayed Type Hypersensitivity Model

Balb/C mice were divided into two groups: control/vehicle and treated. They were sensitized intradermally on day 0 with methylated BSA (metBSA), and then challenged with metBSA on day 7 in the right hind paw. Compound A was administered at a dose of 100 mg/kg to the treated group by intraperitoneal injection −24, −1 and +6 hrs from the time of challenge. All animals were sacrificed 24 hours later and the left and right hind paws weighed. The left hind paw weight was subtracted from the right hind paw to give the paw weight increase. Compound A was found to inhibit paw swelling by 79% compared with the vehicle controls. See FIG. 18.

Example 14

Effect of Compound G in a Mouse Peritonitis Model

In a common allergic inflammation, balb/C mice were divided into two groups: control/vehicle and Compound G treated. They were then sensitized to ovalbumin on days 0 and 7 with a subcutaneous injection of ovalbumin absorbed in aluminum hydroxide. The treated group was dosed i.v. 50 mg/kg in liposyn/tween and vehicle one day prior to challenge. The mice were then challenged with an intraperitoneal injection of ovalbumin on day 14 and sacrificed 48 hrs post-challenge. Peritoneal fluid was collected and spun down onto slides. Slides were stained with DiffQuik and a differential performed. Compound G was found to inhibit eosinophilia by 39% compared with vehicle controls. See FIG. 19.

While the foregoing invention has been described in some detail for purposes of clarity and understanding, it will be appreciated by one skilled in the art from a reading of this disclosure that various changed in form and detail can be made without departing from the true scope of the invention.

We claim:

1. An isolated nucleic acid consisting of SEQ ID NO:1.

2. A nucleic acid construct consisting of SEQ ID NO:1, operably linked to a heterologous protein coding sequence.

3. A nucleic acid construct comprising a cytoprotective response element consisting of SEQ ID NO:1.

4. A nucleic acid construct comprising a cytoprotective response element consisting of SEQ ID NO:1 operably linked to a promoter.

5. The construct of claim 4 wherein the promoter is operably linked to a reporter gene.

6. The construct of claim 4 or 5 wherein the promoter is selected from the group consisting of SV40, CMV and TK.

7. The construct of claim 5 wherein the reporter gene is selected from the group consisting of luciferase, CAT, secreted alkaline phosphatase, green fluorescent protein, and human growth hormone.

8. A nucleic acid construct consisting of one to ten cytoprotective response elements wherein the cytoprotective response element is SEQ ID NO:1 that induces the expression of microsomal epoxide hydroxylase.

9. An isolated nucleic acid construct comprising two to ten cytoprotective response elements wherein the cytoprotective response element is SEQ ID NO:1.

10. An isolated nucleic acid construct comprising three to ten cytoprotective response elements wherein the cytoprotective response element is SEQ ID NO:1.

11. The construct of claim 9 wherein the cytoprotective response elements are operably linked to a promoter.

12. The construct of claim 11 wherein the promoter is operably linked to a reporter gene.

13. The construct of claim 11 or 12 wherein the promoter is selected from the group consisting of SV40, CMV and TK.

14. The construct of claim 12 wherein the reporter gene is selected from the group consisting of luciferase, CAT, secreted alkaline phosphatase, green fluorescent protein, and human growth hormone.

15. The construct of claim 10 wherein the cytoprotective response elements are operably linked to a promoter.

16. The construct of claim 15 wherein the promoter is operably linked to a reporter gene.

17. The construct of claim 15 or 16 wherein the promoter is selected from the group consisting of SV40, CMV and TK.

18. The construct of claim 6, wherein the reporter gene is selected from the group consisting of luciferase, CAT, secreted alkaline phosphatase, green fluorescent protein, and human growth hormone.

19. The construct of claim 13 wherein the reporter gene is selected from the group consisting of luciferase, CAT, secreted alkaline phosphatase, green fluorescent protein, and human growth hormone.

20. The construct of claim 3, wherein the construct is a vector.

* * * * *